(12) United States Patent
Asokan et al.

(10) Patent No.: US 12,146,151 B2
(45) Date of Patent: *Nov. 19, 2024

(54) CROSS-SPECIES COMPATIBLE ADENO-ASSOCIATED VIRUS COMPOSITIONS AND METHODS OF USE THEREOF

(71) Applicant: Duke University, Durham, NC (US)

(72) Inventors: Aravind Asokan, Durham, NC (US); Trevor Gonzalez, Durham, NC (US); Lawrence Patrick Havlik, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/474,506

(22) Filed: Sep. 26, 2023

(65) Prior Publication Data

US 2024/0067988 A1    Feb. 29, 2024

Related U.S. Application Data

(63) Continuation of application No. 17/922,962, filed as application No. PCT/US2021/030937 on May 5, 2021.

(60) Provisional application No. 63/020,062, filed on May 5, 2020.

(51) Int. Cl.
| | |
|---|---|
| *C12N 15/864* | (2006.01) |
| *C07K 14/005* | (2006.01) |
| *C12N 5/10* | (2006.01) |
| *C12N 15/34* | (2006.01) |
| *C12N 15/86* | (2006.01) |

(52) U.S. Cl.
CPC ............ *C12N 15/86* (2013.01); *C07K 14/005* (2013.01); *C12N 2750/14122* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,478,745 A | 12/1995 | Samulski et al. | |
| 7,314,912 B1 | 1/2008 | Hallek et al. | |
| 7,906,111 B2* | 3/2011 | Wilson ................... | C12N 9/644 |
| | | | 435/456 |
| 2007/0036760 A1 | 2/2007 | Wilson et al. | |
| 2012/0137379 A1 | 5/2012 | Gao et al. | |
| 2016/0017295 A1 | 1/2016 | Schaffer et al. | |
| 2017/0067908 A1 | 3/2017 | Nakai et al. | |
| 2017/0130245 A1 | 5/2017 | Kotin et al. | |
| 2019/0048041 A1 | 2/2019 | Asokan et al. | |
| 2020/0109418 A1 | 4/2020 | Li et al. | |
| 2021/0371471 A1* | 12/2021 | McCoy ................... | C12N 7/00 |

FOREIGN PATENT DOCUMENTS

| | | |
|---|---|---|
| WO | 2000/028004 | 5/2000 |
| WO | 2001/092551 | 12/2001 |
| WO | 2005/033321 | 4/2005 |
| WO | 2015/164757 | 10/2015 |
| WO | 2017/058892 | 4/2017 |
| WO | 2019/195444 | 10/2019 |
| WO | 2019/222444 | 11/2019 |
| WO | 2020/191300 | 9/2020 |

OTHER PUBLICATIONS

Chao H, et al. (2000) Several log increase in therapeutic transgene delivery by distinct adeno-associated viral serotype vectors. Mol Ther. 2(6):619-623.
Cleves AE. (1997) Protein transports: the nonclassical ins and outs. Curr Biol. 7(5):R318-R320.
Gao G, et al. (2004) Clades of Adeno-associated viruses are widely disseminated in human tissues. (12):6381-6388.
Gonzalez TJ, et al. (2022) Cross-species evolution of a highly potent AAV variant for therapeutic gene transfer and genome editing. Nat Commun. 13(1):5947, pp. 1-17.
Grifman M, et al. (2001) Incorporation of tumor-targeting peptides into recombinant adeno-associated virus capsids. Mol Ther. 3(6):964-975.
Hauck B, et al. (2003) Characterization of tissue tropism determinants of adeno-associated virus type 1. J Virol. 77 (4):2768-2774.
McCarty DM, et al. (2001) Self-complementary recombinant adeno-associated virus (scAAV) vectors promote efficient transduction independently of DNA synthesis. Gene Ther. 8(16):1248-1254.
Mori S, et al. (2004) Two novel adeno-associated viruses from cynomolgus monkey: pseudotyping characterization of capsid protein. Virology. 330(2):375-383.
Muzyczka N. (1992) Use of adeno-associated virus as a general transduction vector for mammalian cells. Curr Top Microbiol Immunol. 158:97-129.
Naso MF, et al. (2017). Adeno-Associated Virus (AAV) as a Vector for Gene Therapy. BioDrugs. 31(4):317-334.
Shi X, et al. (2006) Insertional mutagenesis at positions 520 and 584 of adeno-associated virus type 2 (AAV2) capsid gene and generation of AAV2 vectors with eliminated heparin-binding ability and introduced novel tropism. Hum Gene Ther. 17(3):353-361.
Tse LV, et al. (2017) Structure-guided evolution of antigenically distinct adeno-associated virus variants for immune evasion. Proc Natl Acad Sci USA. 114(24):E4812-E4821.
Wang L, et al. (2006) Expanding the genetic code. Annu Rev Biophys Biomol Struct. 35:225-249.
Agbandje-Mckenna, M. et al. (2011) AAV capsid structure and cell interactions. Methods Mol Biol. 807:47-92.

(Continued)

*Primary Examiner* — Maria Marvich
(74) *Attorney, Agent, or Firm* — POLSINELLI PC

(57) ABSTRACT

The present disclosure provides adeno-associated virus (AAV) vectors, comprising coevolved capsid variant proteins, pharmaceutical compositions, methods of making, and methods for delivering such to a subject.

20 Claims, 34 Drawing Sheets

Specification includes a Sequence Listing.

(56) References Cited

OTHER PUBLICATIONS

International Search Report and Written Opinion for PCT/US2021/030937 mailed Oct. 29, 2021 (Applicant: Duke University) (13 Pages).

Picconi JL, et al. (2014) Kidney-specific expression of GFP by in-utero delivery of pseudotyped adeno-associated virus 9. Mol Ther Methods Clin Dev. 1:14014.

Buning H, et al. (2019) Capsid Modifications for Targeting and Improving the Efficacy of AAV Vectors. Mol Ther Methods Clin Dev. 12:248-265.

Dayton RD, et al. (2012) The advent of AAV9 expands applications for brain and spinal cord gene delivery. Expert Opin Biol Ther. 12(6):757-766.

\* cited by examiner

Fig. 5A
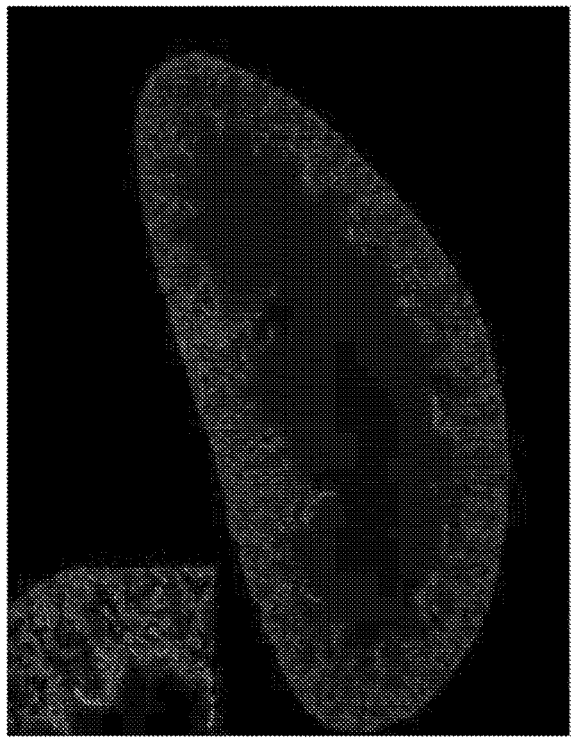
Fig. 5B
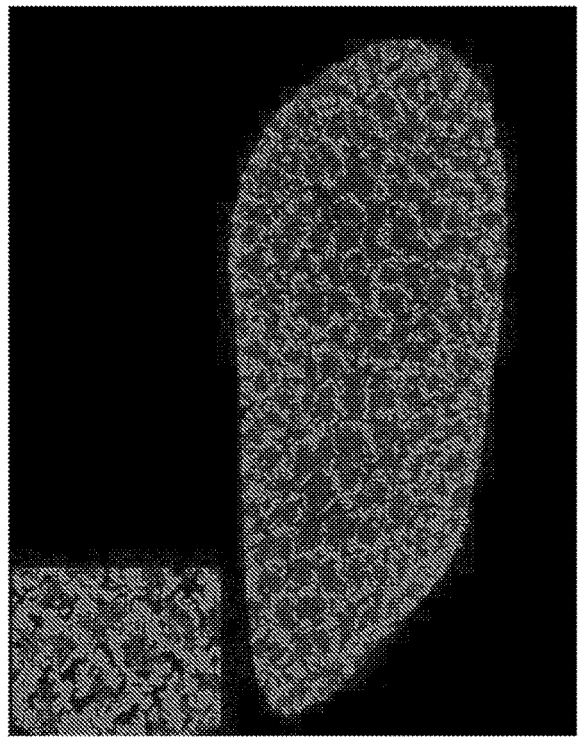
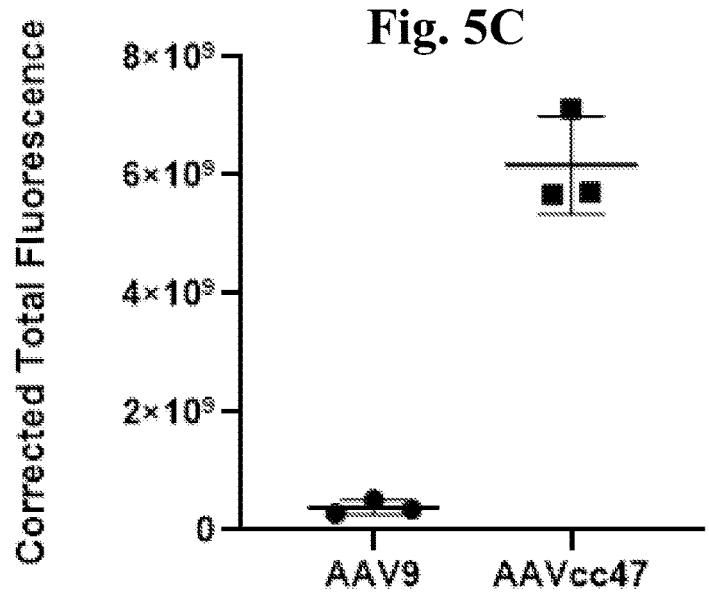
Fig. 5C

Fig. 6A
Fig. 6B
Fig. 6C
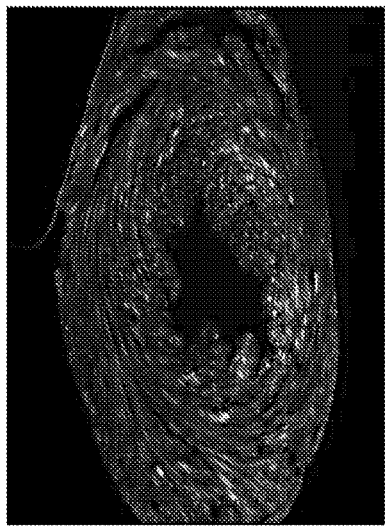 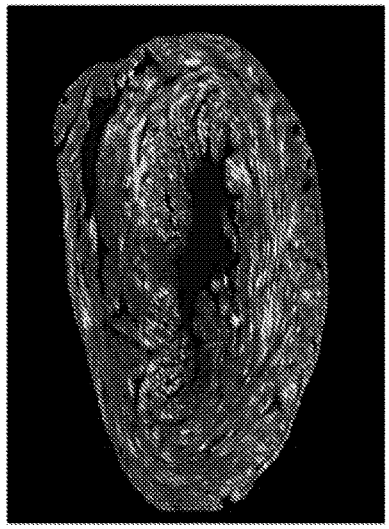 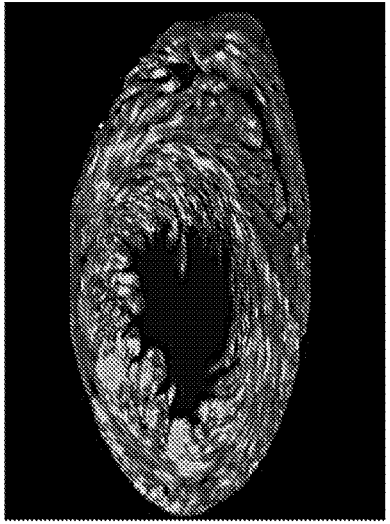
Fig. 6D
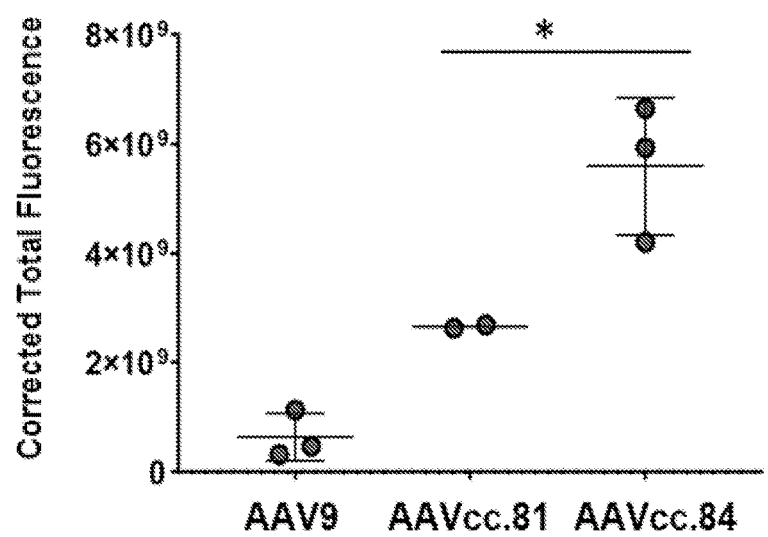

Fig. 9A
Fig. 9B
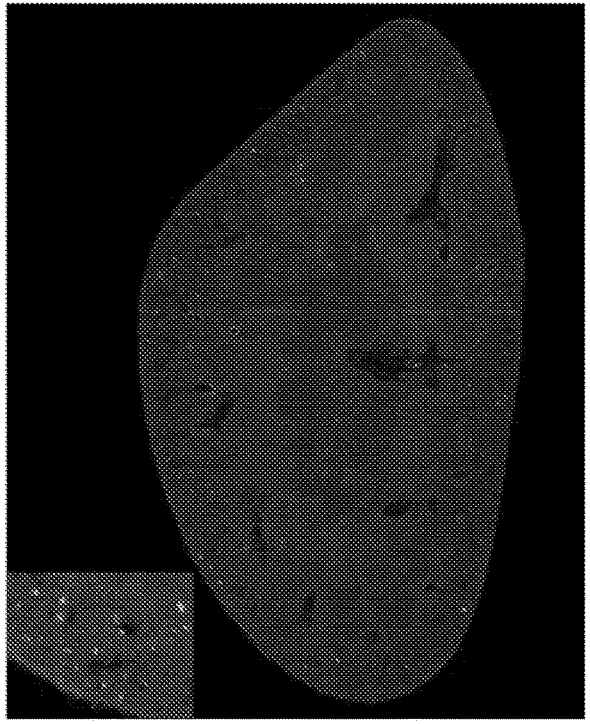
Fig. 9C
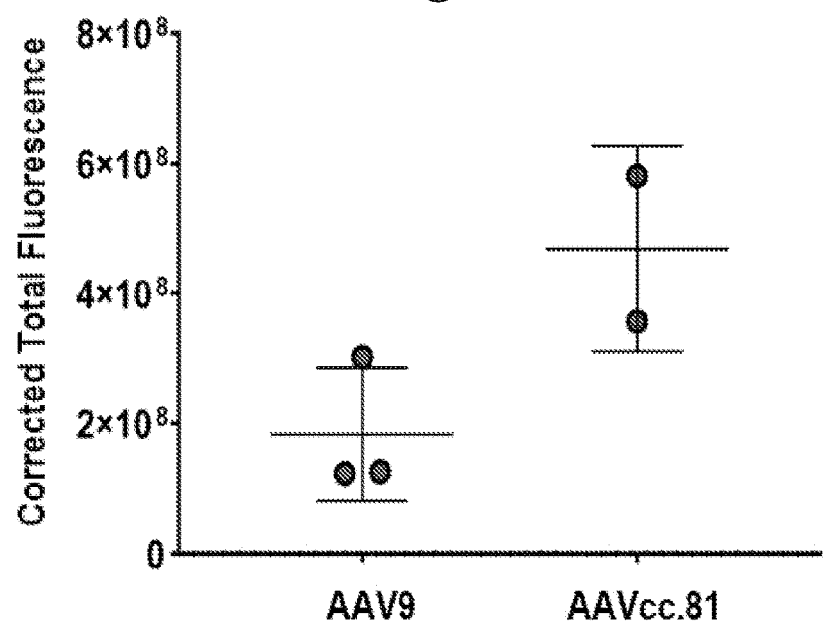

Frontal Cortex

Parietal Cortex

Thalamus

Occipital Cortex

Brainstem

Cerebellum

Midbrain

Frontal Cortex

Parietal Cortex

Thalamus

Occipital Cortex

Brainstem

Cerebellum

Midbrain

AAVcc.47

AAVcc.84

White matter

White matter

Grey matter

Grey matter

Left Ventricle

Right Ventricle

Liver

Left Ventricle

Right Ventricle

Liver

Mock

AAV9 cc47 cc84

Fig. 19A Mock
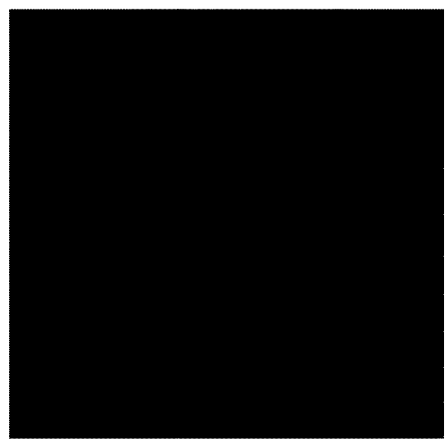
Fig. 19B AAV9
Fig. 19C cc47
Fig. 19D cc84
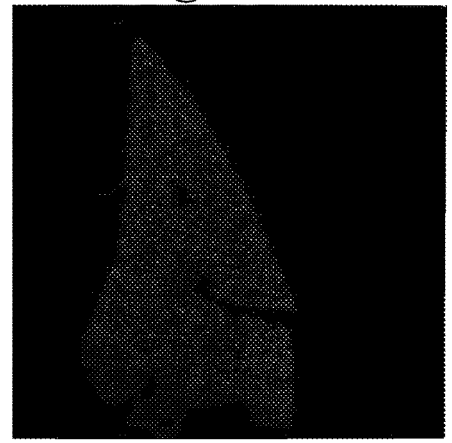
Fig. 19E
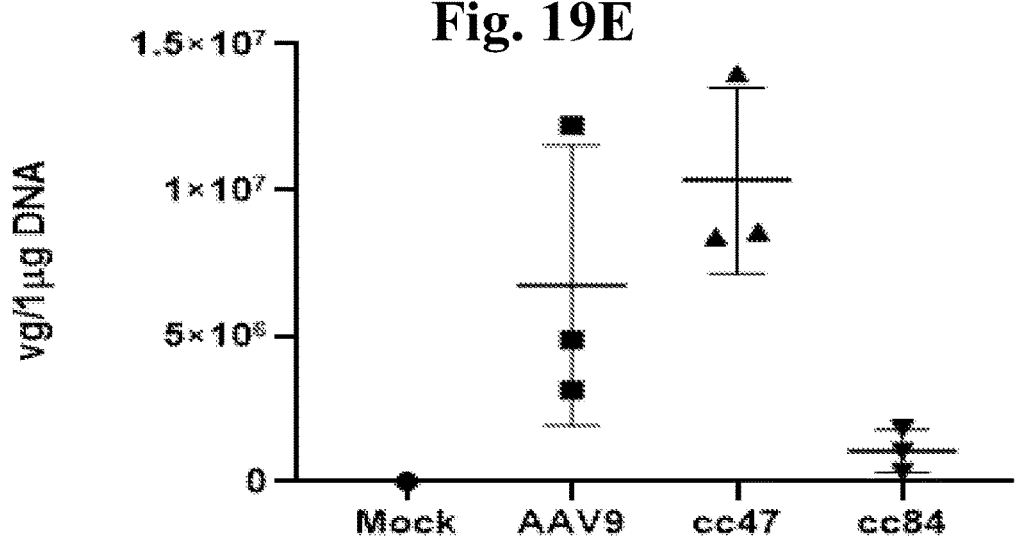

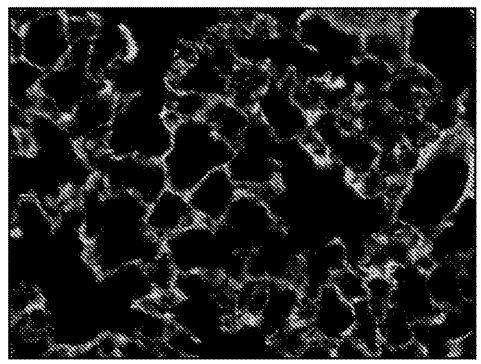
Fig. 20A Mock
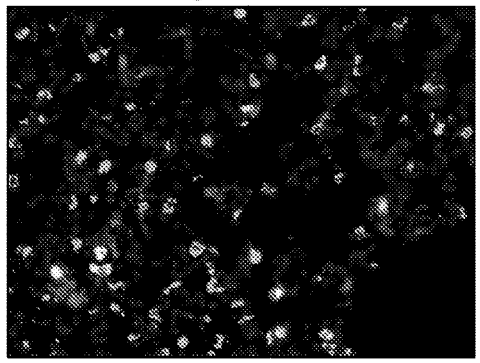
Fig. 20B AAV9
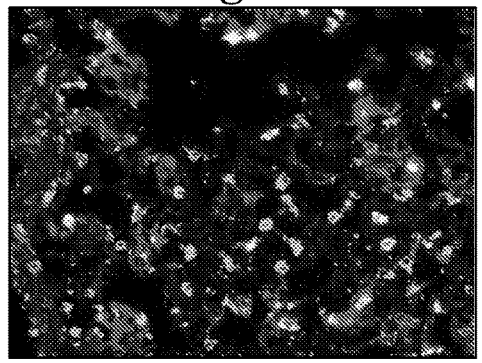
Fig. 20C cc47
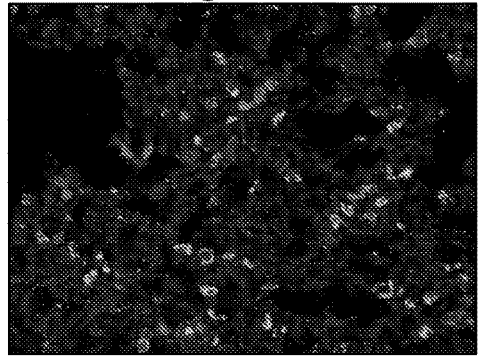
Fig. 20D cc84
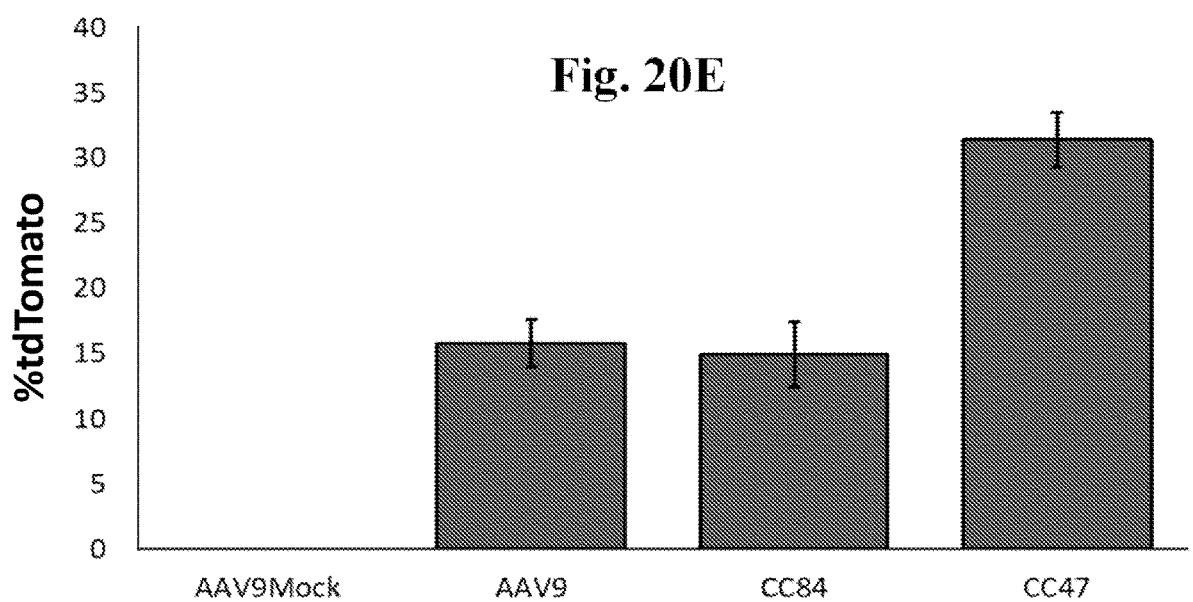
Fig. 20E

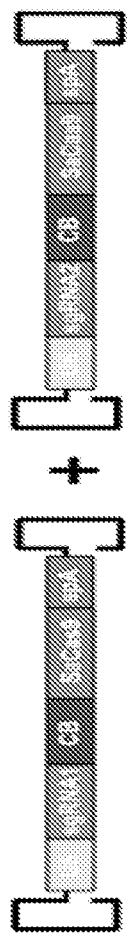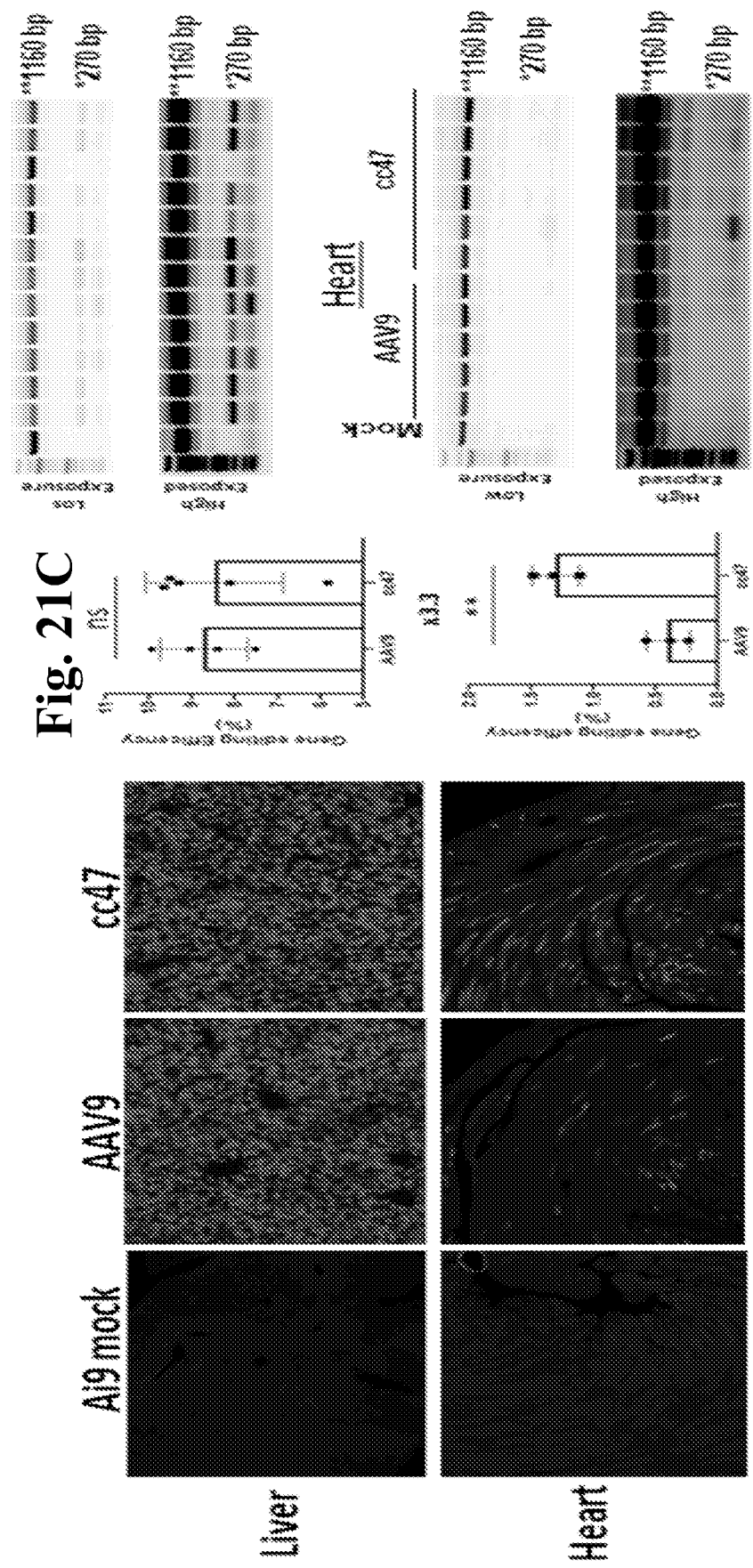
Fig. 21A Fig. 21B Fig. 21C Fig. 21D

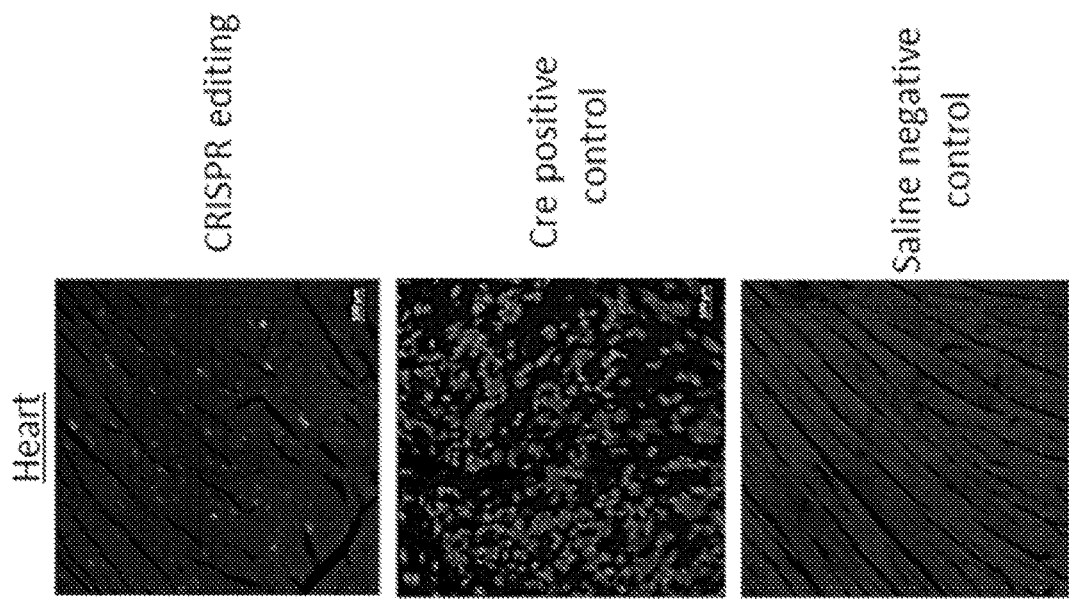
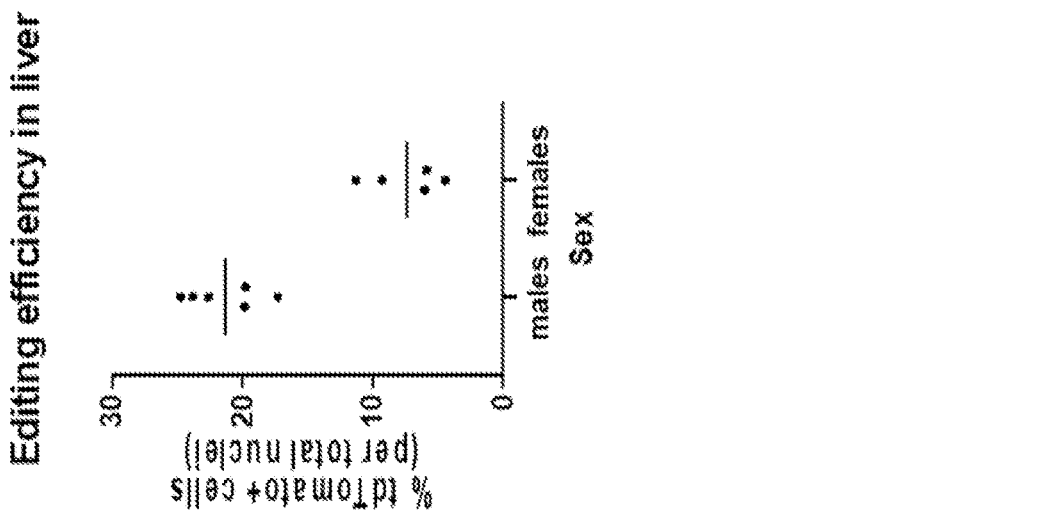
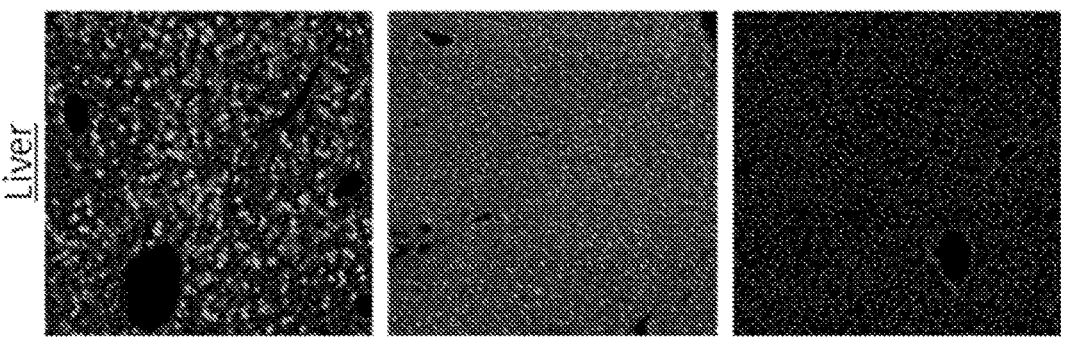

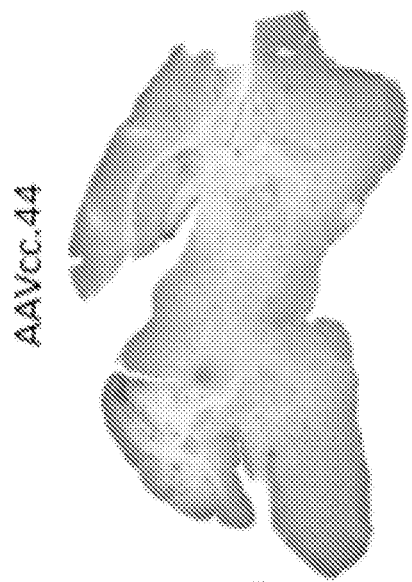
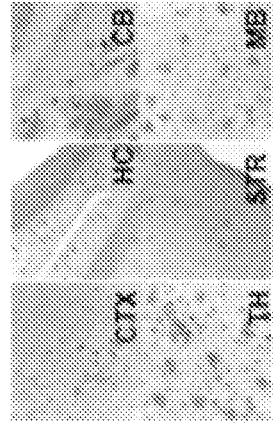
Fig. 28A Mock
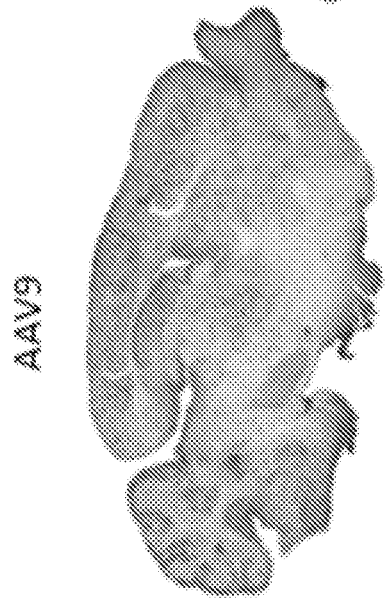
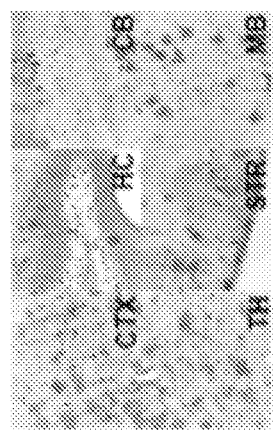
Fig. 28B AAV9
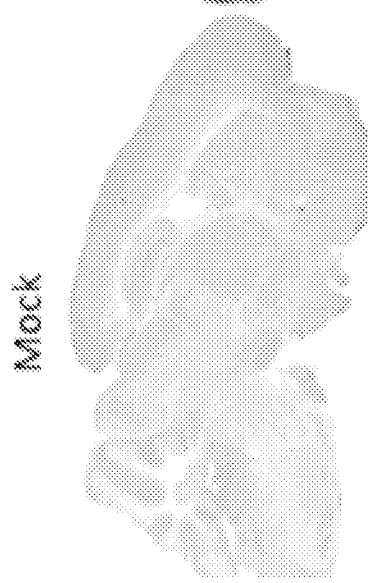
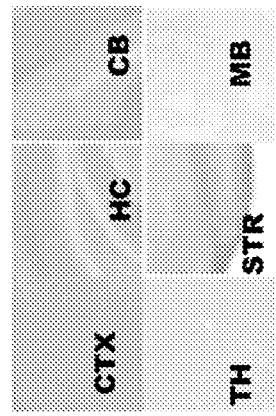
Fig. 28C AAVcc.44

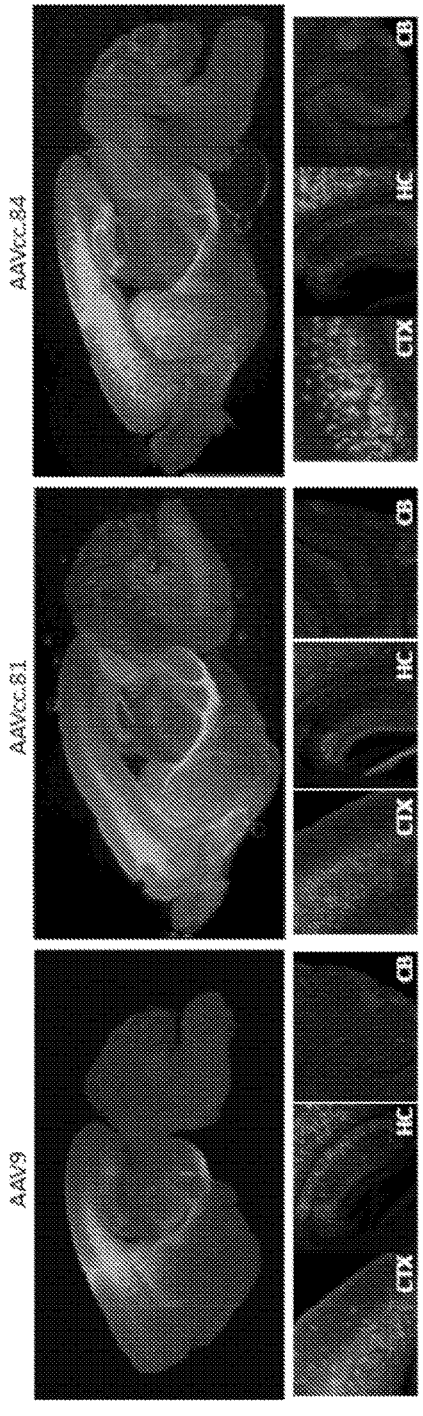
Fig. 30A Fig. 30B Fig. 30C Fig. 30D Fig. 30E Fig. 30F

CB

HC

CTX

CROSS-SPECIES COMPATIBLE ADENO-ASSOCIATED VIRUS COMPOSITIONS AND METHODS OF USE THEREOF

CROSS-REFERENCE TO RELATED APPLICATIONS

This application is a continuation of U.S. application Ser. No. 17/922,962 filed 2 Nov. 2022, which is a national phase application of International Application No. PCT/US2021/030937 filed 5 May 2021, which claims priority to U.S. Provisional Application Ser. No. 63/020,062, filed May 5, 2020, the contents of each are incorporated by reference herein in their entirety for all purposes.

FEDERAL FUNDING LEGEND

This invention was made with Government support under Federal Grant Nos. R01HL089221 and UG3AR075336, both awarded by the National Institutes of Health. The Federal Government has certain rights to this invention.

FIELD OF THE DISCLOSURE

The present disclosure relates to modified capsid proteins from adeno-associated virus (AAV) and virus capsids and virus vectors comprising the same. In particular, the disclosure relates to modified AAV capsid proteins and capsids comprising the same that can be incorporated into virus vectors to enable expression in any cell or tissue type in a mammalian subject.

INCORPORATION BY REFERENCE OF SEQUENCE LISTING PROVIDED ELECTRONICALLY

The Sequence Listing submitted on 26 Sep. 2023 as an .xml file is incorporated by reference herein in its entirety. The .xml file is 219 kilobytes in size and is titled "21-2006-US-CON1 SEQUENCE LISTING".

BACKGROUND

Adeno-associated virus (AAV) vectors have become a leading platform for gene therapy for the treatment of a variety of diseases. Although there has been clinical success using AAV-based gene therapies, limitations and challenges associated with use of this gene delivery platform remain. For example, the efficacy of gene therapy with vectors (viral or non-viral) is sometimes reduced because of the subject's immune response against the vector carrying the gene. Additionally, routes of administration must be optimized to ensure delivery to one or more target tissues in the subject. This is particularly true in treating disorders of the central nervous systems (CNS) and peripheral nervous systems (PNS). The blood brain barrier can impede access of the AAV-based therapy to the CNS when administered systemically and direct administration to CNS tissues can involve invasive surgeries. Further, the high doses of AAV-based therapies necessary to yield sufficient transduction of target CNS and PNS tissues increases the risk of side effects, and/or undesired immune responses. Additionally, the need to produce high doses of AAV poses a manufacturing burden.

Known AAV serotypes each have a specific tissue tropism, and there are some tissues (e.g., kidney) that cannot be easily targeted using these AAVs. Additionally, AAV transduction in systemic organs such as the heart, liver or lung can vary significantly for a given dose in various model organisms used during clinical development (e.g., canine, pig, non-human primates) and in human subjects. This inability to accurately test AAV-based therapies in animal models prior to human use is also problematic.

As the scope of AAV gene transfer applications has expanded, including the advancement of gene-therapies to CNS and/or PNS disorders, there remains a need in the art to address differences in AAV tropism across different species. These differences often result in non-linear vector dose biodistribution relationships when scaling from small to large animal models—subsequently impacting clinical translation. As such, there is an unmet need in the art to develop AAV gene delivery platforms with greater translatability across multiple species. Additionally, there is a need to develop AAV-based gene therapies that are able to selectively and specifically target tissues of interest, including tissues that are have been difficult to target using known AAV serotypes.

BRIEF SUMMARY OF THE DISCLOSURE

The present disclosure provides, at least in part, methods and compositions comprising an adeno-associated virus (AAV) capsid protein, comprising one or more amino acid substitutions, wherein the substitutions introduce into an AAV vector comprising these modified capsid proteins one or more improved functionalities such as, but not limited to, the ability to evade host antibodies, selective tropism, and/or higher transduction efficiency.

An aspect of the present disclosure provides for recombinant AAV vectors comprising an AAV capsid protein variant as disclosed herein. In some embodiments, recombinant AAV vectors herein may comprise an AAV capsid protein variant, wherein the capsid protein variant comprises a peptide having the sequence of any one of SEQ ID NOs: 2-19. In some embodiments, recombinant AAV vectors herein comprises an AAV capsid protein variant, wherein the capsid protein variant has at least 90% identity to the sequence of SEQ ID NO: 1, wherein the amino acids corresponding to amino acids 452-458 of SEQ ID NO: 1 are be substituted with a peptide having a sequence of any one of SEQ ID NOs: 20-28. In some embodiments, recombinant AAV vectors herein may comprise an AAV capsid protein variant, wherein the capsid protein variant has at least 90% identity to the sequence of SEQ ID NO: 1, wherein the amino acids corresponding to amino acids 586-592 of SEQ ID NO: 1 are be substituted with a peptide having a sequence of any one of SEQ ID NOs: 29-37.

In some embodiments, recombinant AAV vectors herein comprises an AAV capsid protein variant, wherein the capsid protein variant has at least 90% identity to the sequence of SEQ ID NO: 1, wherein the amino acids corresponding to amino acids 452-458 of SEQ ID NO: 1 are substituted with a peptide having a sequence of any one of SEQ ID NOs: 20-28; and wherein the amino acids corresponding to amino acids 586-592 of SEQ ID NO: 1 are substituted with a peptide having a sequence of any one of SEQ ID NOs: 29-37.

In some embodiments, recombinant AAV vectors herein may comprise an AAV capsid protein variant, wherein the capsid protein variant has the sequence of any one of SEQ ID NO: 2-19, 46-123 or a sequence with at least 90% or at least 95% identity thereto. In some embodiments, recombinant AAV vectors herein comprise an AAV capsid protein variant, wherein the capsid protein variant has the sequence of any one of SEQ ID NO: 2-19, 46-123 or a sequence with 1-10, 11-20, 20-30, or 30-50 amino acid substitutions relative thereto.

Another aspect of the present disclosure provides for AAV capsid protein variants as disclosed herein. In some embodiments, AAV capsid protein variants herein comprise a peptide having the sequence of any one of SEQ ID NOs: 2-19.

In some embodiments, AAV capsid protein variants herein have at least 90% identity to the sequence of SEQ ID NO: 1, wherein the amino acids corresponding to amino acids 452-458 of SEQ ID NO: 1 are substituted with a peptide having a sequence of any one of SEQ ID NOs: 20-28. In some embodiments, AAV capsid protein variants herein have at least 90% identity to the sequence of SEQ ID NO: 1, wherein the amino acids corresponding to amino acids 586-592 of SEQ ID NO: 1 are substituted with a peptide having a sequence of any one of SEQ ID NOs: 29-37.

In some embodiments, AAV capsid protein variants herein may have at least 90% identity to the sequence of SEQ ID NO: 1, wherein the amino acids corresponding to amino acids 452-458 of SEQ ID NO: 1 may be substituted with a peptide having a sequence of any one of SEQ ID NOs: 20-28; and wherein the amino acids corresponding to amino acids 586-592 of SEQ ID NO: 1 may be substituted with a peptide having a sequence of any one of SEQ ID NOs: 29-37.

In some embodiments, AAV capsid protein variants herein may have the sequence of any one of SEQ ID NO: 2-19, 46-123 or a sequence with at least 90% or at least 95% identity thereto. In some embodiments, capsid protein variants herein may have the sequence of any one of SEQ ID NO: 2-19, 46-123 or a sequence with 1-10, 11-20, 20-30, or 30-50 amino acid substitutions relative thereto.

Another aspect of the present disclosure provides for pharmaceutical compositions comprising any of the of the AAV capsid protein variants and/or AAV vectors disclosed herein. In some embodiments, pharmaceutical compositions herein may further comprise at least one pharmaceutically acceptable carrier.

Another aspect of the present disclosure provides for methods of introducing a recombinant AAV vector into a target cell. In some embodiments, the methods of introducing a recombinant AAV vector into a target cell herein may include contacting the target cell with any of the recombinant AAV vectors (e.g., ccAAVs) and/or pharmaceutical compositions disclosed herein. In some embodiments, methods herein can deliver one or more therapeutic heterologous molecules to a target cell in a subject, the methods comprising administering to the subject any of the recombinant AAV vectors (e.g., ccAAVs) and/or pharmaceutical compositions disclosed herein. In some embodiments, any of the any of the recombinant AAV vectors (e.g., ccAAVs) and/or pharmaceutical compositions disclosed herein can be administered to a subject by intramuscular injection, intravenous injection, intracoronary injection, intraarterial injection, or any combination thereof.

Another aspect of the present disclosure provides for methods of evolving novel strains of adeno-associated viruses comprising passaging AAV capsid libraries across multiple mammalian species. In some embodiments, methods herein may utilize AAV capsid libraries comprising AAV capsids packaging different genomes encoding mutagenized capsid gene sequences. In some embodiments, methods herein may administer AAV capsid libraries herein to *Mus Musculus* (mouse), *Sus scrofa* (pig), *Canis Familiaris* (Dog), Non-human primates (*Macaca*, macaque), or *Homo sapiens* (human), and any combination or repeated cycles thereof. In some embodiments, methods herein may enrich adeno-associated virus (AAV) capsid protein sequences herein by passaging the AAV capsid libraries according to the methods disclosed herein. In some embodiments, methods herein may enrich sequences encoding capsid protein variants herein by extracting the AAV capsid protein variants from cells collected or derived from the group consisting of spinal cord (e.g., glial cells, neurons, endothelial cells), dorsal root ganglion, brain, heart, lung, kidney, skeletal muscle, spleen, pancreas, small intestine, large intestine, or liver tissue, and any combination thereof. In some embodiments, methods herein may produce AAV capsid protein variants as disclosed herein with improved gene transfer efficiency in any mammalian species selected from the group consisting of: *Mus Musculus* (mouse), *Sus scrofa* (pig), *Canis Familiaris* (Dog), Non-human primates (*Macaca*, macaque), or *Homo sapiens* (human), and any combination or repeated cycles thereof. In some embodiments, methods herein may produce AAV capsid protein variants as disclosed herein with improved gene transfer efficiency in any of the cell types or tissues the group consisting of spinal cord, dorsal root ganglion, brain, heart, lung, kidney, skeletal muscle, spleen, pancreas, small intestine, large intestine, or liver tissue, and any combination thereof. In some embodiments, methods herein may produce AAV capsid protein variants as disclosed herein with improved immune response in any of the cell types or tissues the group consisting of spinal cord, dorsal root ganglion, brain, heart, lung, kidney, skeletal muscle, spleen, pancreas, small intestine, large intestine, or liver tissue, and any combination thereof. In some embodiments, methods herein may produce AAV capsid protein variants as disclosed herein with improved tropism in any of the cell types or tissues the group consisting of spinal cord, dorsal root ganglion, brain, heart, lung, kidney, skeletal muscle, spleen, pancreas, small intestine, large intestine, or liver tissue, and any combination thereof.

An aspect of the disclosure provides for kits, wherein a kit can comprise any of the compositions or AAV vectors disclosed herein and at least one container.

BRIEF DESCRIPTION OF THE DRAWINGS

The following drawings form part of the present specification and are included to further demonstrate certain aspects of the present disclosure, which can be better understood by reference to the drawings in combination with the detailed description of specific embodiments presented herein.

As shown in FIG. 1B, next-generation sequencing revealed that the capsid protein of AAVcc47 was the most enriched amino acid sequence (i.e., clone) in the AAV VR4 libraries following three cycles of evolution in three different species.

FIG. 2C shows a graph depicting corrected total cell fluorescence of a series of multiple images. FIG. 2D shows a graph depicting vector biodistribution in the heart of the infected mice.

FIG. 3C shows a graph depicting corrected total cell fluorescence of a series of multiple images.

FIG. 4C shows a graph depicting corrected total cell fluorescence of a series of multiple images. FIG. 4D shows a graph depicting vector biodistribution in the liver of the infected mice.

FIGS. 5A-5C illustrate mCherry reporter gene expression in C57/B6 mouse kidney in accordance with certain embodiments herein. Representative fluorescent microscopy images showing mCherry expression in kidney vibratome sections 24 hours post-fixation with 4% PFA in mice infected with AAV9 (FIG. 5A) or AAV.cc47 (FIG. 5B). FIG. 5C shows a graph depicting corrected total cell fluorescence of a series of multiple images.

FIGS. 6A-6D illustrate GFP reporter gene expression in C57/B6 mouse heart in accordance with certain embodiments herein. Representative fluorescent microscopy images showing GFP expression in heart vibratome sections 24 hours post-fixation with 4% PFA in mice infected with AAV9 (FIG. 6A) or AAV.cc81 (FIG. 6B), or AAV.cc84 (FIG. 6C). FIG. 6D shows a graph depicting corrected total cell fluorescence of a series of multiple images.

FIG. 7C shows a graph depicting corrected total cell fluorescence of a series of multiple images.

FIG. 8D shows a graph depicting corrected total cell fluorescence of a series of multiple images.

FIGS. 9A-9C illustrate GFP reporter gene expression in C57/B6 mouse kidney in accordance with certain embodiments herein. Representative fluorescent microscopy images showing GFP expression in kidney vibratome sections 24 hours post-fixation with 4% PFA in mice infected with AAV9 (FIG. 9A) or AAV.cc81 (FIG. 9B). FIG. 9C shows a graph depicting corrected total cell fluorescence of a series of multiple images.

FIG. 10A depicts brain regions from a mouse that was sham infected whereas FIG. 10B depicts brain regions from a mouse that was infected with AAV9 vectors, FIG. 10C depicts brain regions from a mouse that was infected with AAV.cc47, FIG. 10D depicts brain regions from a mouse that was infected with AAV.cc81, and FIG. 10E depicts brain regions from a mouse that was infected with AAV.cc84. Brain regions shown include: Ctx=cerebral cortex; Hc=hippocampus; Cb=cerebellum; Th=thalamus; Str=striatum; and mb=mushroom body.

FIG. 11A depicts IHC staining for mCherry in the pig frontal cortex. FIG. 11B depicts IHC staining for mCherry in the pig parietal cortex. FIG. 11C depicts IHC staining for mCherry in the pig parietal thalamus. FIG. 11D depicts IHC staining for mCherry in the pig occipital cortex. FIG. 11E depicts IHC staining for mCherry in the pig brainstem. FIG. 11F depicts IHC staining for mCherry in the pig cerebellum. FIG. 11G depicts IHC staining for mCherry in the pig midbrain.

FIG. 12A depicts IHC staining for GFP in the pig frontal cortex. FIG. 12B depicts IHC staining for GFP in the pig parietal cortex. FIG. 12C depicts IHC staining for GFP in the pig parietal thalamus. FIG. 12D depicts IHC staining for GFP in the pig occipital cortex. FIG. 12E depicts IHC staining for GFP in the pig brainstem. FIG. 12F depicts IHC staining for GFP in the pig cerebellum. FIG. 12G depicts IHC staining for GFP in the pig midbrain.

FIG. 15E shows biodistribution of recombinant AAVs in non-human primates.

FIG. 16A shows brain slice from a sham-injected, control non-human primate.

FIG. 17A shows human iPSC cardiomyocytes transduced with AAV9 or cc47 packaging a GFP driven by the Cbh promoter. FIG. 17B shows quantification of percent GFP+ area in multiple images of (FIG. 17A). FIG. 17C shows AAV9 or AAVcc47 packaging CBh:GFP injected IV in a human cardiac patch mouse model. FIG. 17D shows fluorescent imaging of cardiac patch. FIG. 17E shows i.v. administered AAV9 and AAVcc47 delivering GFP under control of an injury-inducible promoter following myocardial infarction. Immunofluorescence for troponin T (red) and GFP (green).

FIG. 18E shows biodistribution of recombinant AAVs in mouse hearts.

FIGS. 19A-19E illustrate representative images of Native tdTomato fluorescence in the mouse liver following i.v. administration of a mock treatment (FIG. 19A), AAV9 (FIG. 19B), AVV.cc47 (FIG. 19C), and AVV.cc84 (FIG. 19D) in accordance with certain embodiments herein. FIG. 19E shows biodistribution of recombinant AAVs in mouse livers.

FIGS. 20A-20E illustrate representative images of Native tdTomato fluorescence in the mouse lung following i.v. administration of a mock treatment (FIG. 20A), AAV9 (FIG. 20B), AVV.cc47 (FIG. 20C), and AVV.cc84 (FIG. 20D) in accordance with certain embodiments herein. FIG. 20E shows biodistribution of recombinant AAVs in mouse livers.

FIGS. 21A-21D illustrate CRISPR/Cas9 gene editing with a ccAAV vector in accordance with certain embodiments herein. FIG. 21A shows a dual vector strategy employed herein using one vector with a truncated CB promoter driving SaCas9 and U6 promoter driving one sgRNA and a second vector of the same design with the second sgRNA. FIG. 21B shows native tdTomato fluorescence in Ai9 mouse liver and heart following administration of AAV9 or cc47 at a dose of 2e12vg/kg. FIG. 21C shows gene editing efficiency determined by counting total number of tdTomato+ cells and dividing by total number of DAPI+ cells. FIG. 21D shows a PCR editing assay where the unedited band (**1160 bp) and edited band (*270 bp) are noted. p**<0.01.

FIGS. 22A-22C illustrate validation of CRISPR/Cas9 gene editing with a ccAAV vector in accordance with certain embodiments herein. FIG. 22A shows Ai9 livers sectioned and imaged for native TdTomato expression. FIG. 22B shows graphs depicting quantification of gene editing efficiencies by counting the total number of TdTomato+ cells and normalizing to the total number of Dapi+ cells. FIG. 22C shows Ai9 hearts were sectioned and imaged for native TdTomato expression. Both tissues were cryosectioned into 14 µm thick sections.

FIG. 23A shows a graph of the corrected total cell fluorescence in the livers of all injected Ai9 mice. FIG. 23B shows a graph of the corrected total cell fluorescence in the livers of all injected female Ai9 mice. FIG. 23C shows a graph of the corrected total cell fluorescence in the hearts of all injected Ai9 mice. FIG. 23D shows a graph of the corrected total cell fluorescence in the hearts of all injected female Ai9 mice. FIG. 23E shows a graph of the corrected total cell fluorescence in the livers of all injected male Ai9 mice. FIG. 23F shows a graph of the corrected total cell fluorescence in the hearts of all injected male Ai9 mice. P-value*<0.05; ns=not significant FIG. 24A shows a graph of PCR band intensity (relative to a mock, unedited band) for a PCR band resulting from PCR editing assay of liver tissues from Ai9 mice injected with either an AAV9 vector or an AAV.cc47 vector. FIG. 24B shows a graph of PCR band intensity (relative to a mock, unedited band) for a PCR band resulting from PCR editing assay of heart tissues from Ai9 mice injected with either an AAV9 vector or an AAV.cc47 vector.

FIG. 25A shows a graph of the percentage of gene editing efficiency of liver tissues from Ai9 mice injected with either an AAV9 vector or an AAV.cc47 vector. FIG. 25B shows a graph of the percentage of gene editing efficiency of heart tissues from Ai9 mice injected with either an AAV9 vector or an AAV.cc47 vector.

FIG. 26A shows representative fluorescent microscopy images showing mCherry expression in heart vibratome sections 24 hours post-fixation with 4% PFA in mice infected with AAV9 or AAV.cc44. FIG. 26B shows a graph depicting corrected total cell fluorescence of a series of multiple images.

FIG. 26C shows representative fluorescent microscopy images showing mCherry expression in skeletal muscle vibratome sections 24 hours post-fixation with 4% PFA in mice infected with AAV9 or AAV.cc44. FIG. 26D shows a graph depicting corrected total cell fluorescence of a series of multiple images.

FIG. 27A shows representative fluorescent microscopy images showing mCherry expression in liver vibratome sections 24 hours post-fixation with 4% PFA in mice infected with AAV9 or AAV.cc44. FIG. 27B shows a graph depicting corrected total cell fluorescence of a series of multiple images.

FIG. 27C shows representative fluorescent microscopy images showing mCherry expression in kidney vibratome sections 24 hours post-fixation with 4% PFA in mice infected with AAV9 or AAV.cc44. FIG. 27D shows a graph depicting corrected total cell fluorescence of a series of multiple images.

FIGS. 28A-28C illustrate fluorescence reporter expression as assessed by immunohistochemistry (IHC) in C57/B6 mouse brain regions in accordance with certain embodiments herein. FIG. 28A depicts brain regions from a mouse that was sham infected whereas FIG. 28B depicts brain regions from a mouse that was infected with AAV9 vectors, and FIG. 28C depicts brain regions from a mouse that was infected with AAV.cc44. Brain regions shown include: Ctx=cerebral cortex; Hc=hippocampus; Cb=cerebellum; Th=thalamus; Str=striatum; and mb=mushroom body.

FIG. 29A depicts a full capsid with the variable region 4 (VR4) on the capsid surface highlighted (top panel) and the recombinant capsid proteins produced as vectors packaging CBh-mCherry (AAV.cc47 and AAV.cc44) (bottom panel). FIG. 29B depicts a full capsid with the variable region 8 (VR8) on the capsid surface highlighted (top panel) and the recombinant capsid proteins produced as vectors packaging CBh-eGFP (AAV.cc81 and AAV.cc84) (bottom panel).

FIGS. 30A-30F illustrate representative images of mCherry or eGFP expressed in mouse brain upon intracerebroventricular (ICV) injection of AAV vectors in accordance with certain embodiments herein. FIG. 30A depicts a whole mouse brain after ICV injection of the AAV9 vector (mCherry) and selected brain regions. FIG. 30B depicts a whole mouse brain after ICV injection of the AAV.cc44 vector (mCherry) and selected brain regions. FIG. 30C depicts a whole mouse brain after ICV injection of the AAV.cc47 vector (mCherry) and selected brain regions. FIG. 30D depicts a whole mouse brain after ICV injection of the AAV9 vector (eGFP) and selected brain regions. FIG. 30E depicts a whole mouse brain after ICV injection of the AAV.cc81 vector (eGFP) and selected brain regions. FIG. 30F depicts a whole mouse brain after ICV injection of the AAV.cc84 vector (eGFP) and selected brain regions. Brain regions shown include: Ctx=cerebral cortex; Hc=hippocampus; and Cb=cerebellum.

FIG. 31A depicts images from selected brain regions after immunofluorescence (IF) staining for DAPI, eGFP, and NeurN in brain tissues harvested and processed after ICV injection of the AAV9 vector (eGFP). Images from all three stainings were merged to show colocalization. FIG. 31B depicts images from selected brain regions after immunofluorescence (IF) staining for DAPI, eGFP, and NeurN in brain tissues harvested and processed after ICV injection of the AAV.cc84 vector (eGFP). Images from all three stainings were merged to show colocalization. The number of neurons having both eGFP and NeurN staining was quantified in the cerebellum (CB, FIG. 31C), hippocampus (HC, FIG. 31D), and cerebral cortex (CTX, FIG. 31E).

FIG. 32A depicts images from selected brain regions after immunofluorescence (IF) staining for DAPI, mCherry, and NeurN in brain tissues harvested and processed after ICV injection of the AAV9 vector (mCherry). Images from all three stainings were merged to show colocalization. FIG. 32B depicts images from selected brain regions after immunofluorescence (IF) staining for DAPI, eGFP, and NeurN in brain tissues harvested and processed after ICV injection of the AAV.cc47 vector (mCherry). Images from all three stainings were merged to show colocalization. The number of neurons having both mCherry and NeurN staining was quantified in the in the cerebellum (CB, FIG. 32C), hippocampus (HC, FIG. 32D), and cerebral cortex (CTX, FIG. 32E).

DETAILED DESCRIPTION

Figure 1A:
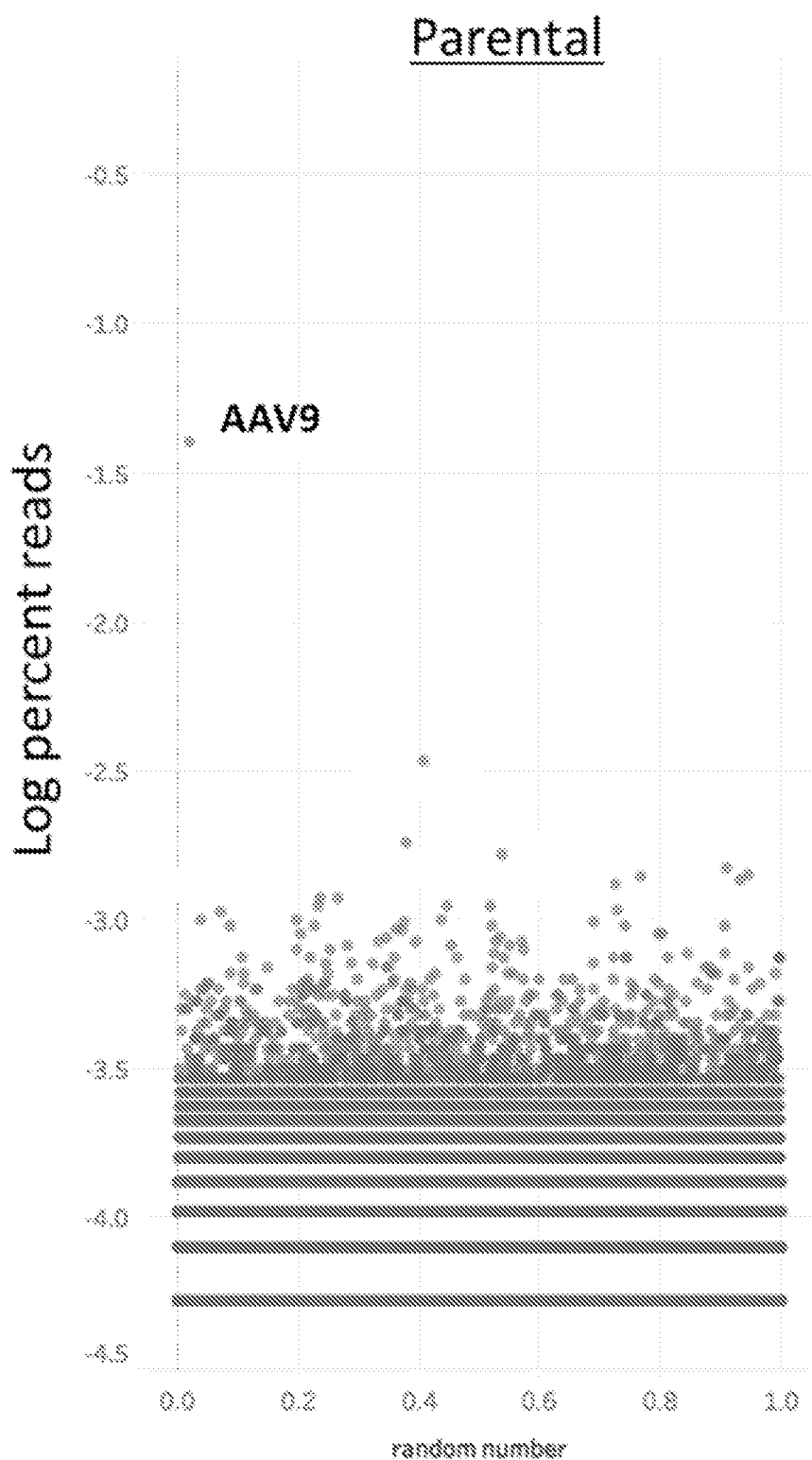
FIGS. 1A-1B illustrate bubble plots showing analysis of library diversity, directed evolution and enrichment of AAVs comprising capsid proteins with novel peptide substitutions in accordance with certain embodiments herein. Parental (FIG. 1A) and evolved libraries from three cycles (FIG. 1B) were subjected to high-throughput sequencing using the Illumina MiSeq platform. Following analysis with a custom Perl script, enriched amino acid sequences were plotted. Each bubble represents a distinct capsid protein amino acid sequence with the radius of the bubble proportional to the number of reads for that variant in the respective library. The y-axis represents the percentage of total reads from the sequencing run. Data are spread along the x-axis for ease of visualization. The percent reduction in unique clones (96.5%) directly demonstrates that numerous "un-fit" sequences were removed after a first and/or second round of evolution. Dominant isolates were selected for further analysis.
Figure 1B:
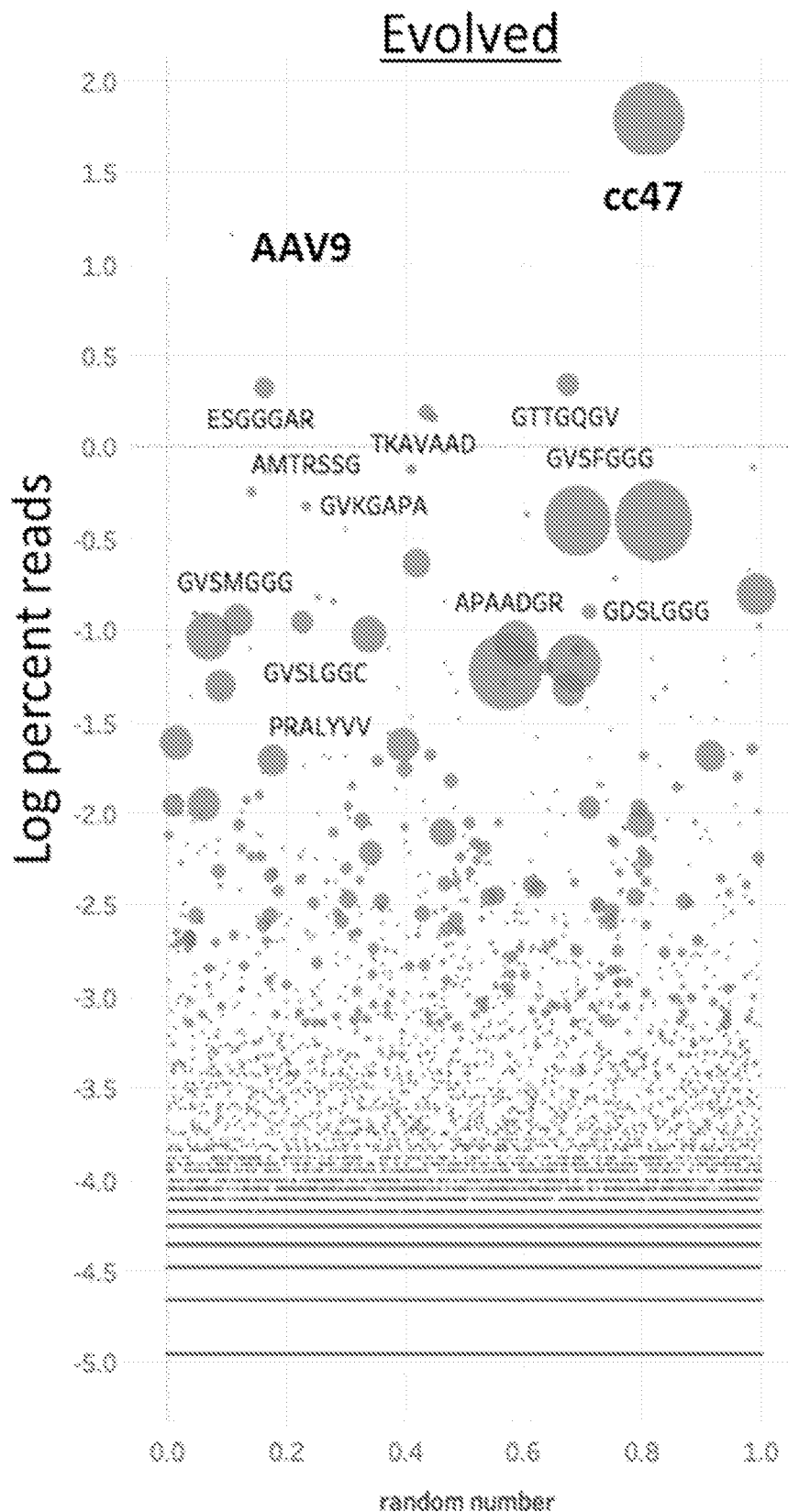

Adeno-associated virus (AAV) vectors have become a leading platform for therapeutic gene delivery. Unfortunately, AAV-based gene therapies are sometimes be less effective than desired because of, for example, difficulties in optimizing administration routes to target a cell or tissue of interest and the subject's immune responses against the vector carrying the therapeutic gene (e.g., a transgene of interest). Host-derived pre-existing antibodies generated upon natural encounter of AAV or recombinant AAV vectors prevent first time as well as repeat administration of AAV vectors as vaccines and/or for gene therapy. Serological studies reveal a high prevalence of antibodies in the human population worldwide with about 67% of people having antibodies against AAV1, 72% against AAV2, and about 40% against AAV5 through AAV9. In gene therapy, pre-existing antibodies in the subject cause problems because certain clinical scenarios involving gene silencing or tissue degeneration require multiple AAV vector administrations to sustain long term expression of the transgene.

Known AAV serotypes each have a specific tissue tropism, and there are some tissues (e.g., kidney) that cannot be easily targeted using these AAVs. Delivery of therapeutic genes using AAV vectors for treating disorders of the central nervous systems (CNS) and peripheral nervous systems (PNS) is particularly difficult as the blood brain barrier can impede access of AAV-based therapies from reaching the desired target. AAV transduction in systemic organs such as the heart, liver or lung can vary significantly for a given dose in various model organisms used during clinical development (e.g., canine, pig, non-human primates) and in human subjects.

To circumvent these issues, recombinant AAV vectors which evade antibody recognition and/or selectively target tissues of the CNS are needed. Aspects provided in the present disclosure will help a) expand the eligible cohort of patients suitable for AAV-based gene therapy and b) allow multiple, repeat administrations of AAV-based gene therapy vectors. Additionally, there is a need to develop AAV-based gene therapies that are able to selectively and specifically target tissues of interest, including tissues that are have been difficult to target using known AAV serotypes such as the kidney.

The present disclosure is based, at least in part, on the novel discovery that capsid antigenicity and functional properties of AAV capsids and capsid proteins, such as tropism and transduction, overlap in a structural context and can be modified to impart improved functionality. Based on the present disclosure, AAV capsid proteins disclosed herein and adeno-associated virus (AAV) vectors comprising the AAV capsid proteins may be coevolved to induce cross-species compatibility, which is a potentially useful trait that enables reliable translation of the use of a given AAV from non-human models of disease (e.g., rodent, non-human primates) to humans. Accordingly, the present disclosure provides cross-species compatible AAV capsid proteins and AAV vectors comprising AAV capsid proteins herein, methods of making, and methods of use thereof. As used herein, "cross-species compatible AAVs" can refer to AAV vectors comprising an AAV capsid protein variant having a mutated and/or substituted amino acid sequence which is coevolved for cross-species compatibility.

I. Definitions

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

As used in the specification, articles "a" and "an" are used herein to refer to one or to more than one (i.e., at least one) of the grammatical object of the article. By way of example, "an element" means at least one element and can comprise more than one element.

"About" is used to provide flexibility to a numerical range endpoint by providing that a given value may be "slightly above" or "slightly below" the endpoint without affecting the desired result. The term "about" in association with a numerical value means that the numerical value can vary plus or minus by 5% or less of the numerical value.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used herein, "and/or" refers to and encompasses any and all possible combinations of one or more of the associated listed items, as well as the lack of combinations where interpreted in the alternative ("or").

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, avian AAV, bovine AAV, canine AAV, equine AAV, ovine AAV, and any other AAV now known or later discovered. See, e.g., BERNARD N. FIELDS et al., VIROLOGY, volume 2, chapter 69 (4th ed., Lippincott-Raven Publishers). A number of AAV serotypes and clades have been identified (see, e.g., Gao et al, (2004) J. Virology 78:6381-6388; Moris et al, (2004) Virology 33-:375-383; and Table 1).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC 001358, NC 001540, AF513851, AF513852, AY530579; the disclosures of which are incorporated by reference herein for teaching parvovirus and AAV nucleic acid and amino acid sequences. Also see Table 1.

TABLE 1

|  | GenBank Accession Number |  | GenBank Accession Number |  | GenBank Accession Number |
| --- | --- | --- | --- | --- | --- |
| Complete Genomes |  | Clade C |  | Rh57 | AY530569 |
| Adeno-associated virus 1 | NC_00207, AF063497 | Hu9 | AY530629 | Rh50 | AY530563 |
| Adeno-associated virus 2 | NC 001401 | Hu10 | AY530576 | Rh49 | AY530562 |
| Adeno-associated virus 3 | NC 001729 | Hu11 | AY530577 | Hu39 | AY530601 |
| Adeno-associated virus 3B | NC 001863 | Hu53 | AY530615 | Rh58 | AY530570 |
| Adeno-associated virus 4 | NC 001829 | Hu55 | AY530617 | Rh61 | AY530572 |
| Adeno-associated virus 5 | Y18065, AF085716 | Hu54 | AY530616 | Rh52 | AY530565 |
| Adeno-associated virus 6 | NC 001862 | Hu7 | AY530628 | Rh53 | AY530566 |
| Avian AAV ATCC VR-865 | AY186198, AY629583, NC 004828 | Hu18 | AY530583 | Rh51 | AY530564 |
| Avian AAV strain DA-1 | NC_006263, AY629583 | Hu15 | AY530580 | Rh64 | AY530574 |

TABLE 1-continued

| | GenBank Accession Number | | GenBank Accession Number | | GenBank Accession Number |
|---|---|---|---|---|---|
| Bovine AAV | NC_005889, AY388617, AAR26465 | Hu16 | AY530581 | Rh43 | AY530560 |
| AAV11 | AAT46339, AY631966 | Hu25 | AY530591 | AAV8 | AF513852 |
| AAV12 | AB116639, DQ813647 | Hu60 | AY530622 | Rh8 | AY242997 |
| Clade A | | Ch5 | AY243021 | Rh1 | AY530556 |
| AAV1 | NC_002077, AF063497 | Hu3 | AY530595 | Clade F | |
| AAV6 | NC_001862 | Hu1 | AY530575 | Hu14 (AAV9) | AY530579 |
| Hu. 48 | AY530611 | Hu4 | AY530602 | Hu31 | AY530596 |
| Hu 43 | AY530606 | Hu2 | AY530585 | Hu32 | AY530597 |
| Hu 44 | AY530607 | Hu61 | AY530623 | HSC1 | M1332400.1 |
| Hu 46 | AY530609 | Clade D | | HSC2 | M1332401.1 |
| Clade B | | Rh62 | AY530573 | HSC3 | M1332402.1 |
| Hu. 19 | AY530584 | Rh48 | AY530561 | HSC4 | M1332403.1 |
| Hu. 20 | AY530586 | Rh54 | AY530567 | HSC5 | M1332405.1 |
| Hu 23 | AY530589 | Rh55 | AY530568 | HSC6 | M1332404.1 |
| Hu22 | AY530588 | Cy2 | AY243020 | HSC7 | M1332407.1 |
| Hu24 | AY530590 | AAV7 | AF513851 | HSC8 | M1332408.1 |
| Hu21 | AY530587 | Rh35 | AY243000 | HSC9 | M1332409.1 |
| Hu27 | AY530592 | Rh37 | AY242998 | HSC11 | M1332406.1 |
| Hu28 | AY530593 | Rh36 | AY242999 | HSC12 | M1332410.1 |
| Hu 29 | AY530594 | Cy6 | AY243016 | HSC13 | M1332411.1 |
| Hu63 | AY530624 | Cy4 | AY243018 | HSC14 | M1332412.1 |
| Hu64 | AY530625 | Cy3 | AY243019 | HSC15 | M1332413.1 |
| Hu13 | AY530578 | Cy5 | AY243017 | HSC16 | M1332414.1 |
| Hu56 | AY530618 | Rh13 | AY243013 | HSC17 | M1332415.1 |
| Hu57 | AY530619 | Clade E | | Hu68 | |
| Hu49 | AY530612 | Rh38 | AY530558 | Clonal Isolate | |
| Hu58 | AY530620 | Hu66 | AY530626 | AAV5 | Y18065, AF085716 |
| Hu34 | AY530598 | Hu42 | AY530605 | AAV 3 | NC_001729 |
| Hu35 | AY530599 | Hu67 | AY530627 | AAV 3B | NC_001863 |
| AAV2 | NC_001401 | Hu40 | AY530603 | AAV4 | NC_001829 |
| Hu45 | AY530608 | Hu41 | AY530604 | Rh34 | AY243001 |
| Hu47 | AY530610 | Hu37 | AY530600 | Rh33 | AY243002 |
| Hu51 | AY530613 | Hu40 | AY530559 | Rh32 | AY243003 |
| Hu52 | AY530614 | Rh2 | AY243007 | Others | |
| Hu T41 | AY695378 | Bb1 | AY243023 | Rh74 | |
| Hu S17 | AY695376 | Bb2 | AY243022 | Bearded Dragon AAV | |
| Hu T88 | AY695375 | Rh10 | AY243015 | Snake AAV | NC_006148.1 |
| Hu T71 | AY695374 | Hu17 | AY530582 | | |
| Hu T70 | AY695373 | Hu6 | AY530621 | | |
| Hu T40 | AY695372 | Rh25 | AY530557 | | |
| Hu T32 | AY695371 | Pi2 | AY530554 | | |
| Hu T17 | AY695370 | Pi1 | AY530553 | | |
| Hu LG15 | AY695377 | Pi3 | AY530555 | | |

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

A "polynucleotide" as used herein refers to a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, the term "peptide" refers to a short amino acid sequence. The term peptide may be used to refer to portion or region of an AAV capsid amino acid sequence. The peptide may be a peptide that naturally occurs in a native AAV capsid, or a peptide that does not naturally occur in a native AAV capsid. Naturally occurring AAV peptides in an AAV capsid may be substituted by non-naturally occurring peptides. For example, a non-naturally occurring peptide may be substituted into an AAV capsid to provide a modified capsid, such that the naturally-occurring peptide is replaced by the non-naturally occurring peptide. As used herein, the term "polypeptide" encompasses both peptides and proteins, unless indicated otherwise.

As used herein, the term "amino acid" encompasses any naturally occurring amino acid, modified forms thereof, and synthetic amino acids. Alternatively, an amino acid herein can be a modified amino acid residue and/or can be an amino acid that is modified by post-translation modification (e.g., acetylation, amidation, formylation, hydroxylation, methylation, phosphorylation or sulfatation). Naturally occurring, levorotatory (L-) amino acids are shown in Table 2.

TABLE 2

| Amino Acid Residue | Three-Letter Code | One-Letter Code |
| --- | --- | --- |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) and/or can be an amino acid that is modified by post-translation modification (e.g., acetylation, amidation, formylation, hydroxylation, methylation, phosphorylation or sulfatation).

TABLE 3

| Modified Amino Acid Residue | Abbreviation |
| --- | --- |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | alle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |

TABLE 3-continued

| Modified Amino Acid Residue | Abbreviation |
| --- | --- |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., *Annu Rev Biophys Biomol Struct.* 35:225-49 (2006). These unnatural amino acids can advantageously be used to chemically link molecules of interest to the AAV capsid protein.

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" as used herein is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka, (1992) *Curr. Topics Microbiol. Immunol.* 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one TR sequence (e.g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11, 12, 13 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

An AAV vector typically comprises a protein-based capsid, and a nucleic acid encapsidated by the capsid. The nucleic acid may be, for example, a vector genome comprising a transgene flanked by inverted terminal repeats. The AAV "capsid" is a near-spherical protein shell that comprises individual "capsid proteins" or "subunits." AAV capsids typically comprise about 60 capsid protein subunits, associated and arranged with T=1 icosahedral symmetry. When an AAV vector is described herein as comprising an AAV capsid protein, it will be understood that the AAV vector comprises a capsid, wherein the capsid comprises one or more AAV capsid proteins (i.e., subunits). Also described herein are "viral-like particles" or "virus-like particles," which refers to a capsid that does not comprise any vector genome or nucleic acid comprising a transgene.

The virus vectors of the present disclosure can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al., (2000) *Molecular Therapy* 2:619.

The virus vectors of the present disclosure can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention. Further, the viral capsid or genomic elements can contain other modifications, including insertions, deletions and/or substitutions.

The term "self-complimentary AAV" or "scAAV" refers to a recombinant AAV vector which forms a dimeric inverted repeat DNA molecule that spontaneously anneals, resulting in earlier and more robust transgene expression compared with conventional single-strand (ss) AAV genomes. See, e.g., McCarty, D. M., et al., Gene Therapy 8, 1248-1254 (2001). Unlike conventional ssAAV, scAAV can bypass second-strand synthesis, the rate-limiting step for gene expression. Moreover, double-stranded scAAV is less prone to DNA degradation after viral transduction, thereby increasing the number of copies of stable episomes. Notably, scAAV can typically only hold a genome that is about 2.4 kb, half the size of a conventional AAV vector. In some embodiments, the AAV vectors described herein are self-complementary AAVs.

A "therapeutic polypeptide" or "therapeutic protein" is a polypeptide or protein that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human. In other embodiments, the subject comprises a human in need of one or more gene therapies.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

Unless otherwise defined, all technical terms used herein have the same meaning as commonly understood by one of ordinary skill in the art to which this disclosure belongs.

II. Cross-Species Compatible AAVs

Adeno-associated virus (AAV), a member of the Parvovirus family, is a small, non-enveloped virus. Wildtype AAV is composed of an icosahedral protein capsid which encloses a single-stranded DNA genome. In wildtype AAVs, inverted terminal repeats (ITRs) flank the coding nucleotide sequences (e.g., a polynucleotides) for the non-structural proteins (encoded by Rep genes) and the structural proteins (encoded by capsid genes or Cap genes). Rep genes encode the non-structural proteins that regulate functions comprising the replication of the AAV genome. Cap genes encode the structural proteins, VP1, VP2 and/or VP3 that assemble to form the capsid.

The present disclosure provides recombinant AAV capsid proteins (VP1, VP2 and/or VP3) comprising a modification (e.g., a substitution) in the amino acid sequence relative to a wildtype capsid proteins, and AAV capsids and AAV vectors comprising the modified AAV capsid protein. The inventors have discovered that modifications of disclosed herein can confer one or more desirable properties to virus vectors comprising the modified AAV capsid protein variants herein, including without limitation, the ability to evade neutralizing antibodies and/or the ability to specifically and selectively target a cell or tissue of interest. Thus, the present disclosure addresses some of the limitations associated with conventional AAV vectors.

In certain embodiments, AAV vectors herein may be engineered to include one or more capsid protein variants. In some embodiments, AAV vectors herein may be cross-species compatible vectors, or "ccAAVs." In some embodiments, AAV vectors (e.g., ccAAVs) may be engineered to include at least one or more amino acid substitutions, wherein the one or more substitutions may modify one or more antigenic sites on the AAV capsid protein. The modification of the one or more antigenic sites may result in inhibition of binding by an antibody to the one or more antigenic sites and/or inhibition of neutralization of infectivity of a virus particle comprising said a capsid protein variant herein.

Accordingly, in some embodiments herein, the present disclosure provides an adeno-associated virus (AAV) capsid protein variant, comprising one or more amino acid modifications (e.g., substitutions and/or deletions), wherein the one or more modifications modify one or more antigenic sites on the AAV capsid protein. In some embodiments, modification of the one or more antigenic sites can result in inhibition of binding by an antibody to the one or more antigenic sites and/or inhibition of neutralization of infectivity of a virus particle comprising said AAV capsid protein. In some embodiments, the modified antigenic site can prevent antibodies from binding or recognizing or neutralizing AAV capsids. In some embodiments, the antibody can be an IgG (including IgG1, IgG2a, IgG2b, IgG3), IgM, IgE or IgA. In some embodiments, the modified antigenic site can prevent binding, recognition, or neutralization of AAV capsids by antibodies from different animal species, wherein the animal is human, canine, porcine, bovine, non-human primate, rodent, feline or equine.

In some embodiments, modification of the one or more antigenic sites can result in tropism of the AAV vectors (e.g., ccAAVs) herein to one or more cell types, one or more tissue types, or any combination thereof. As used herein, "tropism" refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest. In some embodiments, modification of the one or more antigenic sites can result in AAV vectors herein that may exhibit tropism for one or more cell types and/or tissues throughout the body of a subject. In some aspects, modification of the one or more antigenic sites can result in AAV vectors herein that may exhibit tropism to brain tissues, lung tissues, skeletal muscle tissues, heart tissues, liver tissues, kidney tissues, and/or pancreas tissues. In some aspects, modification of the one or more antigenic sites can result in AAV vectors herein that may exhibit tropism to one or more brain cells, one or more lung cells, one or more skeletal muscle cells, one or more heart cells, one or more liver cells, one or more kidney cells, and/or one or more pancreas cells. In some aspects, modification of the one or more antigenic sites can result in AAV vectors herein that may exhibit tropism to the kidney.

In some embodiments, the one or more amino acid modifications (e.g., substitutions and/or deletions) within capsid protein variants herein, can be in one or more antigenic footprints identified by peptide epitope mapping and/or cryo-electron microscopy studies of AAV-antibody complexes containing AAV capsid proteins. In some embodiments, the one or more antigenic sites herein that can be subject to one or more amino acid modifications may be common antigenic motifs (CAMs) as described in WO 2017/058892, which is incorporated herein by reference in its entirety.

In some embodiments, the one or more antigenic sites herein that can be subject to one or more amino acid modifications may be in a variable region (VR) of an AAV capsid protein. An AAV capsid contains 60 copies (in total) of three VPs (VP1, VP2, VP3) that are encoded by the cap gene and have overlapping sequences. Each VP can contain an eight-stranded β-barrel motif (βB to βI) and/or an α-helix (αA) conserved in autonomous parvovirus capsids. Structurally variable regions (VRs) may occur in the surface loops that connect the β-strands, which cluster to produce local variations in the capsid surface. In some embodiments, the one or more amino acid modifications herein that modify one or more antigenic sites in AAV capsid protein variants herein may be in VR-I, VR-II, VR-III, VR-IV, VR-V, VR-VI, VR-VII, VR-VI II, VR-IX, or any combination thereof. In some embodiments, one or more antigenic sites may be in the HI loop of the AAV capsid protein variants herein.

In some embodiments, AAV vectors herein (e.g., ccAAVs) may comprise (i) a AAV capsid protein variant disclosed herein, and (ii) a cargo nucleic acid encapsidated by the capsid protein. In accordance with these embodiments, an AAV vector (e.g., ccAAV) comprising an AAV capsid protein variant described herein may have a phenotype of: evading neutralizing antibodies; enhanced or maintained transduction efficiency; selective tropism to one or more cell and/or tissue types; and any combination thereof.

In some embodiments, the AAV vectors disclosed herein exhibit at least about 2-fold (for example, about 4-fold, about 5-fold, about 7-fold, about 10-fold, about 15-fold, about 16-fold, about 17-fold, about 18-fold, about 20-fold, about 25-fold, or about 30-fold, including all values and subranges that lie therebetween) higher transduction in heart, skeletal muscle, kidney, and brain neurons, compared to parental AAV9. In some embodiments, the AAV vectors disclosed herein exhibit higher transduction efficiency than parental AAV9 in some tissue types (such as, for example, heart, skeletal muscle, kidney, brain neurons), and similar or decreased transduction efficiency relative to the parental AAV9 in some tissue types (such as, glial cells).

The disclosure provides AAVcc.47, which demonstrated about 15-fold to about 18-fold higher transduction in heart, skeletal muscle, kidney, compared to parental AAV9. Transduction of AAVcc.47 in neurons was higher in the brain compared to AAV9, while glial cell transduction remained relatively unaltered. AAVcc.81 and AAVcc.84 increased transduction by 4-fold in heart and skeletal muscle, while no significant increase in liver transduction was observed for either ccAAV compared to AAV9. Transduction of glial cells significantly decreased with ccAAVs compared to AAV9, while neuronal tropism slightly increased. Increase in transduction efficiency by ccAAVs may afford lower dosing regiments of therapeutic vectors.

In some embodiments, AAV capsid protein variants disclosed herein may include at least one or more amino acid substitutions wherein about 1 amino acid residue to about 50 amino acid residues (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) may be substituted from the amino acid residues comprising an amino acid sequence of a naturally occurring capsid protein. In accordance with some embodiments herein, AAV capsid protein variants herein may have about 7 amino acid residues substituted from the amino acid residues comprising an amino acid sequence of a naturally occurring capsid protein.

In some embodiments, AAV capsid protein variants disclosed herein may have an amino acid sequence with about 85% (e.g., about 85%, 90%, 95%, 99%, 100%) similarity to a naturally occurring capsid protein. As used herein, "naturally occurring" or "wild-type" means existing in nature without modification by man. In some embodiments, a naturally occurring capsid protein herein can be derived from a single species. Non-limiting examples of species that may be the origin of a naturally occurring capsid protein herein include those from a general organism such as a human, mouse, rat, guinea pig, dog, cat, horse, cow, pig, or non-human primate (e.g., monkey, chimpanzee, baboon, gorilla) bird, reptile, worm, fish, and the like. In some embodiments, species that may be the origin of a naturally occurring capsid protein herein may be *Mus Musculus* (mouse), *Sus scrofa* (pig), *Canis Familiaris* (Dog), Non-human primates (*Macaca*, macaque), *Homo sapiens* (human), and any combination thereof. In some embodiments, AAV capsid protein variants having at least one amino acid substitution as disclosed herein may have an amino acid sequence with about 85% (e.g., about 85%, 90%, 95%, 99%, 100%) similarity to a naturally occurring capsid protein having an amino acid sequence referenced by GenBank Accession Numbers: NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579, and any combination thereof.

Methods of determining sequence similarity or identity between two or more amino acid sequences are known in the art. Sequence similarity or identity may be determined using standard techniques, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection. Another suitable algorithm is the BLAST algorithm, described in Altschul et al., *J Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., Methods in Enzymology, 266, 460-480 (1996). WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity. Further, an additional useful algorithm is gapped BLAST as reported by Altschul et al, (1997) Nucleic Acids Res. 25, 3389-3402. For purposes of the instant disclosure, unless otherwise indicated, percent identity is calculated using the Basic Local Alignment Search Tool (BLAST) available online at blast.ncbi.nlm.nih.gov/Blast.cgi. The skilled artisan will understand that other algorithms may be substituted as appropriate.

In some embodiments, AAV capsid protein variants disclosed herein may have at least amino acid substitution that can replace any seven amino acids in an AAV capsid protein from any one of the following serotypes: AAV1, AAV2, AAV3, AAV4, AAV5, AAV6, AAV7, AAV8, AAV9, AAVrh8, AAVrh10, AAV10, AAV11, AAV12, AAVrh32.22, bovine AAV, avian AAV and/or any other AAV now known or later identified. In some embodiments, AAV capsid protein variants disclosed herein may have at least one amino acid substitution that can replace any seven amino acids in an AAV capsid protein from a serotype having a known tropism to one or more desired cell and/or tissue types. In some embodiments, AAV capsid protein variants disclosed herein may have at least one amino acid substitution that can replace any seven amino acids in an AAV capsid protein from a serotype having a known tropism to one or more desired human cell and/or tissue types.

In accordance these embodiments, AAV capsid protein variants disclosed herein may have at least one amino acid substitution that can replace any seven amino acids in an AAV capsid protein from a serotype having tropism for CNS and/or PNS. AAVs can target a number of different tissue types and cell types successfully within the CNS and PNS including but not limited to neurons, astrocytes, oligodendrocytes, microglia, Müller glia, Schwann cells, and satellite cells. In some examples, AAV capsid protein variants disclosed herein may have at least one amino acid substitution that can replace any seven amino acids in an AAV capsid protein of any AAV serotype having tropism for astrocytes (e.g., AAV1, AAV2, AAV4, AAV5, AAV6, AAV7, AAV8, AAV9). In some other examples, AAV capsid protein variants disclosed herein may have at least one amino acid substitution that can replace any seven amino acids in an AAV capsid protein of any AAV serotype having tropism for oligodendrocytes (e.g., AAV8, AAV9). In some examples, AAV capsid protein variants disclosed herein may have at least one amino acid substitution that can replace any seven amino acids in an AAV capsid protein of any AAV serotype having tropism for microglia (e.g., AAV2, AAV5, AAV6, AAV8, AAV9). In some other examples, AAV capsid protein variants disclosed herein may have at least one amino acid substitution that can replace any seven amino acids in an AAV capsid protein of any AAV serotype having tropism for Müller glia (e.g., AAV1, AAV2, AAV4, AAV6, AAV8, AAV9). In some examples, AAV capsid protein variants disclosed herein may have at least one amino acid substitution that can replace any seven amino acids in an AAV capsid protein of any AAV serotype having tropism for Schwann cells/satellite glia (e.g., AAV1, AAV2, AAV5, AAV6, AAV7, AAV8, AAV9).

In some embodiments, AAV capsid protein variants herein or fragments thereof may have an amino acid sequence with about 85% (e.g., about 85%, 90%, 95%, 99%, 100%) similarity to a naturally occurring VP1 capsid protein or fragment thereof. In some embodiments, capsid protein variants herein can comprise an amino acid substitution at one or more (e.g., 2, 3, 4, 5, 6, or 7) of amino acid residues 262-268 of AAV1 (VP1 numbering), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues 370-379 of AAV1 (VP1 numbering), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues 451-459 of AAV1 (VP1 numbering), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues 472-473 of AAV1 (VP1 numbering) or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues 493-500 of AAV1 (VP1 numbering), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues 528-534 of AAV1 (VP1 numbering), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues 547-552 of AAV1 (VP1 numbering), in any combination, or the equivalent amino acid residues in AAV2, AAV3, AAV4, AAV5, AAV6, AAV7, AAV8, AAV9, AAV10, AAV1, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues 588-597 of AAV1 (VP1 numbering) in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2) of amino acid residues 709-710 of AAV1 (VP1 numbering), or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues 716-722 of AAV1 (VP1 numbering) in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, capsid protein variants herein can comprise an amino acid substitution at one or more (e.g., 2, 3, 4, 5, 6, or 7) of amino acid residues 262-268 of AAV1 (VP1 numbering); at one or more (e.g., 2, 3, 4, 5, 6, or 7) of amino acid residues 370-379 of AAV1 (VP1 numbering); at one or more (e.g., 2, 3, 4, 5, 6, or 7) of amino acid residues 451-459 of AAV1 (VP1 numbering); an amino acid substitution at one or more (e.g., 2, 3, 4, 5, 6, or 7) of amino acid residues 472-473 of AAV1 (VP1 numbering); at one or more (e.g., 2, 3, 4, 5, 6, or 7) of amino acid residues 493-500 of AAV1 (VP1 numbering); at one or more (e.g., 2, 3, 4, 5, 6, or 7) of amino acid residues 528-534 of AAV1 (VP1 numbering); at one or more (e.g., 2, 3, 4, 5, 6, or 7) of amino acid residues 547-552 of AAV1 (VP1 numbering); at one or more (e.g., 2, 3, 4, 5, 6, or 7) of amino acid residues 588-597 of AAV1 (VP1 numbering); at one or more (e.g., 2) of amino acid residues 709-710 of AAV1 (VP1 numbering); at one or more (e.g., 2, 3, 4, 5, 6, or 7) of amino acid residues 716-722 of AAV1 (VP1 numbering); or any combination thereof in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, capsid protein variants herein can comprise an amino acid substitution at one or more (e.g., 2, 3, 4, 5, 6, or 7) of amino acid residues within a variable loop region IV (VR4) on the capsid surface of AAV1 in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues within a variable loop region VIII (VR8) on the capsid surface of AAV1 in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues within a variable loop region IV (VR4) on the capsid surface of AAV1 in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV, and an amino acid substitution at one or more (e.g., 2, 3, 4, 5, 6, or 7) of amino acid residues within a variable loop region VIII (VR8) on the capsid surface of AAV1 in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV In some embodiments, capsid protein variants herein can have at least 90% (e.g., about 90%, 95%, 99%, 100%) sequence identity to the native sequence of the AAV9 capsid (SEQ ID NO: 1). In some embodiments, capsid protein variants herein can comprise an amino acid substitution at one or more (e.g., 2, 3, 4, 5, 6, or 7) of amino acid residues within a variable loop region IV (VR4) on the capsid surface of AAV9 in any combination. In some embodiments, capsid protein variants herein can comprise an amino acid substitution at one or more (e.g., 2, 3, 4, 5, 6, or 7) of amino acid residues within a VR4 (452-NGSGQNQ-458 (VP1 numbering; SEQ ID NO: 38)) on the capsid surface of AAV1 in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise a substitution at one or more (e.g., 2, 3, 4, 5, 6, or 7) of amino acid residues within a VR4 (452-NGSGQNQ-458 (VP1 numbering; SEQ ID NO: 38)) on the capsid surface of AAV9 in any combination.

In some embodiments, capsid protein variants herein can comprise an amino acid substitution at one or more (e.g., 2, 3, 4, 5, 6, or 7) of amino acid residues within a variable loop region VIII (VR8) on the capsid surface of AAV9 in any combination. In some embodiments, capsid protein variants herein can comprise an amino acid substitution at one or more (e.g., 2, 3, 4, 5, 6, or 7) of amino acid residues within a VR8 (586-SAQAQAQ-592 (VP1 numbering); SEQ ID NO: 39) on the capsid surface of AAV1 in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise an amino acid substitution at one or more (e.g., 2, 3, 4, 5, 6, or 7) of amino acid residues within a VR8 (586-SAQAQAQ-592 (VP1 numbering; SEQ ID NO: 39)) on the capsid surface of AAV9 in any combination.

In some embodiments, capsid protein variants herein can comprise an amino acid substitution at one or more (e.g., 2, 3, 4, 5, 6, or 7) of amino acid residues within a variable loop region IV (VR4) and an amino acid substitution at one or more (e.g., 2, 3, 4, 5, 6, or 7) of amino acid residues within a variable loop region VIII (VR8) on the capsid surface of AAV9 in any combination. In some embodiments, capsid protein variants herein can comprise an amino acid substitution at one or more (e.g., 2, 3, 4, 5, 6, or 7) of amino acid residues within a VR4 (452-NGSGQNQ-458 (VP1 numbering; SEQ ID NO: 38)) on the capsid surface of AAV1 in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV, and an amino acid substitution at one or more (e.g., 2, 3, 4, 5, 6, or 7) of amino acid residues within a VR8 (586-SAQAQAQ-592 (VP1 numbering; SEQ ID NO: 39)) on the capsid surface of AAV1 in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. In some embodiments, capsid protein variants herein can comprise a substitution at one or more (e.g., 2, 3, 4, 5, 6, or 7) of amino acid residues within a VR4 (452-NGSGQNQ-458 (VP1 numbering; SEQ ID NO: 38)) on the capsid surface of AAV9 in any combination, and an amino acid substitution at one or more (e.g., 2, 3, 4, 5, 6, or 7) of amino acid residues within a VR8 (586-SAQAQAQ-592 (VP1 numbering; SEQ ID NO: 39)) on the capsid surface of AAV9 in any combination.

In some embodiments, capsid protein variants herein may have an amino acid sequence with about 85% (e.g., about 85%, 90%, 95%, 99%, 100%) similarity to a naturally occurring VP2 capsid protein or fragment thereof from any one of the serotypes described herein. In some embodiments, capsid protein variants herein can comprise an amino acid substitution at one or more (e.g., 2, 3, 4, 5, 6, or 7) of amino acid residues within a naturally occurring VP2 capsid protein or fragment thereof in any combination from any one of the serotypes described herein.

In some embodiments, capsid protein variants herein may have an amino acid sequence with about 85% (e.g., about 85%, 90%, 95%, 99%, 100%) similarity to a naturally occurring VP3 capsid protein or fragment thereof from any one of the serotypes described herein. In some embodiments, capsid protein variants herein can comprise an amino acid substitution at one or more (e.g., 2, 3, 4, 5, 6, or 7) of amino acid residues within a naturally occurring VP3 capsid protein or fragment thereof in any combination from any one of the serotypes described herein.

In some embodiments, AAV vectors (e.g., ccAAVs) herein may comprise (i) a AAV9 capsid protein variant and (ii) a cargo nucleic acid encapsidated by the capsid protein. In accordance with these embodiments, AAV vectors (e.g., ccAAVs) herein may comprise (i) a AAV9 capsid protein variant and (ii) a cargo nucleic acid encapsidated by the capsid protein wherein the capsid protein comprises a peptide having the sequence $X^1$-$X^2$-$X^3$-$X^4$-$X^5$-$X^6$-$X^7$ (SEQ ID NO: 40) at amino acids 452-458 (VP1 numbering) of a native AAV capsid protein, (SEQ ID NO: 1), wherein the peptide does not occur in the native AAV9 capsid protein sequence. In some aspects, AAV vectors herein may comprise an AAV9 capsid protein variant comprising a peptide having the sequence $X^1$-$X^2$-$X^3$-$X^4$-$X^5$-$X^6$-$X^7$ (SEQ ID NO: 40) at amino acids 452-458 (VP1 numbering) of a native AAV9 capsid protein, (SEQ ID NO: 1), wherein $X^1$ can be any amino acid other than N; $X^2$ can be any amino acid other than G; $X^3$ can be any amino acid other than S; $X^4$ can be any amino acid other than G; $X^5$ can be any amino acid other than Q; $X^6$ can be any amino acid other than N; and/or $X^7$ can be any amino acid other than Q.

In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to EGGTVHA (SEQ ID NO: 20). In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to FYGTDSA (SEQ ID NO: 21). In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to HGQSASR (SEQ ID NO: 22). In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to DTPTNQA (SEQ ID NO: 23). In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to ITRQAYQ (SEQ ID NO: 24). In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to RMFKSNQ (SEQ ID NO: 25). In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to GVSLGGG (SEQ ID NO: 26). In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to KHFLQGE (SEQ ID NO: 27). In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to MGRERAG (SEQ ID NO: 28).

In some embodiments, capsid protein variants herein may share at least about 85% (e.g., about 85%, 90%, 95%, 99%, or 100%) amino acid sequence similarity with any one of the sequences set forth in SEQ ID NOs: 2-10. In accordance with some embodiments herein, capsid protein variants herein comprise any one of the sequences set forth in SEQ ID NOs: 2-10. Amino acid sequences of native AAV9 capsid protein, (SEQ ID NO: 1) and SEQ ID NOs 2-10 are provided in Table 4 below.

In some embodiments, AAV vectors (e.g., ccAAVs) herein may comprise (i) a AAV9 capsid protein variant and (ii) a cargo nucleic acid encapsidated by the capsid protein wherein the capsid protein comprises a peptide having the sequence $X^1$-$X^2$-$X^3$-$X^4$-$X^5$-$X^6$-$X^7$ (SEQ ID NO: 125) at amino acids 586-592 (VP1 numbering) of a native AAV9 capsid protein, (SEQ ID NO: 1), wherein the peptide does not occur in the native AAV9 capsid protein sequence. In some aspects, AAV vectors herein may comprise a AAV9 capsid protein variant comprising a peptide having the sequence $X^1$-$X^2$-$X^3$-$X^4$-$X^5$-$X^6$-$X^7$ (SEQ ID NO: 125) at amino acids 586-592 (VP1 numbering) of a native AAV9 capsid protein, (SEQ ID NO: 1), wherein, $X^1$ can be any amino acid other than S; $X^2$ can be any amino acid other than A; $X^3$ can be any amino acid other than Q; $X^4$ can be any amino acid other than A; $X^5$ can be any amino acid other than Q; $X^6$ can be any amino acid other than A; and/or $X^7$ can be any amino acid other than Q.

In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to LNSSVPS (SEQ ID NO: 29). In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to YMDHQVS (SEQ ID NO: 30). In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to TSDSLVS (SEQ ID NO: 31). In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to NAVGALS (SEQ ID NO: 32). In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to MPISHHE (SEQ ID NO: 33). In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to DSGARGA (SEQ ID NO: 34). In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to NVALALG (SEQ ID NO: 35). In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to GALRMGM (SEQ ID NO: 36). In some embodiments, capsid protein variants herein can comprise a peptide wherein the amino acids corresponding to amino acid position 586-592 (VP1 numbering) of a native AAV9 capsid protein, (SEQ ID NO: 1) may be substituted with amino acids corresponding to LSGEGAV (SEQ ID NO: 37).

In some embodiments, capsid protein variants herein may share at least about 85% (e.g., about 85%, 90%, 95%, 99%, or 100%) amino acid sequence similarity with any one of the sequences set forth in SEQ ID NOs: 11-19. In accordance with some embodiments herein, capsid protein variants herein comprise any one of the sequences set forth in SEQ ID NOs: 11-19. Amino acid sequences of native AAV9 capsid protein, (SEQ ID NO: 1) and SEQ ID NOs 11-19 are provided in Table 4 below.

In some embodiments, AAV vectors (e.g., ccAAVs) herein may comprise (i) a AAV9 capsid protein variant and (ii) a cargo nucleic acid encapsidated by the capsid protein wherein the capsid protein comprises a peptide having the sequence $X^1$-$X^2$-$X^3$-$X^4$-$X^5$-$X^6$-$X^7$ (SEQ ID NO: 40) at amino acid position 452-458 (VP1 numbering) and at amino acids 586-592 (VP1 numbering) of a native AAV9 capsid protein, (SEQ ID NO: 1), wherein the peptide does not occur in the native AAV9 capsid protein sequence.

In some embodiments, AAV vectors (e.g., ccAAVs) herein may comprise (i) a AAV9 capsid protein variant and (ii) a cargo nucleic acid encapsidated by the capsid protein wherein the capsid protein comprises a peptide having the sequence $X^1$-$X^2$-$X^3$-$X^4$-$X^5$-$X^6$-$X^7$ (SEQ ID NO: 125) at amino acid position 586-592 (VP1 numbering) and at amino acids 586-592 (VP1 numbering) of a native AAV9 capsid protein, (SEQ ID NO: 1), wherein the peptide does not occur in the native AAV9 capsid protein sequence.

In some aspects, AAV vectors herein may comprise an AAV9 capsid protein variant comprising a peptide having: (1) the sequence $X^1$-$X^2$-$X^3$-$X^4$-$X^5$-$X^6$-$X^7$ (SEQ ID NO: 40) at amino acids 452-458 (VP1 numbering) of a native AAV9 capsid protein, (SEQ ID NO: 1), wherein $X^1$ can be any amino acid other than N; $X^2$ can be any amino acid other than G; $X^3$ can be any amino acid other than S; $X^4$ can be any amino acid other than G; $X^5$ can be any amino acid other than Q; $X^6$ can be any amino acid other than N; and/or $X^7$ can be any amino acid other than Q; and (2) the sequence $X^1$-$X^2$-$X^3$-$X^4$-$X^5$-$X^6$-$X^7$ (SEQ ID NO: 125) at amino acids 586-592 (VP1 numbering) of a native AAV9 capsid protein, (SEQ ID NO: 1), wherein, $X^1$ can be any amino acid other than S; $X^2$ can be any amino acid other than A; $X^3$ can be any amino acid other than Q; $X^4$ can be any amino acid other than A; $X^5$ can be any amino acid other than Q; $X^6$ can be any amino acid other than A; and/or $X^7$ can be any amino acid other than Q.

In some embodiments, capsid protein variants herein can comprise a peptide wherein the amino acids corresponding to amino acid position 452-458 (VP1 numbering) of a native AAV9 capsid protein, (SEQ ID NO: 1) may be substituted with amino acids corresponding to any one of SEQ ID NOs: 20-28 and the amino acids corresponding to amino acid position 586-592 (VP1 numbering) of a native AAV9 capsid protein, (SEQ ID NO: 1) may be substituted with amino acids corresponding to any one of SEQ ID NOs: 29-37.

In some embodiments, capsid protein variants herein may share at least about 85% (e.g., about 85%, 90%, 95%, 99%, or 100%) amino acid sequence similarity with any one of the sequences set forth in SEQ ID NOs: 46-123. In accordance with some embodiments herein, capsid protein variants herein comprise any one of the sequences set forth in SEQ ID NOs: 46-123. Amino acid sequences of native AAV9 capsid protein, (SEQ ID NO: 1) and SEQ ID NOs: 46-123 are provided in Table 4 below.

TABLE 4

| SEQ ID NO | AAV9 Capsid Protein | Amino Acid Sequence |
|---|---|---|
| 1 | AAV9 WT | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTINGSGQNQQTLKFSVAGPSNMAVQGRNYIPGPSYR<br>QQRVSTTVTQNNNSEFAWPGASSWALNGRNSLMNPGPAMASHKEGEDRFFPLSGSLIFGKQGTGRDNVD<br>ADKVMITNEEEIKTTNPVATESYGQVATNHQSAQAQAQTGWVQNQGILPGMVWQDRDVYLQGPIWAKI<br>PHTDGNFHPSPLMGGFGMKHPPPQILIKNTPVPADPPTAFNKDKLNSFITQYSTGQVSVEIEWELQKENSK<br>RWNPEIQYTSNYYKSNNVEFAVNTEGVYSEPRPIGTRYLTRNL |
| 2 | AAV.cc41 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIEGGTVHAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQSAQAQAQTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 3 | AAV.cc42 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIFYGTDSAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQSAQAQAQTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 4 | AAV.cc43 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIHGQSASRQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQSAQAQAQTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 5 | AAV.cc44 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIDTPTNQAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQSAQAQAQTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 6 | AAV.cc45 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQSAQAQAQTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 7 | AAV.cc46 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF |

TABLE 4-continued

| SEQ ID NO | AAV9 Capsid Protein | Amino Acid Sequence |
|---|---|---|
|  |  | TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIRMFKSNQQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQSAQAQAQTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 8 | AAV.cc47 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIGVSLGGGQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQSAQAQAQTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 9 | AAV.cc48 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQSAQAQAQTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 10 | AAV.cc49 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 11 | AAV.cc81 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQLNSSVPSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 12 | AAV.cc82 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQYMDHQVSTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 13 | AAV.cc83 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY |

TABLE 4-continued

| SEQ ID NO | AAV9 Capsid Protein | Amino Acid Sequence |
|---|---|---|
| | | EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQTSDSLVSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 14 | AAV.cc84 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQNAVGALSTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 15 | AAV.cc85 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQMPISHHETGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 16 | AAV.cc86 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQDSGARGATGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 17 | AAV.cc87 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQNVALALGTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 18 | AAV.cc88 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQGALRMGMTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 19 | AAV.cc89 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTINGSGQNQQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQLSGEGAVTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |

TABLE 4-continued

| SEQ ID NO | AAV9 Capsid Protein | Amino Acid Sequence |
|---|---|---|
| 46 | AAV.cc41-81 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIEGGTVHAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQLNSSVPSTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 47 | AAV.cc41-82 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIEGGTVHAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQYMDHQVSTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 48 | AAV.cc41-83 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIEGGTVHAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQTSDSLVSTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 49 | AAV.cc41-84 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIEGGTVHAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQNAVGALSTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 50 | AAV.cc41-85 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIEGGTVHAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQMPISHHETGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 51 | AAV.cc41-86 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIEGGTVHAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQDSGARGATGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 52 | AAV.cc41-87 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF |

TABLE 4-continued

| SEQ ID NO | AAV9 Capsid Protein | Amino Acid Sequence |
|---|---|---|
| | | GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIEGGTVHAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNVALALGTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 53 | AAV.cc41-88 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIEGGTVHAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQGALRMGMTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 54 | AAV.cc41-89 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIEGGTVHAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLSGEGAVTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 55 | AAV.cc42-81 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIFYGTDSAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLNSSVPSTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 56 | AAV.cc42-83 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIFYGTDSAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQYMDHQVSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 57 | AAV.cc42-84 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIFYGTDSAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNAVGALSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 58 | AAV.cc42-85 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIFYGTDSAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQMPISHHETGWVQNQGILPGMVWQDRDVYLQGPIWAKIPH |

TABLE 4-continued

| SEQ ID NO | AAV9 Capsid Protein | Amino Acid Sequence |
|---|---|---|
| | | TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 59 | AAV.cc42-86 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIFYGTDSAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQDSGARGATGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 60 | AAV.cc42-87 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIFYGTDSAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNVALALGTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 61 | AAV.cc42-88 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIFYGTDSAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQGALRMGMTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 62 | AAV.cc42-89 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIFYGTDSAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLSGEGAVTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 63 | AAV.cc43-81 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLNSSVPSTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 64 | AAV.cc43-82 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQYMDHQVSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 65 | AAV.cc43-83 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA |

TABLE 4-continued

| SEQ ID NO | AAV9 Capsid Protein | Amino Acid Sequence |
|---|---|---|
| | | AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQTSDSLVSTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 66 | AAV.cc43-84 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNAVGALSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 67 | AAV.cc43-85 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQMPISHHETGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 68 | AAV.cc43-86 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQDSGARGATGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 69 | AAV.cc43-87 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNVALALGTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 70 | AAV.cc43-88 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQGALRMGMTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 71 | AAV.cc44-81 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIHGQSASRQTLKFSVAGPSNMAVQGRNYIPGPSYRQ |

TABLE 4-continued

| SEQ ID NO | AAV9 Capsid Protein | Amino Acid Sequence |
|---|---|---|
| | | QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLSGEGAVTGWVQNQGILPGMVWQDRDVYLQGPIWAKIPH TDGNFHPSPLMGGFGMKHPPPQILIKNTPVADPPTAFNKDKLNSFITQYSTGQVSVEIEWELQKENSKRW NPEIQYTSNYYKSNNVEFAVNTEGVYSEPRPIGTRYLTRNL |
| 72 | AAV.cc44-82 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIDTPTNQAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQYMDHQVSTGWVQNQGILPGMVWQDRDVYLQGPIWAKIP HTDGNFHPSPLMGGFGMKHPPPQILIKNTPVADPPTAFNKDKLNSFITQYSTGQVSVEIEWELQKENSKR WNPEIQYTSNYYKSNNVEFAVNTEGVYSEPRPIGTRYLTRNL |
| 73 | AAV.cc44-83 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIDTPTNQAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQTSDSLVSTGWVQNQGILPGMVWQDRDVYLQGPIWAKIPH TDGNFHPSPLMGGFGMKHPPPQILIKNTPVADPPTAFNKDKLNSFITQYSTGQVSVEIEWELQKENSKRW NPEIQYTSNYYKSNNVEFAVNTEGVYSEPRPIGTRYLTRNL |
| 74 | AAV.cc44-84 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIDTPTNQAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNAVGALSTGWVQNQGILPGMVWQDRDVYLQGPIWAKIP HTDGNFHPSPLMGGFGMKHPPPQILIKNTPVADPPTAFNKDKLNSFITQYSTGQVSVEIEWELQKENSKR WNPEIQYTSNYYKSNNVEFAVNTEGVYSEPRPIGTRYLTRNL |
| 75 | AAV.cc44-85 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIDTPTNQAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQMPISHHETGWVQNQGILPGMVWQDRDVYLQGPIWAKIPH TDGNFHPSPLMGGFGMKHPPPQILIKNTPVADPPTAFNKDKLNSFITQYSTGQVSVEIEWELQKENSKRW NPEIQYTSNYYKSNNVEFAVNTEGVYSEPRPIGTRYLTRNL |
| 76 | AAV.cc44-86 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIDTPTNQAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQDSGARGATGWVQNQGILPGMVWQDRDVYLQGPIWAKIP HTDGNFHPSPLMGGFGMKHPPPQILIKNTPVADPPTAFNKDKLNSFITQYSTGQVSVEIEWELQKENSKR WNPEIQYTSNYYKSNNVEFAVNTEGVYSEPRPIGTRYLTRNL |
| 77 | AAV.cc44-87 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIDTPTNQAQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNVALGLTGWVQNQGILPGMVWQDRDVYLQGPIWAKIPH TDGNFHPSPLMGGFGMKHPPPQILIKNTPVADPPTAFNKDKLNSFITQYSTGQVSVEIEWELQKENSKRW NPEIQYTSNYYKSNNVEFAVNTEGVYSEPRPIGTRYLTRNL |

TABLE 4-continued

| SEQ ID NO | AAV9 Capsid Protein | Amino Acid Sequence |
|---|---|---|
| 78 | AAV.cc44-88 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIDTPTNQAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQGALRMGMTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 79 | AAV.cc44-89 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIDTPTNQAQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQLSGEGAVTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 80 | AAV.cc45-81 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQLNSSVPSTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 81 | AAV.cc45-82 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQYMDHQVSTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 82 | AAV.cc45-83 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQTSDSLVSTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 83 | AAV.cc45-84 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQNAVGALSTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 84 | AAV.cc45-85 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF |

TABLE 4-continued

| SEQ ID NO | AAV9 Capsid Protein | Amino Acid Sequence |
|---|---|---|
| | | TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQMPISHHETGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 85 | AAV.cc45-86 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQDSGARGATGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 86 | AAV.cc45-87 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQNVALALGTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 87 | AAV.cc45-88 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQGALRMGMTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 88 | AAV.cc45-89 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIITRQAYQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQLSGEGAVTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 89 | AAV.cc46-81 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIRMFKSNQQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQLNSSVPSTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 90 | AAV.cc46-82 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY |

TABLE 4-continued

| SEQ ID NO | AAV9 Capsid Protein | Amino Acid Sequence |
|---|---|---|
| | | EFENVPFHSSYAHSQSLDRLMNPLIDQYLYYLSKTIRMFKSNQQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQYMDHQVSTGWVQNQGILPGMVWQDRDVYLQGPIWAKIP HTDGNFHPSPLMGGFGMKHPPPQILIKNTPVADPPTAFNKDKLNSFITQYSTGQVSVEIEWELQKENSKR WNPEIQYTSNYYKSNNVEFAVNTEGVYSEPRPIGTRYLTRNL |
| 91 | AAV.cc46-83 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIRMFKSNQQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQTSDSLVSTGWVQNQGILPGMVWQDRDVYLQGPIWAKIPH TDGNFHPSPLMGGFGMKHPPPQILIKNTPVADPPTAFNKDKLNSFITQYSTGQVSVEIEWELQKENSKRW NPEIQYTSNYYKSNNVEFAVNTEGVYSEPRPIGTRYLTRNL |
| 92 | AAV.cc46-85 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIRMFKSNQQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQMPISHHETGWVQNQGILPGMVWQDRDVYLQGPIWAKIPH TDGNFHPSPLMGGFGMKHPPPQILIKNTPVADPPTAFNKDKLNSFITQYSTGQVSVEIEWELQKENSKRW NPEIQYTSNYYKSNNVEFAVNTEGVYSEPRPIGTRYLTRNL |
| 93 | AAV.cc46-86 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIRMFKSNQQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQDSGARGATGWVQNQGILPGMVWQDRDVYLQGPIWAKIP HTDGNFHPSPLMGGFGMKHPPPQILIKNTPVADPPTAFNKDKLNSFITQYSTGQVSVEIEWELQKENSKR WNPEIQYTSNYYKSNNVEFAVNTEGVYSEPRPIGTRYLTRNL |
| 94 | AAV.cc46-87 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIRMFKSNQQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNVALALGTGWVQNQGILPGMVWQDRDVYLQGPIWAKIP HTDGNFHPSPLMGGFGMKHPPPQILIKNTPVADPPTAFNKDKLNSFITQYSTGQVSVEIEWELQKENSKR WNPEIQYTSNYYKSNNVEFAVNTEGVYSEPRPIGTRYLTRNL |
| 95 | AAV.cc46-88 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIRMFKSNQQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQGALRMGMTGWVQNQGILPGMVWQDRDVYLQGPIWAKIP HTDGNFHPSPLMGGFGMKHPPPQILIKNTPVADPPTAFNKDKLNSFITQYSTGQVSVEIEWELQKENSKR WNPEIQYTSNYYKSNNVEFAVNTEGVYSEPRPIGTRYLTRNL |
| 96 | AAV.cc46-89 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIRMFKSNQQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLSGEGAVTGWVQNQGILPGMVWQDRDVYLQGPIWAKIPH TDGNFHPSPLMGGFGMKHPPPQILIKNTPVADPPTAFNKDKLNSFITQYSTGQVSVEIEWELQKENSKRW NPEIQYTSNYYKSNNVEFAVNTEGVYSEPRPIGTRYLTRNL |

TABLE 4-continued

| SEQ ID NO | AAV9 Capsid Protein | Amino Acid Sequence |
|---|---|---|
| 97 | AAV.cc47-81 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIGVSLGGGQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQLNSSVPSTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 98 | AAV.cc47-82 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIGVSLGGGQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQYMDHQVSTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 99 | AAV.cc47-83 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIGVSLGGGQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQTSDSLVSTGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 100 | AAV.cc47-84 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIGVSLGGGQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQNAVGALSTGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 101 | AAV.cc47-85 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIGVSLGGGQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQMPISHHETGWVQNQGILPGMVWQDRDVYLQGPIWAKIPH<br>TDGNFHPSPLMGGFGMKHPPPQILIKNTPVPADPPTAFNKDKLNSFITQYSTGQVSVEIEWELQKENSKRW<br>NPEIQYTSNYYKSNNVEFAVNTEGVYSEPRPIGTRYLTRNL |
| 102 | AAV.cc47-86 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF<br>GYSTPWGYFDFNRFHCHFSPRDWQRLINNNWGFRPKRLNFKLFNIQVKEVTDNNGVKTIANNLTSTVQVF<br>TDSDYQLPYVLGSAHEGCLPPFPADVFMIPQYGYLTLNDGSQAVGRSSFYCLEYFPSQMLRTGNNFQFSY<br>EFENVPFHSSYAHSQSLDRLMNPLIDQYLYYLSKTIGVSLGGGQTLKFSVAGPSNMAVQGRNYIPGPSYRQ<br>QRVSTTVTQNNNSEFAWPGASSWALNGRNSLMNPGPAMASHKEGEDRFFPLSGSLIFGKQGTGRDNVDA<br>DKVMITNEEEIKTTNPVATESYGQVATNHQDSGARGATGWVQNQGILPGMVWQDRDVYLQGPIWAKIP<br>HTDGNFHPSPLMGGFGMKHPPPQILIKNTPVPADPPTAFNKDKLNSFITQYSTGQVSVEIEWELQKENSKR<br>WNPEIQYTSNYYKSNNVEFAVNTEGVYSEPRPIGTRYLTRNL |
| 103 | AV.cc47-87 | MAADGYLPDWLEDNLSEGIREWWALKPGAPQPKANQQHQDNARGLVLPGYKYLGPGNGLDKGEPVNA<br>ADAAALEHDKAYDQQLKAGDNPYLKYNHADAEFQERLKEDTSFGGNLGRAVFQAKKRLLEPLGLVEEA<br>AKTAPGKKRPVEQSPQEPDSSAGIGKSGAQPAKKRLNFGQTGDTESVPDPQPIGEPPAAPSGVGSLTMASG<br>GGAPVADNNEGADGVGSSSGNWHCDSQWLGDRVITTSTRTWALPTYNNHLYKQISNSTSGGSSNDNAYF |

TABLE 4-continued

| SEQ ID NO | AAV9 Capsid Protein | Amino Acid Sequence |
|---|---|---|
| | | GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIGVSLGGGQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNVALALGTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 104 | AAV.cc47-88 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIGVSLGGGQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQGALRMGMTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 105 | AAV.cc47-89 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIGVSLGGGQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLSGEGAVTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 106 | AAV.cc48-81 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLNSSVPSTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 107 | AAV.cc48-82 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQYMDHQVSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 108 | AAV.cc48-83 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQTSDSLVSTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 109 | AAV.cc48-84 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNAVGALSTGWVQNQGILPGMVWQDRDVYLQGPIWAKIP |

TABLE 4-continued

| SEQ ID NO | AAV9 Capsid Protein | Amino Acid Sequence |
|---|---|---|
| | | HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 110 | AAV.cc48-85 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQMPISHHETGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 111 | AAV.cc48-86 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQDSGARGATGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 112 | AAV.cc48-87 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQNVALALGTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 113 | AAV.cc48-88 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQGALRMGMTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 114 | AAV.cc48-89 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIKHFLQGEQTLKFSVAGPSNMAVQGRNYIPGPSYRQ QRVSTTVTQNNNSEFAWPGASSWALNGRNSLMNPGPAMASHKEGEDRFFPLSGSLIFGKQGTGRDNVDA DKVMITNEEEIKTTNPVATESYGQVATNHQLSGEGAVTGWVQNQGILPGMVWQDRDVYLQGPIWAKIPH TDGNFHPSPLMGGFGMKHPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| 115 | AAV.cc49-81 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQLNSSVPSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 116 | AAV.cc49-82 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA |

TABLE 4-continued

| SEQ ID NO | AAV9 Capsid Protein | Amino Acid Sequence |
|---|---|---|
| | | AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQYMDHQVSTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 117 | AAV.cc49-83 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQTSDSLVSTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 118 | AAV.cc49-84 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQNAVGALSTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 119 | AAV.cc49-85 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQMPISHHETGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |
| 120 | AAV.cc49-86 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQDSGARGATGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 121 | AAV.cc49-87 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQNVALALGTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 122 | AAV.cc49-88 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR |

TABLE 4-continued

| SEQ ID NO | AAV9 Capsid Protein | Amino Acid Sequence |
|---|---|---|
| | | QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQGALRMGMTGWVQNQGILPGMVWQDRDVYLQGPIWAKI PHTDGNFHPSPLMGGFGMKHPPPQILIKNTPVPADPPTAFNKDKLNSFITQYSTGQVSVEIEWELQKENSK RWNPEIQYTSNYYKSNNVEFAVNTEGVYSEPRPIGTRYLTRNL |
| 123 | AAV.cc49-89 | MAADGYLPDWLEDNLSEGIREWWALKPGAPQPKANQQHQDNARGLVLPGYKYLGPGNGLDKGEPVNA ADAAALEHDKAYDQQLKAGDNPYLKYNHADAEFQERLKEDTSFGGNLGRAVFQAKKRLLEPLGLVEEA AKTAPGKKRPVEQSPQEPDSSAGIGKSGAQPAKKRLNFGQTGDTESVPDPQPIGEPPAAPSGVGSLTMASG GGAPVADNNEGADGVGSSSGNWHCDSQWLGDRVITTSTRTWALPTYNNHLYKQISNSTSGGSSNDNAYF GYSTPWGYFDFNRFHCHFSPRDWQRLINNNWGFRPKRLNFKLFNIQVKEVTDNNGVKTIANNLTSTVQVF TDSDYQLPYVLGSAHEGCLPPFPADVFMIPQYGYLTLNDGSQAVGRSSFYCLEYFPSQMLRTGNNFQFSY EFENVPFHSSYAHSQSLDRLMNPLIDQYLYYLSKTIMGRERAGQTLKFSVAGPSNMAVQGRNYIPGPSYR QQRVSTTVTQNNNSEFAWPGASSWALNGRNSLMNPGPAMASHKEGEDRFFPLSGSLIFGKQGTGRDNVD ADKVMITNEEEIKTTNPVATESYGQVATNHQLSGEGAVTGWVQNQGILPGMVWQDRDVYLQGPIWAKIP HTDGNFHPSPLMGGFGMKHPPPQILIKNTPVPADPPTAFNKDKLNSFITQYSTGQVSVEIEWELQKENSKR WNPEIQYTSNYYKSNNVEFAVNTEGVYSEPRPIGTRYLTRNL |

In embodiments wherein any amino acid residue identified as $X^1$ through $X^7$ is not substituted, the amino acid residue at the unsubstituted position can be the wild type amino acid residue of the reference amino acid sequence (e.g., AAV9 (SEQ ID NO: 1)). In some embodiments, capsid protein variants herein may have an amino acid substitution at residues 452N, 453G, 454S, 455G, 456Q, 457N, and/or 458Q of SEQ ID NO: 1 (AAV9 capsid protein; VP1 numbering) in any combination. In some embodiments, capsid protein variants herein may have an amino acid substitution at residues 586S, 587A, 588Q, 589A, 590Q, 591A, and/or 592Q of SEQ ID NO: 1 (AAV9 capsid protein; VP1 numbering) in any combination.

In some embodiments, capsid protein variants of the present disclosure can be produced by modifying the capsid protein of any AAV capsid protein now known or later discovered. Further, the AAV capsid protein that is to be modified according to the present disclosure can be a naturally occurring AAV capsid protein (e.g., an AAV2, AAV3a or 3b, AAV4, AAV5, AAV8, AAV9, AAV10 or AAV11 capsid protein or any of the AAV shown in Table 1) but is not so limited. Those skilled in the art will understand that a variety of manipulations to the AAV capsid proteins are known in the art and the invention is not limited to modifications of naturally occurring AAV capsid proteins. For example, the capsid protein to be modified may already have one or more alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11, AAV12 or any other AAV now known or later discovered). Such AAV capsid proteins are also within the scope of the present disclosure.

Some aspects of the present disclosure provide for virus capsids which may have one or more of any of the capsid protein variants disclosed herein. In some embodiments, a virus capsid herein can be a parvovirus capsid, which may further be an autonomous parvovirus capsid or a dependovirus capsid. Optionally, a virus capsid herein may be an AAV capsid. In some embodiments, AAV capsids of the present disclosure may be an AAV1, AAV2, AAV3a, AAV3b, AAV4, AAV5, AAV6, AAV7, AAV8, AAV9, AAV10, AAV11, AAV12, AAVrh8, AAVrh10, AAVrh32.33, bovine AAV capsid, avian AAV capsid and/or any other AAV now known or later identified.

In some embodiments, modified virus capsids herein can be used as capsid vehicles. In some embodiments, molecules can be packaged by the modified virus capsids herein and transferred into a cell wherein the molecules can include heterologous DNA, RNA, polypeptides, small organic molecules, metals, or combinations of the same. Heterologous molecules are defined herein as those that are not naturally found in an AAV infection, e.g., those not encoded by a wild-type AAV genome. Further, therapeutically useful molecules for use herein can be associated with the outside of the chimeric virus capsid for transfer of the molecules into one or more host target cells. Such associated molecules can include DNA, RNA, small organic molecules, metals, carbohydrates, lipids and/or polypeptides. In some embodiments, a therapeutically useful molecule herein may be covalently linked (i.e., conjugated or chemically coupled) to a capsid proteins. Methods of covalently linking molecules are known by those skilled in the art.

In some embodiments, modified virus capsids herein can be used in raising antibodies against the capsid protein variants disclosed herein. As a further alternative, an exogenous amino acid sequence may be inserted into the modified virus capsid for antigen presentation to a cell, e.g., for administration to a subject to produce an immune response to the exogenous amino acid sequence.

In some embodiments, modified virus capsids herein may be a targeted virus capsid, comprising a targeting sequence (e.g., substituted or inserted in the viral capsid) that may direct the virus capsid to interact with cell-surface molecules present on desired target tissue(s) (see, e.g., international patent publication WO 00/28004 and Hauck et al., (2003) *J. Virology* 77:2768-2774); Shi et al., *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al., *Molecular Therapy* 3:964-975 (2001)).

As an example, a virus capsid of the present disclosure may have relatively inefficient tropism toward certain target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another example, one or more non-naturally occurring amino acids as described by Wang et al., *Annu Rev Biophys Biomol Struct.* 35:225-49 (2006) can be incorporated into an AAV capsid subunit of this invention at an orthogonal site as a means of redirecting a low-transduction vector to desired target tissue(s). These unnatural amino acids can advantageously be used to chemically link molecules of interest to the AAV capsid protein including without limitation: glycans (mannose-dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques*, $1^{st}$ edition, Academic Press, 1996).

In some embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV9) to confer heparin binding to the resulting mutant. In another nonlimiting example, the globoside receptor binding domain of the B19 capsid may be substituted into an AAV capsid protein of this invention to target a virus capsid or virus vector comprising the same to erythroid cells.

In some embodiments, an exogenous targeting sequence for use herein may be any amino acid sequence encoding a peptide that alters the tropism of a virus capsid or virus vector comprising the modified AAV capsid protein. In some embodiments, the targeting peptide or protein may be naturally occurring or, alternately, completely or partially synthetic. In some examples, targeting sequences may include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., $\alpha,\beta$ or $\gamma$), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, ($\beta$-endorphin, leu-enkephalin, rimorphin, $\alpha$-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as $\alpha$-bungarotoxin, and the like) can be substituted into the capsid protein as a targeting sequence. In some other embodiments, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein. Also encompassed are peptide motifs that direct uptake by specific cells, e.g., a FVFLP (SEQ ID NO: 41) peptide motif triggers uptake by liver cells. In some embodiments, a targeting sequence for use herein may be a peptide that can be used for chemical coupling (e.g., can comprise arginine and/or lysine residues that can be chemically coupled through their R groups) to another molecule that targets entry into a cell.

In some embodiments, capsid protein variants, virus capsids and/or AAV vectors (e.g., ccAVVs) disclosed herein can have equivalent or enhanced transduction efficiency relative to the transduction efficiency of the AAV serotype from which the capsid protein variant, virus capsid and/or vector originated. In some embodiments, capsid protein variants, virus capsids and/or vectors (e.g., ccAVVs) disclosed herein can have reduced transduction efficiency relative to the transduction efficiency of the AAV serotype from which the capsid protein variant, virus capsid and/or vector originated. In some embodiments, capsid protein variants, virus capsids and/or vectors (e.g., ccAVVs) disclosed herein can have equivalent or enhanced tropism relative to the tropism of the AAV serotype from which capsid protein variant, virus capsid and/or vector originated. In some embodiments, capsid protein variants, virus capsids and/or vectors (e.g., ccAVVs) disclosed herein can have an altered or different tropism relative to the tropism of the AAV serotype from which the capsid protein variant, virus capsid and/or vector originated. In some embodiments, capsid protein variants, virus capsids and/or vectors (e.g., ccAVVs) disclosed herein can have or be engineered to have tropism for brain tissue. In some embodiments, capsid protein variants, virus capsids and/or AAV vectors (e.g., ccAVVs) disclosed herein can produce an attenuated immunological response relative to the immunological response of the AAV serotype from which the capsid protein variant, virus capsid and/or vector originated. In some embodiments, capsid protein variants, virus capsids and/or AAV vectors (e.g., ccAVVs) disclosed herein can be administered to a subject in multiple dosages (e.g., about two doses, about three doses, about four doses, about 5 doses, about 10 doses, about 15 doses, about 20 doses, about 40 doses, as many doses as needed to observe one or more desired responses) relative to the number of doses that can be administered using the AAV serotype from which the capsid protein variant, virus capsid and/or vector originated.

(A) Capsid and ccAAV Engineering

In some embodiments, rational engineering and/or mutational methods may be used to identify capsid protein variants of AAV vectors (e.g., ccAAVs) disclosed herein. In some embodiments, methods herein can be used to produce an AAV vector that evades neutralizing antibodies. In some embodiments, methods herein can be used to produce an AAV vector that has improved gene transfer efficiency. In some embodiments, methods herein can be used to produce an AAV vector that has improved gene transfer efficiency in more than one mammalian species. In some embodiments, methods herein can be used to produce an AAV vector that specifically targets a cell or tissue of interest (e.g., a kidney cell).

In some embodiments, a recombinant AAV described herein has improved gene transfer efficiency in one or more mammalian species relative to a recombinant AAV that has a capsid protein that is otherwise identical, except it lacks the one or more amino acid substitutions. In some embodiments, the improved gene transfer efficiency is occurs in one more of: *Mus Musculus* (mouse), *Sus scrofa* (pig), *Canis Familiaris* (Dog), Non-human primates (*Macaca*, macaque), or *Homo sapiens* (human). In some embodiments, the improved gene transfer efficiency occurs in one or more of the following cell types or tissues: spinal cord (e.g., glial cells, neurons, endothelial cells), dorsal root ganglion, brain, heart, lung, kidney, skeletal muscle, spleen, pancreas, small intestine, large intestine, or liver. In some embodiments, the improved gene transfer efficiency occurs in kidney cells or kidney tissue.

Aspects of the present disclosure provide for methods of producing AAV vectors as disclosed herein. In some embodiments, methods can include one or more of the following steps: a) identifying contact amino acid residues that form a three dimensional antigenic footprint on an AAV capsid protein; b) generating a library of AAV capsid proteins comprising amino acid substitutions of the contact amino acid residues identified in (a); c) producing AAV particles comprising capsid proteins from the library of AAV capsid proteins of (b); d) contacting the AAV particles of (c) with cells under conditions whereby infection and replication can occur; e) selecting AAV particles that can complete at least one infectious cycle and replicate to titers similar to control AAV particles; f) contacting the AAV particles selected in (e) with neutralizing antibodies and cells under conditions whereby infection and replication can occur; and g) selecting AAV particles that are not neutralized by the neutralizing antibodies of (f). Non-limiting examples of methods for identifying contact amino acid residues include peptide epitope mapping and/or cryo-electron microscopy. One of skill in the art will appreciate that there is an ever evolving variety of methods and protocols that can be used to generate a library of AAV capsid proteins (e.g., rational design, barcoding, direct evolution, in silico discovery). Any method of generating a library of AAV capsid protein known in the field or to be discovered that is suited for used herein may be used and/or optimized for use according to the methods disclosed herein.

In some embodiments, generating a library of AAV capsid proteins comprising amino acid substitutions of the contact amino acid residues identified in an AAV capsid protein can produce a parental AAV capsid protein library. In some embodiments, methods of producing ccAAV vectors herein can include administering the parental AAV capsid protein library to a mammal. In some embodiments, administering the parental AAV capsid protein library to a mammal may be systemic administration to the mammal. In some embodiments, the parental AAV capsid protein library may be administered to a mammal having a species of *Mus Musculus* (mouse), *Sus scrofa* (pig), *Canis Familiaris* (Dog), Non-human primates (*Macaca*, macaque), or *Homo sapiens* (human). In some embodiments, capsid proteins can be enriched by collecting from a cell and/or a tissue from the mammal after administration of the parental AAV capsid protein library. In some embodiments, capsid proteins can be enriched by collecting from a cell and/or a tissue from the mammal after administration of the parental AAV capsid protein library wherein the cell and/or a tissue comprises spinal cord (e.g., glial cells, neurons, endothelial cells), dorsal root ganglion, brain, heart, lung, kidney, skeletal muscle, spleen, pancreas, small intestine, large intestine, or liver tissue, and any combination thereof. In some embodiments, capsid proteins can be collected from the mammal after about 1 days to about 1 month (e.g., about 1 day, 5 days, 1 week, 2 weeks, 3 weeks, one month) following administration of the parental AAV capsid protein library. In some embodiments, capsid proteins collected from a mammal after administration of the parental AAV capsid protein library can be used to generate another AAV capsid protein library referred to as the evolved AAV capsid protein library.

In some embodiments, the evolved AAV capsid protein library may be administered to a mammal having a species of *Mus Musculus* (mouse), *Sus scrofa* (pig), *Canis Familiaris* (Dog), Non-human primates (*Macaca*, macaque), or *Homo sapiens* (human) provided that the species is not the same as the species the parental AAV capsid protein library was administered to. In some embodiments, capsid proteins can be enriched by collecting from a cell and/or a tissue from the mammal after administration of the evolved AAV capsid protein library. In some embodiments, capsid proteins can be enriched by collecting from a cell and/or a tissue from the mammal after administration of the evolved AAV capsid protein library wherein the cell and/or a tissue comprises spinal cord (e.g., glial cells, neurons, endothelial cells), dorsal root ganglion, brain, heart, lung, kidney, skeletal muscle, spleen, pancreas, small intestine, large intestine, or liver tissue, and any combination thereof. In some embodiments, capsid proteins can be collected and identified from the mammal after administration of the evolved AAV capsid protein library. In some embodiments, capsid proteins can be collected and identified from the mammal after about 1 days to about 1 month (e.g., about 1 day, 5 days, 1 week, 2 weeks, 3 weeks, one month) following administration of the evolved AAV capsid protein library. In some embodiments, capsid proteins collected and identified from a mammal after administration of the evolved AAV capsid protein library can be used to generate an additional, second evolved AAV capsid protein library. In some embodiments, the second evolved AAV capsid protein library may be administered to a mammal having a species of *Mus Musculus* (mouse), *Sus scrofa* (pig), *Canis Familiaris* (Dog), Non-human primates (*Macaca*, macaque), or *Homo sapiens* (human) provided that the species is not the same as the species the first evolved AAV capsid protein library was administered to. In some embodiments, the second evolved AAV capsid protein library may be administered to a mammal having a species of *Mus Musculus* (mouse), *Sus scrofa* (pig), *Canis Familiaris* (Dog), Non-human primates (*Macaca*, macaque), or *Homo sapiens* (human) provided that the species is not the same as the species the first evolved AAV capsid protein library was administered to and that the species is the same as the species the parental AAV capsid protein library was administered to. In some embodiments, the second evolved AAV capsid protein library may be administered to a mammal having a species of *Mus Musculus* (mouse), *Sus scrofa* (pig), *Canis Familiaris* (Dog), Non-human primates (*Macaca*, macaque), or *Homo sapiens* (human) provided that the species is not the same as the species the first evolved AAV capsid protein library was administered to and that the species is not the same as the species the parental AAV capsid protein library was administered to.

In some embodiments, each generation of an evolved library can be referred to as a "cycle" of coevolving an AAV capsid protein library. In some embodiments, methods herein of coevolving an AAV capsid protein library may involve about one to about 10 (e.g., about 1, 2, 3, 4, 5, 6, 7, 8, 9, 10) cycles. In some embodiments, each cycle as disclosed herein may be performed in a species different than the cycle proceeding it. In some examples, methods herein of coevolving an AAV capsid protein library may involve one cycle in a mouse, a second cycle in a pig, a third cycle in a mouse, a fourth cycle in a pig and so on. In some examples, methods herein of coevolving an AAV capsid protein library may involve one cycle in a mouse, a second cycle in a non-human primate, a third cycle in a mouse, a fourth cycle in a non-human primate and so on. In some examples, methods herein of coevolving an AAV capsid protein library may involve one cycle in a mouse, a second cycle in a pig, a third cycle in a non-human primate, a fourth cycle in a mouse, and so on. In some examples, methods herein of coevolving an AAV capsid protein library may involve one cycle in a pig, a second cycle in a mouse, a third cycle in a non-human primate (e.g., a monkey), and so on.

In some embodiments, a method of evolving novel strains of adeno-associated viruses comprising passaging AAV libraries across multiple mammalian species, wherein the AAV libraries comprise a plurality of recombinant AAV vectors, wherein each recombinant AAV vector comprises a capsid protein variant comprising one or more amino acid mutations relative to a wildtype AAV capsid protein. In some embodiments, each recombinant AAV vector in the AAV libraries comprises one or more amino acid mutations relative to a wildtype AAV9 capsid protein (SEQ ID NO: 1). In some embodiments, the one or more amino acid mutations are in the regions corresponding to amino acids 452-458 of SEQ ID NO: 1 or 586-592 of SEQ ID NO: 1, or the mutations are found in both regions corresponding to amino acids 452-458 and 586-592 of SEQ ID NO: 1.

In some embodiments, a method of evolving novel strains of AAV comprises administering a first AAV library to a first mammalian species. The AAVs from the first AAV library present in one or more target tissues of the first mammalian species may then be sequenced, and used to generate a second AAV library. The second AAV library may subsequently be administered to a second mammalian species, wherein the first mammalian species and the second mammalian species are different. The AAVs from the second AAV library present in one or more target tissues of the second mammalian species may then be sequenced. In some embodiments, the first mammalian species and the second mammalian species are each independently selected from the group consisting of: *Mus Musculus* (mouse), *Sus scrofa* (pig), *Canis Familiaris* (Dog), Non-human primates (*Macaca*, macaque), and *Homo sapiens* (human). These steps may then be repeated with a third, fourth, fifth, sixth, etc. species. In some embodiments, the one or more target tissues of the first mammalian species, the second mammalian species (or any subsequent species) is selected from spinal cord (e.g., glial cells, neurons, endothelial cells), dorsal root ganglion, brain, heart, lung, kidney, skeletal muscle, spleen, pancreas, small intestine, large intestine, or liver tissue, and any combination thereof.

(B) AAV Vectors

In certain embodiments, the present disclosure provides AAV vectors comprising one or more of the capsid protein variants disclosed herein. As used herein, a "vector" refers to any molecule or moiety which transports, transduces or otherwise acts as a carrier of a heterologous molecule. A "viral vector" is a vector which comprises one or more polynucleotide regions encoding or comprising a payload molecule of interest, e.g., a transgene, a polynucleotide encoding a polypeptide or multi-polypeptide or a modulatory nucleic acid. Viral vectors of the present invention may be produced recombinantly using methods known in the art. Such techniques are explained fully in the literature, such as in *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; and *Cell Biology: A Laboratory Notebook* (J. E. Cellis, ed., 1989) Academic Press.

In some embodiments, AAV viral particles disclosed herein can have a vector genome for expressing one or more of the capsid protein variants disclosed herein. The vector genome of the AAV vector may, in some embodiments, be derived from the wild type genome of a virus, such as AAV, by using molecular methods to remove the wild type genome from the virus (e.g., AAV), and replacing with a non-native nucleic acid, such as a heterologous polynucleotide sequence (e.g., a coding sequence for a transgene of interest). Typically, for AAV vectors, one or both inverted terminal repeat (ITR) sequences of the wild type AAV genome are retained in the AAV vector whereas other parts of the wild type viral genome are replaced with a non-native sequence such as a heterologous polynucleotide sequence between the retained ITRs. The vector genomes disclosed herein can encompass AAV genome-derived backbone elements, a coding sequence for a capsid protein variant disclosed herein, and a suitable promoter in operable linkage to the coding sequence. In some examples, vector genomes disclosed herein can further comprise regulatory sequences regulating expression and/or secretion of the encoded protein. Examples include, but are not limited to, enhancers, polyadenylation signal sites, internal ribosome entry sites (IRES), sequences encoding protein transduction domains (PTD), microRNA-target sites, or a combination thereof.

In some examples, vector genomes described herein may be single stranded. In other examples, vector genomes disclosed herein may be double stranded. For example, vector genome described herein may be a self-complementary AAV vector genome capable of comprising double stranded portions therein.

(1) AAV-Backbone Elements

In some embodiments, vector genomes disclosed herein may have one or more AAV-genome derived backbone elements, which refer to the minimum AAV genome elements required for the bioactivity of the AAV vectors. For example, the AAV-genome derived backbone elements may include the packaging site for the vector to be assembled into an AAV viral particle, one or more of the capsid protein variants disclosed herein, elements needed for vector replication, and/or expression of a transgene-encoding sequence comprised therein in host cells.

In some examples, vector genome backbones disclosed herein may include at least one inverted terminal repeat (ITR) sequence. In some examples, vector genome backbones herein may include two ITR sequences. In some examples, one ITR sequence can be 5' of a polynucleotide sequence coding for a transgene. In some examples, one ITR sequence can be 3' of a polynucleotide sequence coding for a transgene. In some examples, a polynucleotide sequence coding for a transgene herein can be flanked on either side by an ITR sequence. Accordingly, in some embodiments, a vector genome comprises a transgene located between the first ITR and the second ITR.

In some embodiments, vector genomes herein may include sequences or components originating from at least one distinct AAV serotype. In some examples, AAV vector genome backbones disclosed herein may include at least ITR sequence from one distinct AAV serotype. In some examples, AAV vector genome backbones disclosed herein may include at least ITR sequence from one distinct human AAV serotype. Such a human AAV may be derived from any known serotype, e.g., from any one of serotypes 1-11. In some examples, AAV serotypes used herein have a tropism for the central nervous system (CNS), cardiac tissues, skeletal muscle, and/or liver tissues. In some examples, AAV vector genome backbones disclosed herein may have an ITR sequence of serotype AAV9.

In some embodiments, AAV vectors herein can be a pseudotyped AAV vector, (i.e., comprises sequences or components originating from at least two distinct AAV serotypes). In some embodiments, a pseudotyped AAV vector herein may include an AAV genome backbone derived from one AAV serotype, and a capsid protein derived at least in part from a distinct AAV serotype. In some examples, pseudotyped AAV vectors herein can have an AAV2 vector genome backbone and a capsid protein derived from an AAV serotype having a tropism for heart tissue (e.g., AAV1, AAV2, AAV4, AAV5, AAV8, or AAV9).

In order to analyze the success of viral vector-mediated gene transfer, it may be important to be able to monitor both the distribution of the vector and the effectiveness of vector-mediated gene expression. This can be achieved by subcloning a reporter gene into the vector genome backbone. In some examples, AAV vector genome backbones disclosed herein may contain a reporter gene. Several reporter genes are commonly used for this purpose and include, but are not limited to, fluorescent proteins of various colors (including green fluorescent protein (GFP), red fluorescent protein (RFP)), *E. coli* β-galactosidase (LacZ), and various forms of luciferase (Luc). In some examples, AAV vector backbones disclosed herein may contain GFP.

The vector constructs disclosed herein may be prepared using known techniques. (See e.g., *Current Protocols in Molecular Biology*, Ausubel., F. et al., eds, Wiley and Sons, New York 1995). Fragment length can be chosen so that the recombinant genome does not exceed the packaging capacity of the AAV particle. If necessary, a "stuffer" DNA sequence can be added to the construct to maintain standard AAV genome size for comparative purposes. Such a fragment may be derived from such non-viral sources, e.g., lacZ, or other genes which are known and available to those skilled in the art.

(2) Self-Complementary AAV Viral Vectors

In some embodiments, AAV vectors disclosed herein can be self-complementary AAV (scAAV) vectors. Self-complementary AAV (scAAV) vectors contain complementary sequences that are capable of spontaneously annealing (folding back on itself to form a double-stranded genome) when entering into infected cells, thus circumventing the need for converting a single-stranded DNA vector using the cell's DNA replication machinery. An AAV herein having a self-complementing genome can quickly form a double stranded DNA molecule by virtue of its partially complementing sequences (e.g., complementing coding and non-coding strands of a transgene-encoding sequence).

In some embodiments, a scAAV viral vector disclosed herein may comprise a first heterologous polynucleotide sequence and a second heterologous polynucleotide sequence, which can form intrastrand base pairs. In some examples, the first heterologous polynucleotide sequence and the second heterologous polynucleotide sequence are linked by a sequence that facilitates intrastrand base pairing; e.g., to form a hairpin DNA structure. In some examples, the dimeric structure of a scAAV vector upon entering a cell can be stabilized by a mutation or a deletion of one of the two terminal resolution sites (trs). As trs are Rep-binding sites contained within each ITR, a mutation or a deletion of such trs may prevent cleavage of a dimeric structure of a scAAV vector by AAV Rep proteins to form monomers. In some embodiments, a scAAV viral vector disclosed herein may include a truncated 5' inverted terminal repeats (ITR), a truncated 3' ITR, or both. In some examples, a scAAV vector disclosed herein may comprise a truncated 3' ITR, in which the D region or a portion thereof (e.g., the terminal resolution sequence therein) may be deleted. Such a truncated 3' ITR may be located between the first heterologous polynucleotide sequence and a second heterologous polynucleotide sequence noted above.

(3) Promoters

In some embodiments, AAV vectors disclosed herein comprise further elements necessary for expression, such as at least one suitable promoter which controls the expression of the transgene-encoding sequence. Such a promoters may be ubiquitous, tissue-specific, strong, weak, regulated, chimeric, etc., to allow efficient and suitable production of the protein in the infected tissue. The promoter may be homologous to the encoded protein, or heterologous, including cellular, viral, fungal, plant or synthetic promoters. Most preferred promoters for use herein may be functional in human cells. Non-limiting examples of ubiquitous promoters include viral promoters, particularly the CMV promoter, the RSV promoter, the SV40 promoter, etc. and cellular promoters such as the PGK (phosphoglycerate kinase) promoter. In some embodiments, viral promoters herein can be a CMV promoter, a SV40 promoter, or any combination thereof.

In some embodiments, AAV vectors disclosed herein may comprise further elements necessary for expression, such as at least one suitable promoter which controls the expression of the transgene-encoding sequence after infection of the appropriate cells. Suitable promoters for use herein include, in addition to the AAV promoters, e.g. the cytomegalovirus (CMV) promoter or the chicken beta actin/cytomegalovirus hybrid promoter (CAG), an endothelial cell-specific promoter such as the VE-cadherin promoter, as well as steroid promoters and metallothionein promoters. In some embodiments, the promoter used in the vectors disclosed herein can be a CAG promoter.

In some embodiments, the transgene-encoding sequence according to the invention comprises a tissue specific promoter which is functionally linked to the transgene-encoding sequence to be expressed. Accordingly, the specificity of the vectors according to the disclosure for the tissue (e.g., brain, heart, muscle, liver) can be further increased. In some examples, a vector disclosed herein can have a tissue-specific promoter whose activity in the specific tissue is at least about 2-fold, 5-fold, 10-fold, 20-fold, 50-fold or 100-fold higher than in a tissue which is not the specific tissue. In some examples, a tissue specific promoter herein is a human a tissue specific promoter. In some examples, the expression cassette can also include an enhancer element for increasing the expression levels of exogenous protein to be expressed. Furthermore, the expression cassette may further comprise polyadenylation sequences, such as the SV40 polyadenylation sequences or polyadenylation sequences of bovine growth hormone.

(4) Other Regulatory Elements for Gene Expression

In some embodiments, AAV vectors disclosed herein may include one or more conventional control elements which are operably linked to the transgene-encoding sequence in a manner which permits its transcription, translation and/or expression in a cell transfected with the plasmid vector or infected with the virus produced by the invention. As used herein, "operably linked" sequences may include both expression control sequences that are contiguous with the transgene-encoding sequence and expression control sequences that act in trans or at a distance to control the transgene-encoding sequence. Expression control sequences may further comprise appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized herein.

In some embodiments, an AAV vector disclosed herein may include a modified capsid, including proteins or peptides of non-viral origin or structurally modified, to alter the tropism of the vector. For example, the capsid may include a ligand of a particular receptor, or a receptor of a particular ligand, to target the vector towards cell type(s) expressing said receptor or ligand, respectively.

(C) Serotype of AAV Viral Particles

In some embodiments, AAV vectors disclosed herein may be prepared or derived from various serotypes of AAVs. The term "serotype" is a distinction with respect to an AAV having a capsid which is serologically distinct from other AAV serotypes. Serologic distinctiveness is determined on the basis of the lack of cross-reactivity between antibodies to the AAV as compared to other AAV. Cross-reactivity can be measured using methods known in the art. For example, cross-reactivity herein may be measured using a neutralizing antibody assay. For this assay polyclonal serum is generated against a specific AAV in a rabbit or other suitable animal model using the adeno-associated viruses. In this assay, the serum generated against a specific AAV is then tested in its ability to neutralize either the same (homologous) or a heterologous AAV. The dilution that achieves 50% neutralization is considered the neutralizing antibody titer. If for two AAVs the quotient of the heterologous titer divided by the homologous titer is lower than 16 in a reciprocal manner, those two vectors are considered as the same serotype. Conversely, if the ratio of the heterologous titer over the homologous titer is 16 or more in a reciprocal manner the two AAVs are considered distinct serotypes.

In some embodiments, AAV vectors herein may be mixed of at least two serotypes of AAVs or with other types of viruses to produce chimeric (e.g. pseudotyped) AAV viruses. In some embodiments, AAV vectors herein may be a human serotype AAV vector. Such a human AAV may be derived from any known serotype, e.g., from any one of serotypes 1-11.

(D) Methods of Making AAV Particles

In some embodiments, AAV vector genomes described herein may be packaged into virus particles which can be used to deliver the genome for transgene-encoding sequence expression in target cells. In some embodiments, AAV vector genomes disclosed herein can be packaged into particles by transient transfection, use of producer cell lines, combining viral features into Ad-AAV hybrids, use of herpesvirus systems, or production in insect cells using baculoviruses.

A method of generating a packaging cell for use herein can involve creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing, addition of synthetic linkers containing restriction endonuclease cleavage sites, or by direct, blunt-end ligation. The packaging cell line is then infected with a helper virus, such as adenovirus. The advantages of this method are that the cells are selectable and are suitable for large-scale production of rAAV. Examples of suitable methods herein employ adenovirus or baculovirus, rather than plasmids, to introduce rAAV genomes and/or rep and cap genes into packaging cells.

(E) Characteristics of AAV Vectors and AAV Particles

In some embodiments, AAV vectors (e.g., ccAAVs) and/or AAV particles herein may have one or more improvements compared to naturally isolated AAV vectors. As used herein, a "naturally isolated AAV vector" refers to a vector that does not comprise one or more of the capsid protein variants disclosed herein. In some embodiments, AAV vectors (e.g., ccAAVs) and/or AAV particles herein may have increased gene transfer efficiency in a cell compared to naturally isolated AAV vectors. In some embodiments, AAV vectors (e.g., ccAAVs) and/or AAV particles herein may have at least about 2-fold to about 50-fold (e.g., about 2-, 4-, 6-, 8-, 10-, 20-, 30-, 40-, 50-fold) increased gene transfer efficiency in a cell compared to naturally isolated AAV vectors.

In some embodiments, AAV vectors (e.g., ccAAVs) and/or AAV particles herein may have increased gene transfer efficiency in the cell and/or tissue of one or more mammalian species. In some embodiments, AAV vectors (e.g., ccAAVs) and/or AAV particles herein may have increased gene transfer efficiency in the cell and/or tissue of one or more of *Mus Musculus* (mouse), *Sus scrofa* (pig), *Canis Familiaris* (Dog), Non-human primates (*Macaca*, macaque), or *Homo sapiens* (human), and any combination thereof. In some embodiments, AAV vectors (e.g., ccAAVs) and/or AAV particles herein may have increased gene transfer efficiency in a cell and/or tissue of a mammalian spinal cord (e.g., glial cells, neurons, endothelial cells), dorsal root ganglion, brain, heart, lung, kidney, skeletal muscle, spleen, pancreas, small intestine, large intestine, liver tissue, and any combination thereof.

In some embodiments, AAV vectors (e.g., ccAAVs) and/or AAV particles herein may have a higher vector titer compared to naturally isolated AAV vectors. In some embodiments, AAV vectors (e.g., ccAAVs) and/or AAV particles herein may have at least about 2-fold to about 50-fold (e.g., about 2-, 4-, 6-, 8-, 10-, 20-, 30-, 40-, 50-fold) higher vector titer compared to naturally isolated AAV vectors.

In some embodiments, AAV vectors (e.g., ccAAVs) and/or AAV particles herein may be less susceptible to antibody-mediated neutralization compared to naturally isolated AAV vectors. In some embodiments, AAV vectors (e.g., ccAAVs) and/or AAV particles herein may be less susceptible to antibody-mediated neutralization by about 2-fold to about 50-fold (e.g., about 2-, 4-, 6-, 8-, 10-, 20-, 30-, 40-, 50-fold) compared to naturally isolated AAV vectors. In some embodiments, AAV vectors (e.g., ccAAVs) and/or AAV particles herein may be less susceptible to antibody-mediated neutralization for at least about 1 hour to about 24 hours (e.g., about 1, 2, 4, 8, 12, 16, 20, 24 hours) after administration to a subject compared to naturally isolated AAV vectors.

In some embodiments, AAV vectors (e.g., ccAAVs) and/or AAV particles herein may produce lower levels of anti-AAV antibodies after at least one administration to a subject herein compared to naturally isolated AAV vectors. In some embodiments, AAV vectors (e.g., ccAAVs) and/or AAV particles herein may produce about 2-fold to about 50-fold (e.g., about 2-, 4-, 6-, 8-, 10-, 20-, 30-, 40-, 50-fold) less anti-AAV antibodies after at least one administration to a subject herein compared to naturally isolated AAV vectors. In some embodiments, gene therapies comprising AAV vectors (e.g., ccAAVs) and/or AAV particles herein can be administered about 2 times to about 10 times (e.g., about 2, 3, 4, 5, 6, 8, 9, 10) to a subject herein without becoming susceptible to antibody-mediated neutralization.

In some embodiments, AAV vectors (e.g., ccAAVs) and/or AAV particles herein may expression in any cell or tissue type of more than one mammal. In some embodiments, AAV vectors (e.g., ccAAVs) and/or AAV particles herein may expression in any cell or tissue type of more than one mammal comprising a human, mouse, rat, guinea pig, dog, cat, horse, cow, pig, or non-human primate (e.g., monkey, chimpanzee, baboon, gorilla). In some embodiments, AAV vectors (e.g., ccAAVs) and/or AAV particles herein may expression in any cell or tissue type of a human, a mouse, a dog, and a non-human primate.

III. Pharmaceutical Compositions

In some embodiments, any of the AAV vectors (e.g., ccAAVs), virus capsids, and/or AAV viral particles disclosed herein may be formulated to form a pharmaceutical composition. In some examples, pharmaceutical composition herein can further include a pharmaceutically acceptable carrier, diluent or excipient. Any of the pharmaceutical compositions to be used in the present methods can comprise pharmaceutically acceptable carriers, excipients, or stabilizers in the form of lyophilized formations or aqueous solutions.

The carrier in the pharmaceutical composition must be "acceptable" in the sense that it is compatible with the active ingredient of the composition, and preferably, capable of stabilizing the active ingredient and not deleterious to the subject to be treated. For example, "pharmaceutically acceptable" may refer to molecular entities and other ingredients of compositions comprising such that are physiologically tolerable and do not typically produce untoward reactions when administered to a mammal (e.g., a human). In some examples, the "pharmaceutically acceptable" carrier used in the pharmaceutical compositions disclosed herein may be those approved by a regulatory agency of the Federal or a state government or listed in the U.S. Pharmacopeia or other generally recognized pharmacopeia for use in mammals, and more particularly in humans.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: The Science and Practice of Pharmacy 20$^{th}$ Ed. (2000) Lippincott Williams and Wilkins, Ed. K. E. Hoover.

In some embodiments, the pharmaceutical compositions or formulations are for parenteral administration, such as intravenous, intracerebroventricular injection, intra-cisterna magna injection, intra-parenchymal injection, or a combination thereof. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Pharmaceutical compositions disclosed herein may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Aqueous solutions may be suitably buffered (preferably to a pH of from 3 to 9). The preparation of suitable parenteral formulations under sterile conditions is readily accomplished by standard pharmaceutical techniques well known to those skilled in the art.

The pharmaceutical compositions to be used for in vivo administration should be sterile. This is readily accomplished by, for example, filtration through sterile filtration membranes. Sterile injectable solutions are generally prepared by incorporating the active (e.g., AAV vectors (e.g., ccAAVs), virus capsids, and/or AAV viral particles) in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

The pharmaceutical compositions disclosed herein may also comprise other ingredients such as diluents and adjuvants. Acceptable carriers, diluents and adjuvants are non-toxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycols.

IV. Methods of Use

Any of the compositions (e.g., AAV vectors (e.g., ccAAVs), virus capsids, and/or AAV viral particles) described herein can be used for alleviating and/or treating a disease or a condition. Thus, in some aspects, the present disclosure provides methods for alleviating one or more symptoms and/or for treating a disease or a condition in a subject in need of the treatment by compositions disclosed herein, as well as a pharmaceutical compositions comprising such. In some embodiments, a subject of the methods herein may be a human subject. In some embodiments, the subject may be a subject that has not been previously exposed to wild-type AAV or a recombinant (rAAV) vector. In some embodiments, the subject may be a subject that has not been previously administered a rAAV vector. In some embodiments, the subject is a subject that has been previously administered a rAAV vector, e.g., a rAAV vector described herein. A subject that has been exposed or administered an AAV or rAAV can be identified using methods known in the art, e.g., by PCR detection of viral DNA or by measuring antibody titer to AAV or rAAV, either the capsid or the transgene. In some embodiments, the subject may be a subject that has not been administered an enzyme replacement therapy (e.g., by administration of the enzyme protein). A subject that has been administered an enzyme replacement therapy can be identified using methods known in the art, e.g., by measuring antibody titer to the enzyme. However, in some embodiments the subject has previously been treated with an enzyme replacement therapy. In some embodiments, the subject is a subject that has undergone one or more approaches to clear neutralizing antibodies (NAbs) (e.g., plasmapheresis, immunosuppression, enzymatic degradation). In some embodiments, a subject suitable of methods of use herein may not need to clear neutralizing antibodies (NAbs) before administration of any of the compositions (e.g., AAV vectors (e.g., ccAAVs), virus capsids, and/or AAV viral particles) described herein.

In some embodiments, the subject has or is suspected of having a disease that may be treated with gene therapy. Illustrative diseases or a conditions that can be treated using the methods disclosed herein can include, but are not limited to: cystic fibrosis (cystic fibrosis transmembrane regulator protein) and other diseases of the lung, hemophilia A (Factor VIII), hemophilia B (Factor IX), thalassemia ((β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., a, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping (see, e.g., WO/2003/095647), antisense against U7 snRNAs to induce exon skipping (see, e.g., WO/2006/021724), and antibodies or antibody fragments against myostatin or myostatin propeptide) and Becker, Gaucher disease (glucocerebrosidase), Hurler's disease (a-L-iduronidase), adenosine deaminase deficiency (adenosine deaminase), glycogen storage diseases (e.g., Fabry disease [a-galactosidase] and Pompe disease [lysosomal acid a-glucosidase]) and other metabolic disorders, congenital emphysema (al-antitrypsin), Lesch-Nyhan Syndrome (hypoxanthine guanine phosphoribosyl transferase), Niemann-Pick disease (sphingomyelinase), Tay Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., IIC), serca2a, zinc finger proteins that regulate the phospholamban gene, Barkct, P2-adrenergic receptor, p2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFa soluble receptor), hepatitis (a-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like.

In some embodiments, the AAV vectors, compositions, and methods described herein may be used to treat a kidney disease or a kidney disorder, such as Alport syndrome, benign familial hematuria, polycystic kidney disease (e.g., type 1 or type 2), VonLippel-Lindau disease, Nephrogenic diabetes insipidius, familial hypocalcuric hypercalcemia, nephrolithiasais, hypophosphatemic rickets, Fabray disease, nephronophytis, or steroid resistant nephrotic syndrome.

To perform the methods disclosed herein, an effective amount of the compositions (e.g., AAV vectors (e.g., ccAAVs), virus capsids, and/or AAV viral particles) or a pharmaceutical composition comprising such may be administered to a subject who needs treatment via a suitable route (e.g., intramuscular, intravenous, intracerebroventricular injection, intra-cisterna magna injection, intravitreal, subretinal, subconjuctival, retrobulbar, intracameral, suprachoroidal, intracoronary injection, intraarterial injection, and/or intra-parenchymal injection) at a suitable amount as disclosed herein.

In certain embodiments, the present disclosure also provides for methods of introducing one or more AAV vectors (e.g., ccAAVs) to a cell, comprising contacting the cell with a composition disclosed herein. In some embodiments, methods herein can include delivering one or more AAV vectors (e.g., ccAAVs) herein to a cell, comprising contacting the cell or layer with a viral vector wherein the viral vector comprises an AAV capsid protein variant disclosed herein. In some embodiments of this method, AAV vectors (e.g., ccAAVs) herein can deliver one or more heterologous molecules to a cell. In accordance with these embodiments, AAV vectors (e.g., ccAAVs) herein can deliver one or more therapeutic heterologous molecules to a cell. In some examples, one or more therapeutic heterologous molecules delivered to a cell using the methods herein may be a therapeutic protein, a therapeutic DNA, and/or therapeutic RNA. In some embodiments, the therapeutic protein can be a monoclonal antibody or a fusion protein. In some embodiments, the therapeutic DNA and/or RNA can be an antisense oligonucleotide, siRNA, shRNA, mRNA, a DNA oligonucleotide, and the like.

In certain embodiments, the present disclosure also provides for methods of introducing an AAV vector (e.g., ccAAV) to a CNS tissue, a heart tissue, a kidney tissue, a liver tissue, a skeletal muscle tissue, or any combination thereof, comprising contacting the cell with a virus vector and/or composition disclosed herein. In some embodiments, AAV vectors herein can be delivered to a specific tissue by administering AAV particles having one or more AAV capsid protein variants disclosed herein with enhanced tropism to a CNS tissue, a heart tissue, a kidney tissue, a liver tissue, a skeletal muscle tissue, or any combination thereof.

In some embodiments, methods of administering at least one AAV vector (e.g., ccAAV), virus capsid, and/or AAV viral particle having one or more nucleic acid molecules herein to a tissue substantially modulates expression of the at least one protein and/or gene as compared to baseline. As used herein, "baseline" refers to the expression of the at least one transgene (and the encoded product of the transgene) before the AAV vectors (e.g., ccAAVs) herein were administered. As used herein, "substantially modulates expression" refers to at least a 1-fold change in expression (e.g., increased expression, decreased expression) as compared to baseline. In some embodiments, methods of administering at least one AAV particle or AAV vector (e.g., ccAAVs) having one or more AAV capsid protein variants disclosed herein to a tissue modulates expression of the at least one protein and/or gene as compared to baseline by at least about 2-fold to about 50-fold (e.g., about 2-, 4-, 6-, 8-, 10-, 20-, 30-, 40-, 50-fold). In some embodiments, methods of administering at least one AAV particle or AAV vector having one or more AAV capsid protein variants disclosed herein to a tissue modulates expression of the at least one protein and/or gene as compared to baseline by at least about 2-fold to about 50-fold (e.g., about 2-, 4-, 6-, 8-, 10-, 20-, 30-, 40-, 50-fold) when the at least one AAV particle or AAV vector (e.g., ccAAVs) is delivered to a CNS tissue, a kidney tissue, a heart tissue, a liver tissue, a skeletal muscle tissue, or any combination thereof.

In any of the methods disclosed herein, an effective amount of the compositions (e.g., AAV vectors, viral capsids, AAV particles, AAV genomes, ccAAVs) described herein can be given to a subject in need thereof to alleviate one or more symptoms associated with a disease and or condition. "An effective amount" as used herein refers to a dose of a disclosed composition which is sufficient to confer a therapeutic effect on a subject having a disease and or condition. In some embodiments, an effective amount can be an amount that reduces at least one symptom of disease or condition in the subject.

In some embodiments, methods of administering at 1 least one AAV vector (e.g., ccAAVs) as disclosed herein can have increased gene transfer efficiency in a cell compared to naturally isolated AAV vectors. In some embodiments, methods of administering at least one AAV vector as disclosed herein can have at least about 2-fold to about 50-fold (e.g., about 2-, 4-, 6-, 8-, 10-, 20-, 30-, 40-, 50-fold) increased gene transfer efficiency in a cell compared to naturally isolated AAV vectors. In some embodiments, methods of administering at least one AAV vector as disclosed herein can have increased gene transfer efficiency in a tissue compared to naturally isolated AAV vectors. In some embodiments, methods of administering at least one AAV vector as disclosed herein can have at least about 2-fold to about 50-fold (e.g., about 2-, 4-, 6-, 8-, 10-, 20-, 30-, 40-, 50-fold) increased gene transfer efficiency in a tissue compared to naturally isolated AAV vectors. In some embodiments, methods of administering at least one AAV vector as disclosed herein can have increased gene transfer efficiency in a subject compared to naturally isolated AAV vectors. In some embodiments, methods of administering at least one AAV vector as disclosed herein can have at least about 2-fold to about 50-fold (e.g., about 2-, 4-, 6-, 8-, 10-, 20-, 30-, 40-, 50-fold) increased gene transfer efficiency in a subject compared to naturally isolated AAV vectors.

In some embodiments, methods herein may include administering at least one AAV vector (e.g., ccAAV) to a subject at least once. In some embodiments, methods herein may include administering at least one AAV particle and/or at least one AAV vector to a subject more than once. In some embodiments, methods herein may include administering at least one AAV vector herein to a subject between at least once to at least 10 times (e.g., about 1, 2, 3, 4, 5, 6, 7, 8, 9, 10 times). In some embodiments, methods herein may include administering at least one AAV vector herein to a subject at least twice, at least 3 times, at least 4 times, or at least 5 times. In some embodiments, methods herein may include administering at least one AAV vector herein to a subject once a day, once every other day, once a week, once every two weeks, once every three weeks, once a month, once every other month, once every three months, once every four months, once a year, or twice a year. In some embodiments, methods herein may include administering at least one AAV vector herein to a subject at many times as needed to see the desired response. In some examples, the desired response may be attenuation of at least one symptom of a disease and/or condition in a subject after administration of a dose of an AAV vector herein compared to before administration of the AAV vector. One of skill in the art will appreciate that dosing regimens can be optimized according to disease/condition, disease/condition severity, characteristics of the subject (e.g., age, gender, weight), and the like.

In some embodiments, an AAV vector (e.g., ccAAV) herein can be used for the delivery of cre-recombinase. In some embodiments, an AAV vector (e.g., ccAAV) herein can be used for the delivery of cre-recombinase to result in a conditional activation, a conditional inactivation, an activation, an inactivation, or any combination thereof of one or more genes in a cell, tissue, and/or subject. In accordance with some of these embodiments, an AAV vector (e.g., ccAAV) herein deliver cre-recombinase to one or more specific cell and/or tissue types.

In some embodiments, an AAV vector (e.g., ccAAV) herein can be used for the delivery of a CRISPR-Cas system. The "CRISPR/Cas9" system or "CRISPR/Cas9-mediated gene editing" refers to a type II CRISPR/Cas system that has been modified for genome editing/engineering. It is typically comprised of a "guide" RNA (gRNA) and a non-specific CRISPR-associated endonuclease (Cas9). "Guide RNA (gRNA)" is used interchangeably herein with "short guide RNA (sgRNA)" or "single guide RNA (sgRNA). The sgRNA is a short synthetic RNA composed of a "scaffold" sequence necessary for Cas9-binding and a user-defined~20 nucleotide "spacer" or "targeting" sequence which defines the genomic target to be modified. The genomic target of Cas9 can be changed by changing the targeting sequence present in the sgRNA.

In some embodiments, an AAV vector comprises a vector genome, wherein the vector genome encodes a gene-editing molecule. In some embodiments, the gene-editing molecule is a nuclease. In some embodiments, the nuclease is a Cas9 nuclease. In some embodiments, the nuclease is a Cas12a nuclease. In some embodiments, the gene editing molecule is a sgRNA.

V. Kits

The present disclosure also provides kits for use in preparing any one of the compositions (e.g., AAV vectors, AAV particles, AAV genomes, viral capsids, ccAAVs) as described herein and kits having one or more therapeutic uses as described herein. A kit for use as described herein may include one or more containers further including a composition (e.g., AAV vectors, AAV particles, AAV genomes, viral capsids, ccAAVs) as described herein, formulated in a pharmaceutical composition.

In some embodiments, the kit can additionally comprise instructions for use of compositions (e.g., AAV vectors, AAV particles, AAV genomes, viral capsids, ccAAVs) in any of the methods described herein. The included instructions may include a description of administration of the compositions or a pharmaceutical composition comprising such to a subject to achieve the intended activity in a subject. The kit may further comprise a description of selecting a subject suitable for treatment based on identifying whether the subject is in need of the treatment. The instructions relating to the use of the compositions as described herein generally include information as to dosage, dosing schedule, and route of administration for the intended treatment.

The containers may be unit doses, bulk packages (e.g., multi-dose packages) or subunit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiments, the disclosure provides articles of manufacture comprising contents of the kits described above.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit, and scope of the present disclosure. All such modifications are intended to be within the scope of the disclosure.

Example 1. Cross-Species Evolution of AAV Capsids

The method for generating coevolved AAV capsid protein variants is as follows. The first step involved identification of conformational 3D antigenic epitopes on the AAV9 capsid surface using cryo-electron microscopy. AAV9 libraries were then engineered through saturation mutagenesis of amino acid residues identified within the surface loops. Specifically, amino acid residues within variable region IV (452-NGSGQNQ-458; SEQ ID NO: 38) and within variable region VIII (586-SAQAQAQ-592; SEQ ID NO: 39) were selected for saturation mutagenesis and generation of two different AAV libraries—a variable region IV (VR4) AAV parental library and a variable region VIII (VR8) parental library. Selected residues within the antigenic motifs were subjected to mutagenesis using degenerate primers with each codon substituted by nucleotides NNK and gene fragments combined together by Gibson assembly (a sequence overlap-based method). Specifically, to generate AAV VR4 (variable region IV) and VR8 (variable region VIII) libraries, oligonucleotides containing a 21-mer (NNRNNRNNRNNRNNRNNRNNR; SEQ ID NO: 124) and homology arms to AAV9 Cap gene were synthesized through Integrated DNA Technologies wherein "N" corresponds to any nucleotide (A, T, G, C) and "R" corresponds to either a G or C to prevent premature stop codon generation in the capsid library.

The resulting capsid-encoding genes containing a degenerate library of mutated antigenic motifs were cloned into a wild type AAV genome to replace the original Cap encoding DNA sequence, yielding a plasmid library. Specifically, the plasmid contained genes encoding AAV2 Rep and AAV9 Cap flanked by AAV2 ITRs, with amino acids in the AAV9 Cap mutated to stop codons to reduce wild-type AAV9 plasmid contamination.

The VR4 and VR8 parental plasmid libraries were then transfected into HEK 293 producer cell lines with an adenoviral helper plasmid to generate AAV VR4 capsid and AAV VR8 capsid parental libraries. In brief, HEK293 cells were transfected at 70 to 80% confluence with polyethylenimine with equal molar ratios of pTR-AAV9-Library and adenovirus helper plasmid pXX680. HuH7 (human hepato cellular carcinoma) cells were cultured to ~75% confluence and infected overnight with the AAV9 libraries at 5,000 viral genomes per cell. The following day, the culture medium was replaced with medium containing Ad5 at a multiplicity of infection (MOI) of 0.5. At 50% to 75% cytopathic effect, the supernatant was collected and incubated at 55° C. for 30 minutes to inactivate the Ad5. DNase I-resistant viral genomes in the media were quantified and served as the inoculum for the subsequent round of infection.

Cross-Species In vivo AAV Capsid Screening. In order to select for new AAV9 strains that can escape neutralizing antibodies (NAbs), target the central nervous system (CNS), and/or act in a more potent manner than naturally occurring AAV9, the AAV libraries prepared as described above were subjected to multiple rounds or "cycles" of infection in three different mammalian species. In the first cycle, AAV VR4 capsid parental libraries or AAV VR8 capsid parental libraries prepared as described above were intravenously (i.v.) injected into 4 week old piglets at about $3\times10^{13}$ to $5\times10^{13}$ vg/kg (viral genomes/kilogram). Pigs were sacrificed 6 days post injection and viral DNA was amplified via PCR from genomic DNA extracted from various brain regions (cerebellum, frontal, temporal, parietal, occipital cortices, hippocampus, thalamus, and midbrain) using oligonucleotides targeting the VR4 or VR8 flanking DNA sequences were used to amplify the AAV library sequences. In brief, to amplify evolved AAV libraries from this first cycle, DNase I-resistant viral genomes were isolated from the harvested pig brain tissues and amplified by Q5 polymerase for 10 to 18 cycles using primers 5'-CCCTACACGACGCTCTTCC-GATCTNNNNNGTACCTGTACTACTTGTCTCG-3' (SEQ ID NO: 42) and 5'-GACTGGAGTTCA-GACGTGTGCTCTTCCGATCAGACCAT-ACCGGGTAAG-3' (SEQ ID NO: 43) for variable regions IV and VIII.

The Illumina MiSeq sequencing adaptor for multiplexing was added in a second round of PCR using Q5 polymerase with the primers. After each round of PCR, the products were purified using the PureLink PCR Micro kit (Invitrogen). The quality of the amplicons was verified using a Bioanalyzer (Agilent), and concentrations were quantified using a Qubit spectrometer (Invitrogen). PCR amplicons containing the VR4 or VR8 libraries, as determined by Sanger sequencing, were then pooled together and used to generate the next library preparation.

The resulting amplicons were then cloned back into vectors to generate an evolved plasmid library using the same method as generating the parental plasmid library except that instead of using Gibson assembly, the amplicons were assembled using multiple-overlap-extension PCR. The VR4 and VR8 parental plasmid libraries were then transfected into HEK 293 producer cell lines with an adenoviral helper plasmid to generate AAV VR4 capsid and AAV VR8 capsid evolved libraries using the same method described above. DNase I-resistant viral genomes in the media were quantified and served as the inoculum for the subsequent round of infection.

In the second cycle following evolution in pigs, AAV VR4 capsid parental libraries or AAV VR8 capsid evolved libraries prepared as described above were intravenously (i.v.) injected into 8 week C57/B6 mice at about $3 \times 10^{13}$ to $5 \times 10^{13}$ vg/kg. Mice were sacrificed 6 days post injection and viral DNA was amplified via PCR from genomic DNA extracted from various brain regions (cerebellum, frontal, temporal, parietal, occipital cortices, hippocampus, thalamus, and midbrain) using oligonucleotides targeting the VR4 or VR8 flanking DNA sequences were used to amplify the AAV library sequences as described above. The resulting amplicons were then cloned back into vectors to generate another evolved plasmid library using the same method as generating the first evolved plasmid library above. This time the viral genomes in the media were quantified and served as the inoculum for the third cycle.

Following evolution in pigs and mice, the evolved VR4 and VR8 libraries were intravenously (i.v.) injected into 2 year old non-human primates (NHPs) at about $110^{13}$ to $3 \times 10^{13}$ vg/kg. Viral DNA was amplified from genomic DNA extracted from various brain regions in NHPs as described above. Amplified viral DNA was subjected to high-throughput sequencing using the Illumina MiSeq platform and the resulting data was analyzed as follows.

Demultiplexed reads were subjected to a quality control check using FastQC (v.0.11.5), with no sequences flagged for poor quality, and analyzed via a custom Perl script using methods similar to those described in Tse et al., *PNAS*, 2017 Jun. 13; 114(24):E4812-E4821, the disclosure of which is incorporated herein in its entirety. In brief, raw sequencing files were probed for mutagenized regions of interest, and the frequencies of different nucleotide sequences in this region were counted and ranked for each library. Nucleotide sequences were also translated, and these amino acid sequences were similarly counted and ranked. Amino acid sequence frequencies across libraries were then plotted in the R graphics package v3.5.2. A second Perl script was used to calculate the amino acid representation at each position in each library, taking into account the contribution of each mutant in the library.

Subjecting these libraries to multiple rounds of evolution between three species (pig, mouse, and NHP (i.e., monkey)) yielded several AAV9 capsid variants. The AAV9 capsid variants resulting from the cross-species in vivo screening with the highest frequency were sequenced. Bubble plots showed library diversity, directed evolution and enrichment of novel antigenic footprints in the VR8 region and the VR4 region between the parental libraries (FIG. 1A) and evolved libraries after three cycles between three different species (FIG. 1B). Substitutions present in these AAVs in either region IV (452-NGSGQNQ-458; SEQ ID NO: 38) or region VIII (586-SAQAQAQ-592; SEQ ID NO: 39) are shown in Table 5.

TABLE 5

| AAV9 Mutant Capsid Protein | Region of Amino Acid Substitution | Amino Acid Substitution Sequence |
|---|---|---|
| AAV.cc41 | IV (452-458) | EGGTVHA (SEQ ID NO: 20) |
| AAV.cc42 | IV (452-458) | FYGTDSA (SEQ ID NO: 21) |
| AAV.cc43 | IV (452-458) | HGQSASR (SEQ ID NO: 22) |
| AAV.cc44 | IV (452-458) | DTPTNQA (SEQ ID NO: 23) |
| AAV.cc45 | IV (452-458) | ITRQAYQ (SEQ ID NO: 24) |
| AAV.cc46 | IV (452-458) | RMFKSNQ (SEQ ID NO: 25) |
| AAV.cc47 | IV (452-458) | GVSLGGG (SEQ ID NO: 26) |
| AAV.cc48 | IV (452-458) | KHFLQGE (SEQ ID NO: 27) |
| AAV.cc49 | IV (452-458) | MGRERAG (SEQ ID NO: 28) |
| AAV.cc81 | VIII (586-592) | LNSSVPS (SEQ ID NO: 29) |
| AAV.cc82 | VIII (586-592) | YMDHQVS (SEQ ID NO: 30) |
| AAV.cc83 | VIII (586-592) | TSDSLVS (SEQ ID NO: 31) |
| AAV.cc84 | VIII (586-592) | NAVGALS (SEQ ID NO: 32) |
| AAV.cc85 | VIII (586-592) | MPISHHE (SEQ ID NO: 33) |
| AAV.cc86 | VIII (586-592) | DSGARGA (SEQ ID NO: 34) |
| AAV.cc87 | VIII (586-592) | NVALALG (SEQ ID NO: 35) |
| AAV.cc88 | VIII (586-592) | GALRMGM (SEQ ID NO: 36) |
| AAV.cc89 | VIII (586-592) | LSGEGAV (SEQ ID NO: 37) |

Example 2. In Vivo Characterization of Recombinant AAVs in Mice

Three recombinant capsid proteins, AAV.cc47 (SEQ ID NO: 8), AAV.cc44 (SEQ ID NO: 5), AAV.cc81 (SEQ ID NO: 11), and AAV.cc84 (SEQ ID NO: 14)—collectively referred to in this example as "ccAAV vectors"—were selected for in vivo characterization in mice. Next, recombinant AAVs comprising these capsid proteins or native AAV9 and packaging of a fluorescent transgene were generated. In brief, the recombinant capsid proteins produced as vectors packaging either CBh-GFP (AAV.cc81 and AAV.cc84) or CBh-mCherry (AAV.cc47 and AAV.cc44). In brief, recombinant AAV vectors were produced by transfecting HEK293 cells at 70 to 80% confluence with polyethylenimine using the triple-plasmid transfection protocol. Recombinant vectors packaging single-stranded genomes encoding green fluorescence protein driven by a hybrid chicken β-actin promoter (CBh-eGFP), cherry (red) fluorescence protein driven by a hybrid chicken β-actin promoter (CBh-mCherry), or a self-complementary AAV9 driven by either CBh-eGFP or CBh-mCherry were generated using this method. See, in general, FIGS. 29A-29B. Subsequent steps involving the harvesting of recombinant AAV vectors and downstream purification were carried out. In brief, vector purification was carried out using iodaxinol gradient ultracentrifugation protocol, buffer exchange and concentration using vivaspin2 100 kDa molecular weight cut-off (MWCO) centrifugation columns (F-2731-100 Bioexpress). Recombinant AAV vector titers were determined by quantitative PCR with primers amplifying AAV2 inverted terminal repeat regions (ITRs) 5'-AACATGCTACGCAGAGAGGGAGTGG-3' (SEQ ID NO: 44) and 5'-CATGAGACAAGGAACCCCTAGTGATGGAG-3' (SEQ ID NO: 45).

Figure 2A:
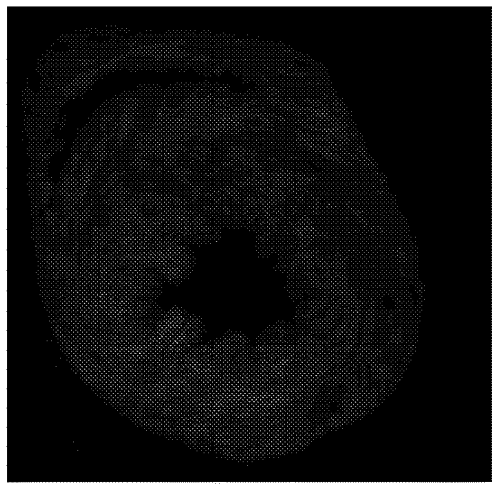
FIGS. 2A-2D illustrate mCherry reporter gene expression in C57/B6 mouse heart in accordance with certain embodiments herein. Representative fluorescent microscopy images showing mCherry expression in heart vibratome sections 24 hours post-fixation with 4% PFA in mice infected with AAV9 (FIG. 2A) or AAV.cc47 (FIG. 2B).
Figure 2B:
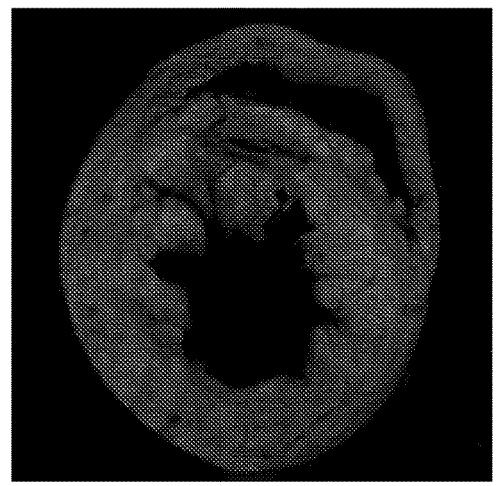
Figure 2C:
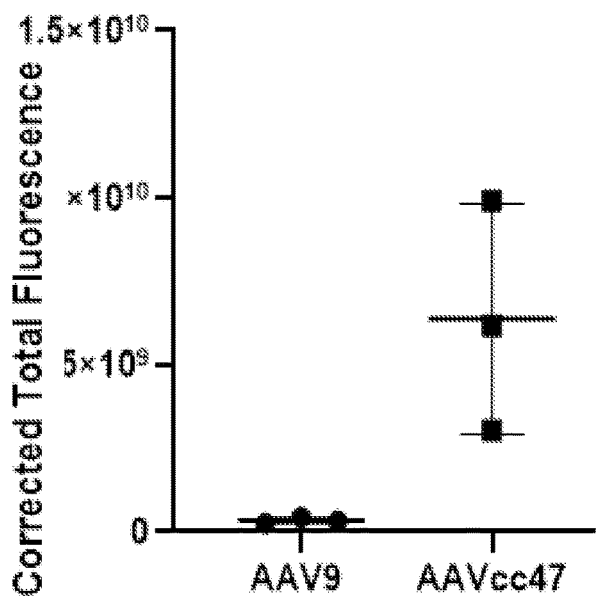
Figure 2D:
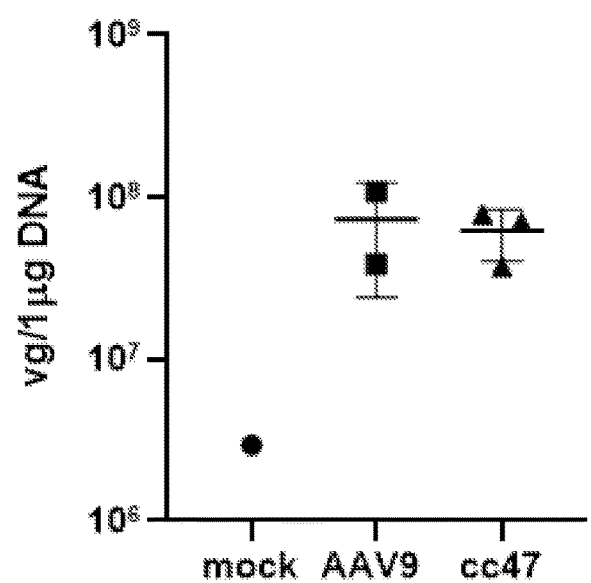
Figure 26A:
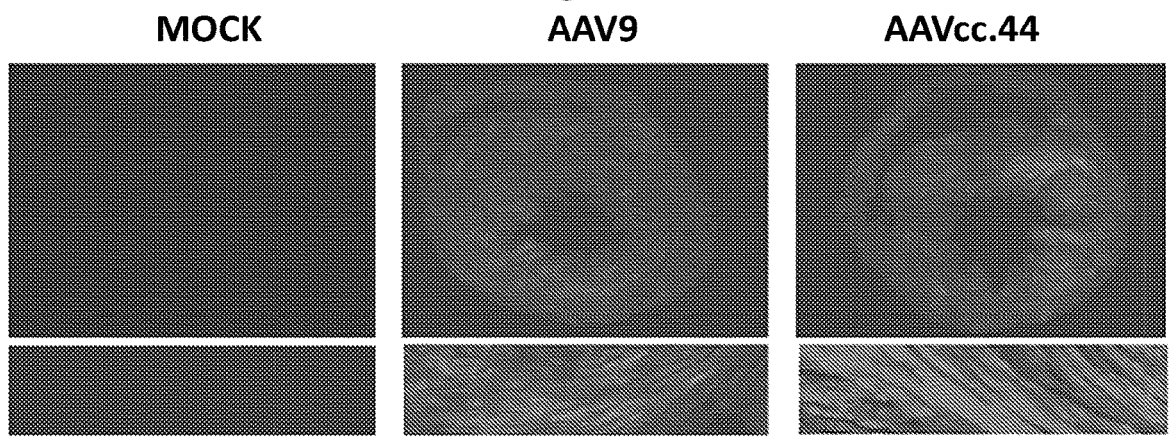
FIGS. 26A-26B illustrate mCherry reporter gene expression in C57/B6 mouse heart in accordance with certain embodiments herein.
Figure 26B:
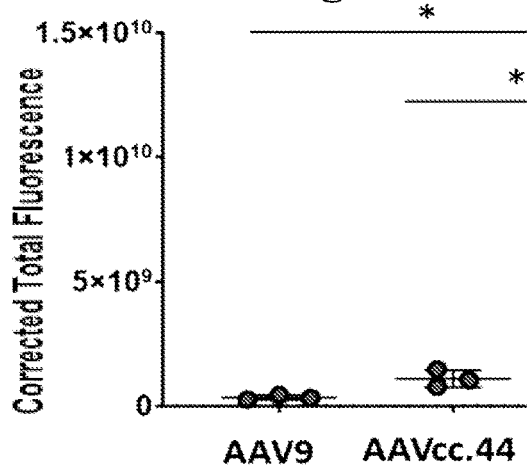

C57/BL6 mice were injected intravenously at a dose of $5 \times 10^{13}$ vg/kg per mouse with either a self-complementary AAV9 or one of the ccAAV vectors. Mice were sacrificed 4 weeks post injection and multiple organs harvested and transduction was evaluated by native fluorescence or immunohistochemistry (IHC). FIGS. 2A-2B provide representative images showing mCherry expression of AAV9 (FIG. 2A) and AAV.cc47 (FIG. 2B) in vibratome sections of the heart after 24 hours post-fixation with 4% PFA. FIG. 2C provides quantitative analysis of the corrected total fluorescence wherein mice infected with the AAV.cc47 had a more robust expression of mCherry in heart tissues compared to mice infected with AVV9 vectors. FIG. 2D provides vector biodistribution of AAV9 and AAV.cc47 in the heart tissues of the mice. FIGS. 6A-6C provide representative images showing GFP expression of AAV9 (FIG. 6A), AAV.cc81 (FIG. 6B), and AAV.cc84 (FIG. 6C) in vibratome sections of the heart after 24 hours post-fixation with 4% PFA. FIG. 6D provides quantitative analysis of the corrected total fluorescence wherein mice infected with the AAV.cc84 had a more robust expression of GFP in heart tissues compared to mice infected with AAV.cc81 or AVV9 vectors. FIG. 26A provides representative images showing mCherry expression of AAV9 and AAV.cc44 in vibratome sections of the heart after 24 hours post-fixation with 4% PFA, and FIG. 26B provides quantitative analysis of the corrected total fluorescence.

Figure 3A:
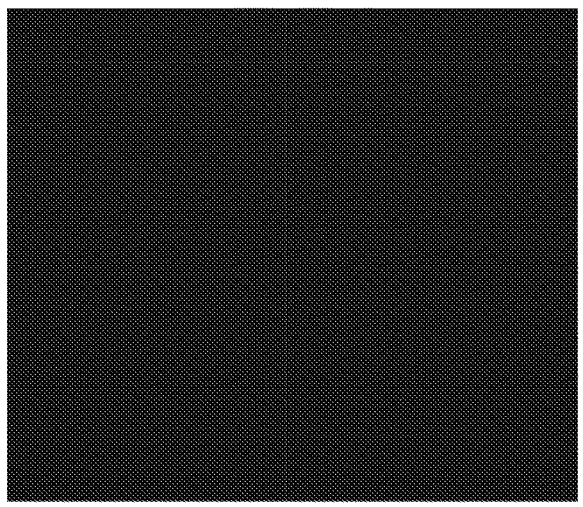
FIGS. 3A-3C illustrate mCherry reporter gene expression in C57/B6 mouse skeletal muscle in accordance with certain embodiments herein. Representative fluorescent microscopy images showing mCherry expression in skeletal muscle vibratome sections 24 hours post-fixation with 4% PFA in mice infected with AAV9 (FIG. 3A) or AAV.cc47 (FIG. 3B).
Figure 3B:
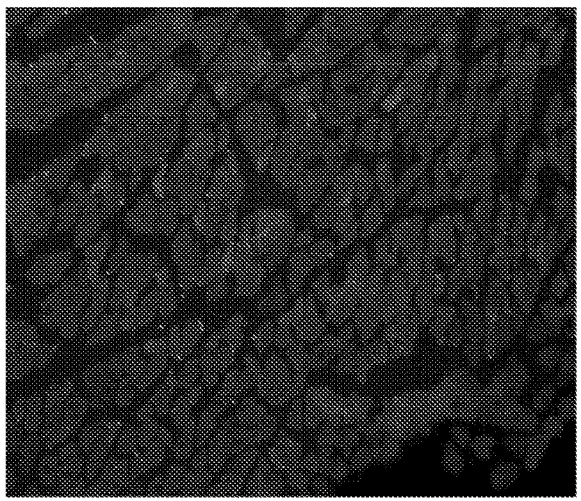
Figure 3C:
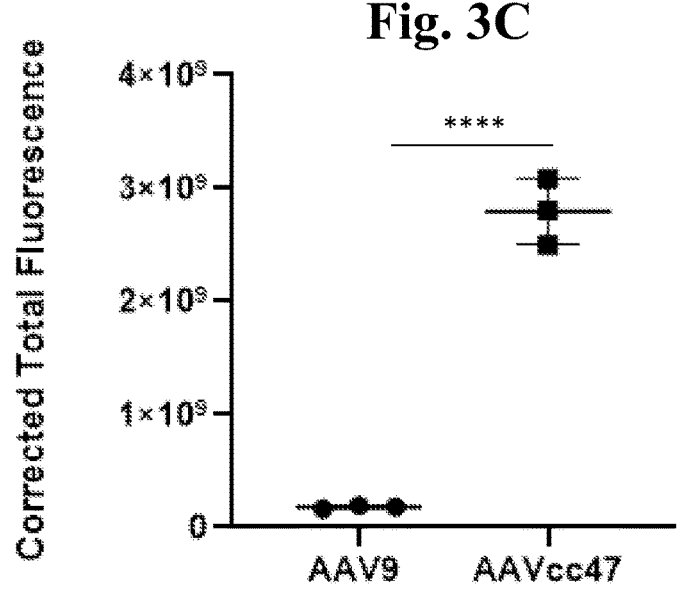
Figure 7A:
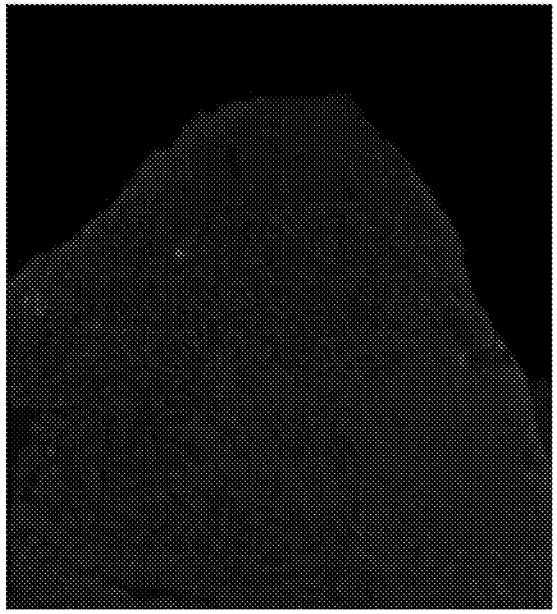
FIGS. 7A-7C illustrate GFP reporter gene expression in C57/B6 mouse skeletal muscle in accordance with certain embodiments herein. Representative fluorescent microscopy images showing GFP expression in skeletal muscle vibratome sections 24 hours post-fixation with 4% PFA in mice infected with AAV9 (FIG. 7A) or AAV.cc81 (FIG. 7B).
Figure 7B:
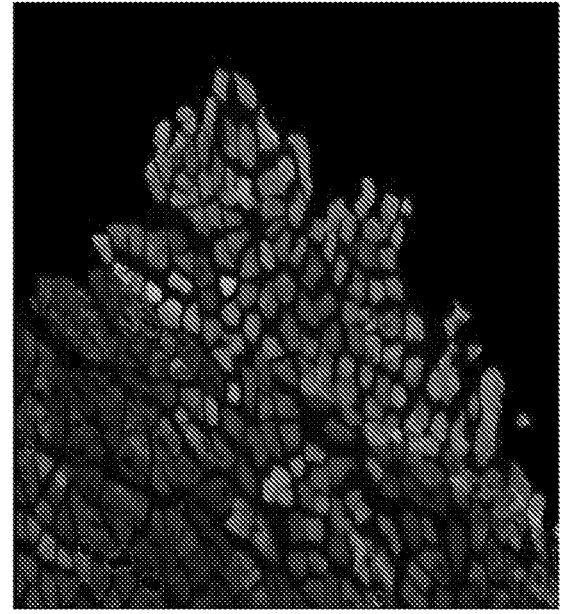
Figure 7C:
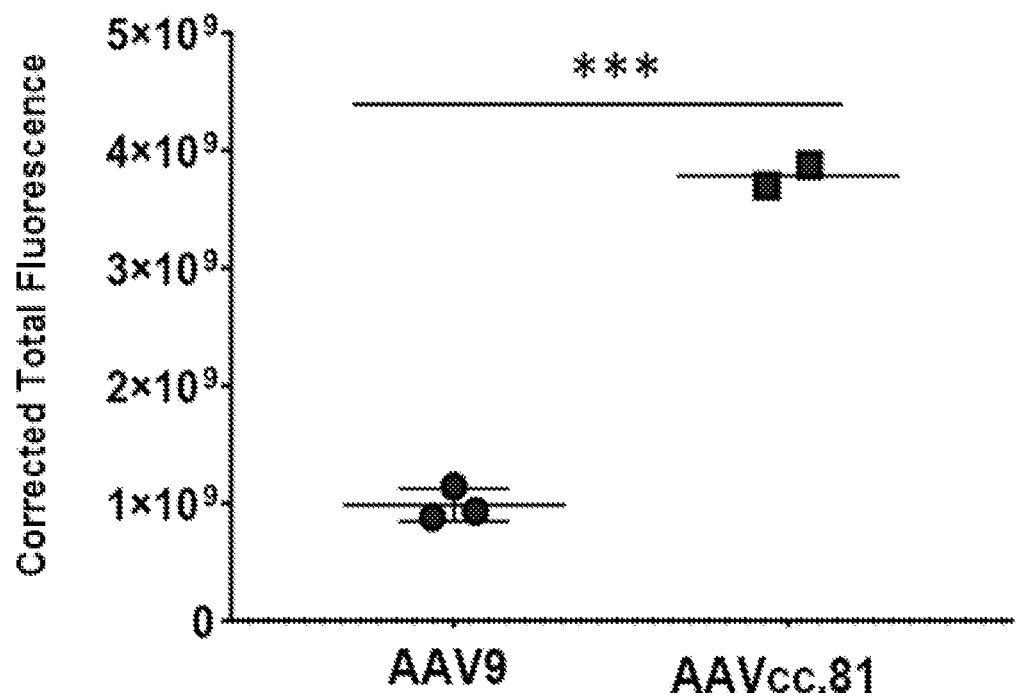
Figure 26D:
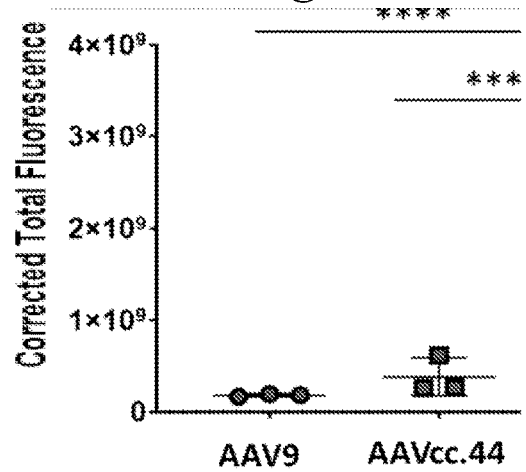
FIGS. 26C-26D illustrate mCherry reporter gene expression in C57/B6 mouse skeletal muscle in accordance with certain embodiments herein.
Figure 26C:
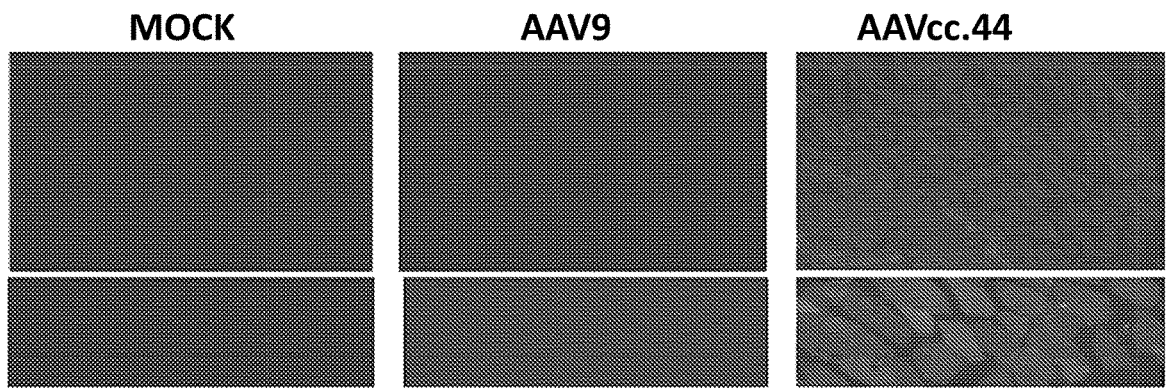

FIGS. 3A-3B provide representative images showing mCherry expression of AAV9 (FIG. 3A) and AAV.cc47 (FIG. 3B) in vibratome sections of skeletal muscle after 24 hours post-fixation with 4% PFA. FIG. 3C provides quantitative analysis of the corrected total fluorescence wherein mice infected with the AAV.cc47 had a more robust expression of mCherry in skeletal muscle compared to mice infected with AVV9 vectors. FIGS. 7A-7B provide representative images showing GFP expression of AAV9 (FIG. 7A) and AAV.cc81 (FIG. 7B) in vibratome sections of skeletal muscle after 24 hours post-fixation with 4% PFA. FIG. 7C provides quantitative analysis of the corrected total fluorescence wherein mice infected with the AAV.cc81 had a more robust expression of GFP in skeletal muscle compared to mice infected with AVV9 vectors. FIG. 26C provides representative images showing mCherry expression of AAV9 and AAV.cc44 in vibratome sections of skeletal muscle after 24 hours post-fixation with 4% PFA, and FIG. 26D provides quantitative analysis of the corrected total fluorescence.

Figure 4A:
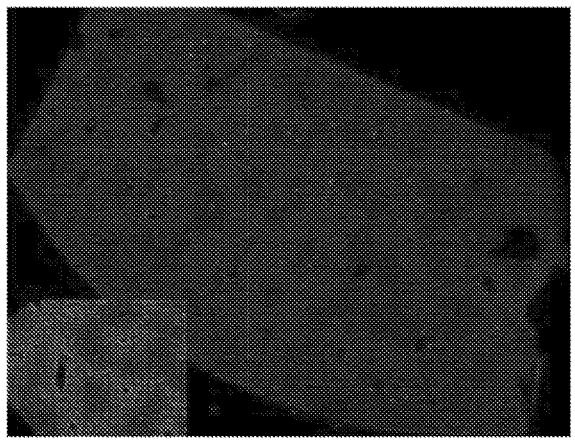
FIGS. 4A-4D illustrate mCherry reporter gene expression in C57/B6 mouse liver in accordance with certain embodiments herein. Representative fluorescent microscopy images showing mCherry expression in liver vibratome sections 24 hours post-fixation with 4% PFA in mice infected with AAV9 (FIG. 4A) or AAV.cc47 (FIG. 4B).
Figure 4B:
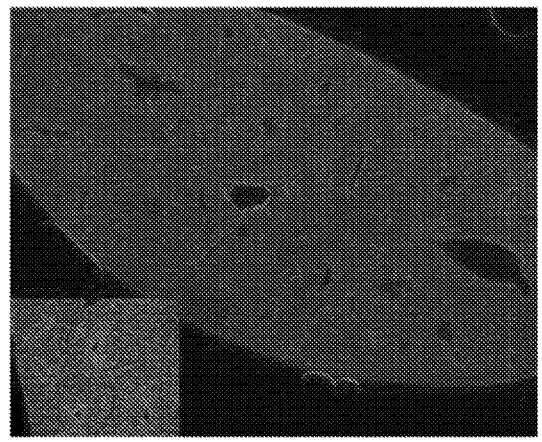
Figure 4C:
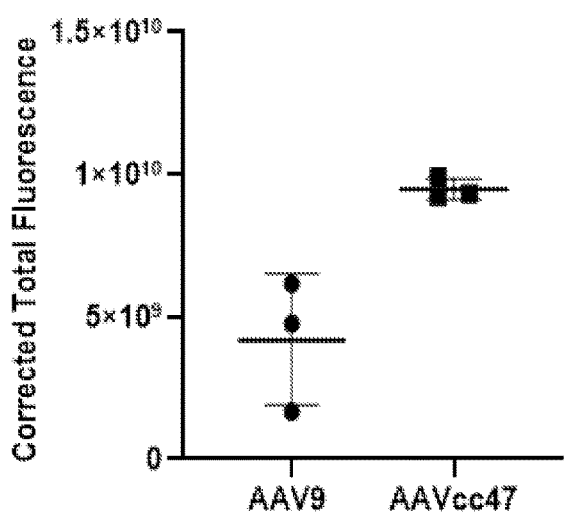
Figure 4D:
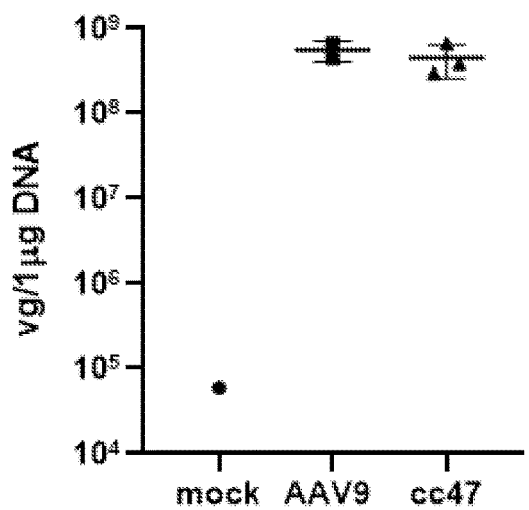
Figure 8A:
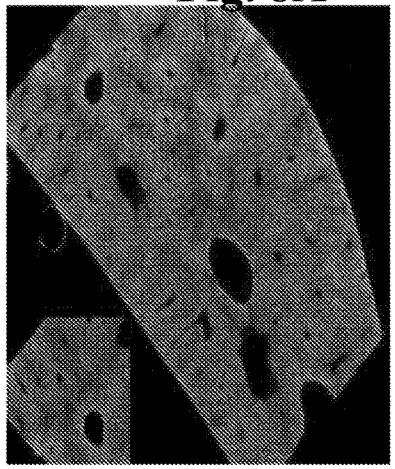
FIGS. 8A-8D illustrate GFP reporter gene expression in C57/B6 mouse liver in accordance with certain embodiments herein. Representative fluorescent microscopy images showing GFP expression in liver vibratome sections 24 hours post-fixation with 4% PFA in mice infected with AAV9 (FIG. 8A), AAV.cc481 (FIG. 8B), or AAV.cc84 (FIG. 8C).
Figure 8B:
Figure 8C:
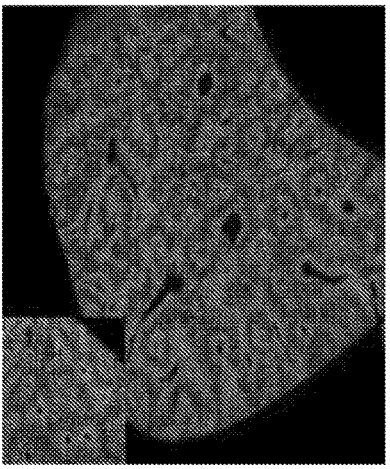
Figure 8D:
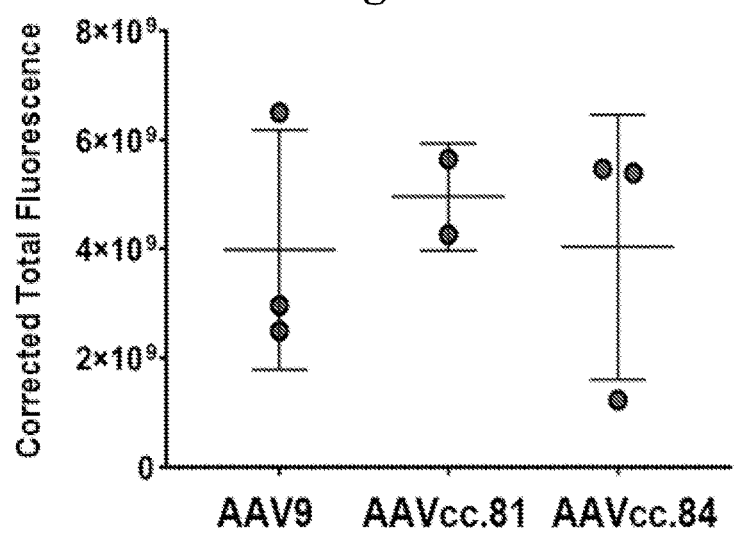
Figure 10A:
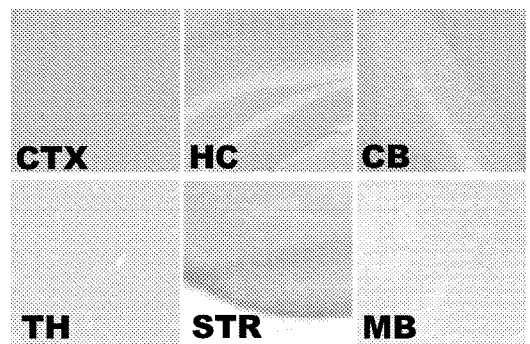
FIGS. 10A-10E illustrate fluorescence reporter expression as assessed by immunohistochemistry (IHC) in C57/B6 mouse brain regions in accordance with certain embodiments herein.
Figure 10B:
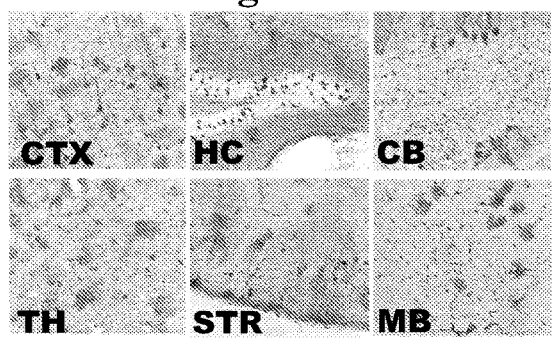
Figure 10C:
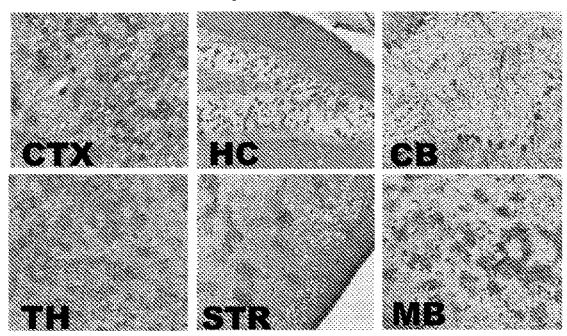
Figure 10D:
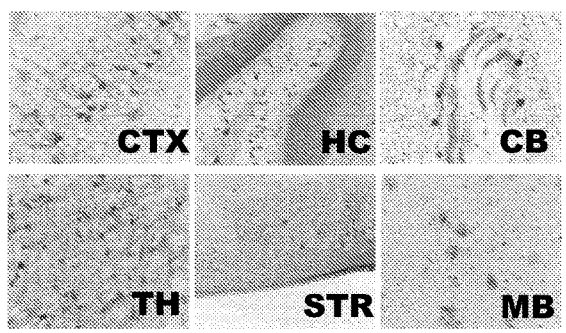
Figure 10E:
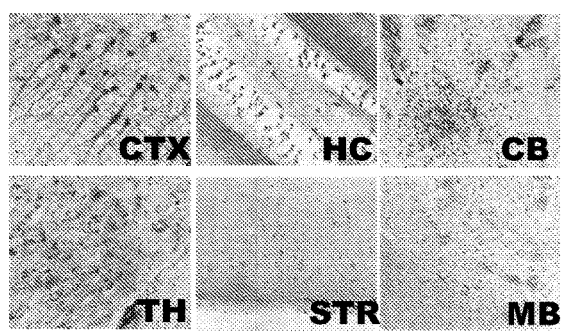
Figure 11A:
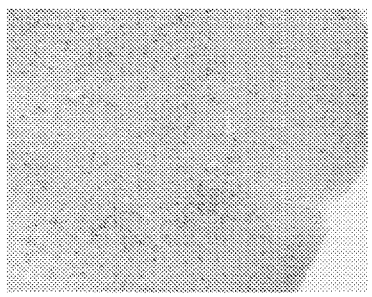
FIGS. 11A-11G illustrate AVV.cc47 transduction assessed by immunohistochemistry (IHC) in pig brain regions in accordance with certain embodiments herein.
Figure 11B:
Figure 11C:
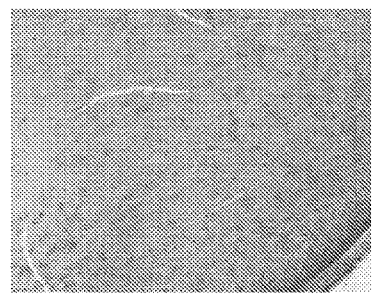
Figure 11D:
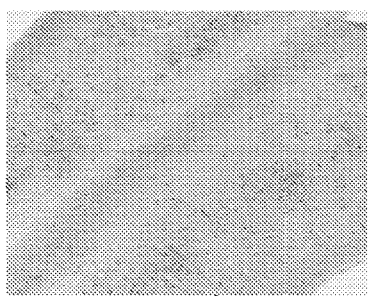
Figure 11E:
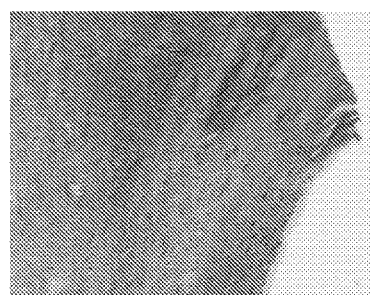
Figure 11F:
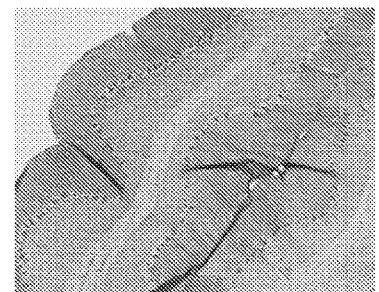
Figure 11G:
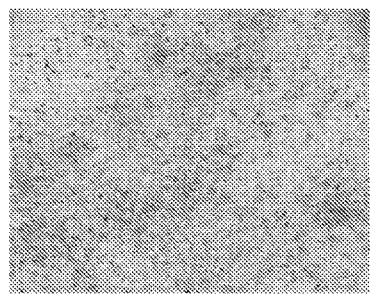
Figure 12A:
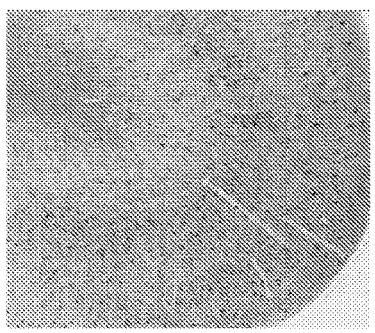
FIGS. 12A-12G illustrate AVV.cc84 transduction assessed by immunohistochemistry (IHC) in pig brain regions in accordance with certain embodiments herein.
Figure 12B:
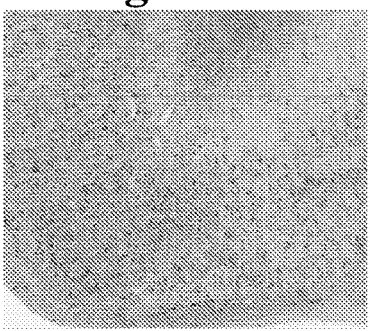
Figure 12C:
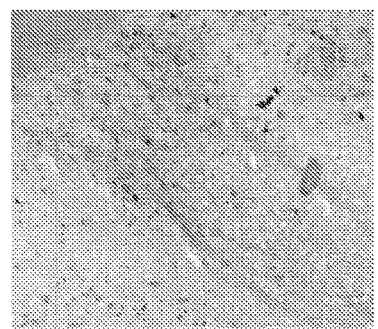
Figure 12D:
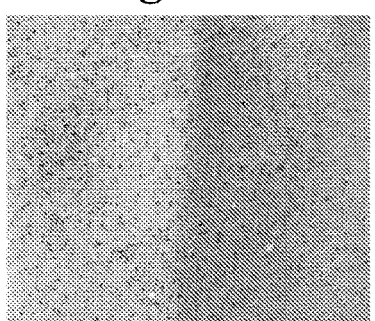
Figure 12E:
Figure 12F:
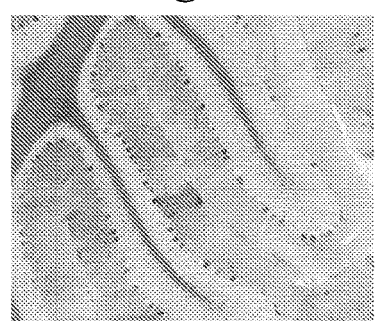
Figure 12G:
Figure 27A:
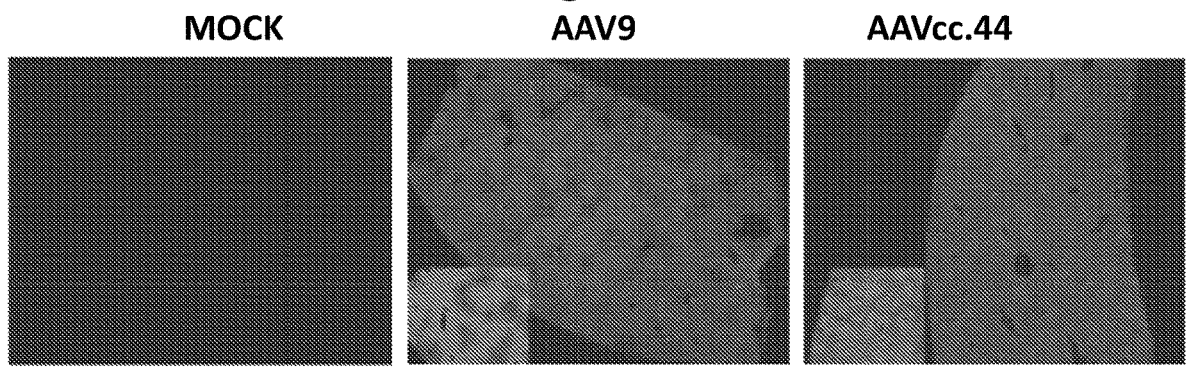
FIGS. 27A-27B illustrate mCherry reporter gene expression in C57/B6 mouse liver in accordance with certain embodiments herein.
Figure 27B:
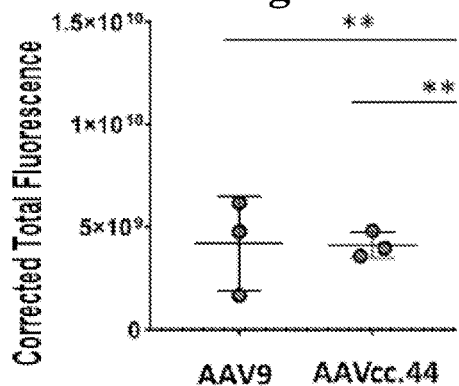

FIGS. 4A-4B provide representative images showing mCherry expression of AAV9 (FIG. 4A) and AAV.cc47 (FIG. 4B) in vibratome sections of liver after 24 hours post-fixation with 4% PFA. FIG. 4C provides quantitative analysis of the corrected total fluorescence in the liver of mice infected with the AAV.cc47 and AVV9 vectors. FIG. 4D provides vector biodistribution of AAV9 and AAV.cc47 in the liver tissues of the mice. FIGS. 8A-8C provide representative images showing GFP expression of AAV9 (FIG. 8A), AAV.cc81 (FIG. 8B), and AAV.cc84 (FIG. 8C) in vibratome sections of the liver after 24 hours post-fixation with 4% PFA. FIG. 8D provides quantitative analysis of the corrected total fluorescence wherein mice infected with either AAV.cc84, AAV.cc81 or AVV9 vectors did not show a robust expression of GFP in the liver. FIG. 27A provides representative images showing mCherry expression of AAV9 and AAV.cc44 in vibratome sections of liver after 24 hours post-fixation with 4% PFA, and FIG. 27B provides quantitative analysis of the corrected total fluorescence.

Figure 27D:
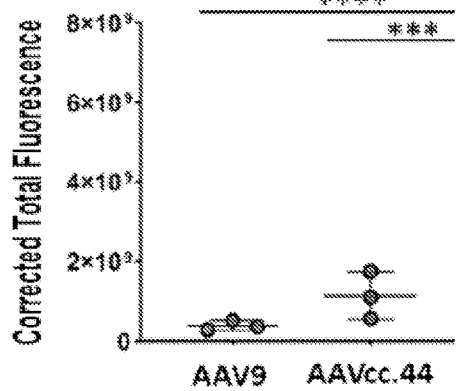
FIGS. 27C-27D illustrate mCherry reporter gene expression in C57/B6 mouse kidney in accordance with certain embodiments herein.
Figure 27C:
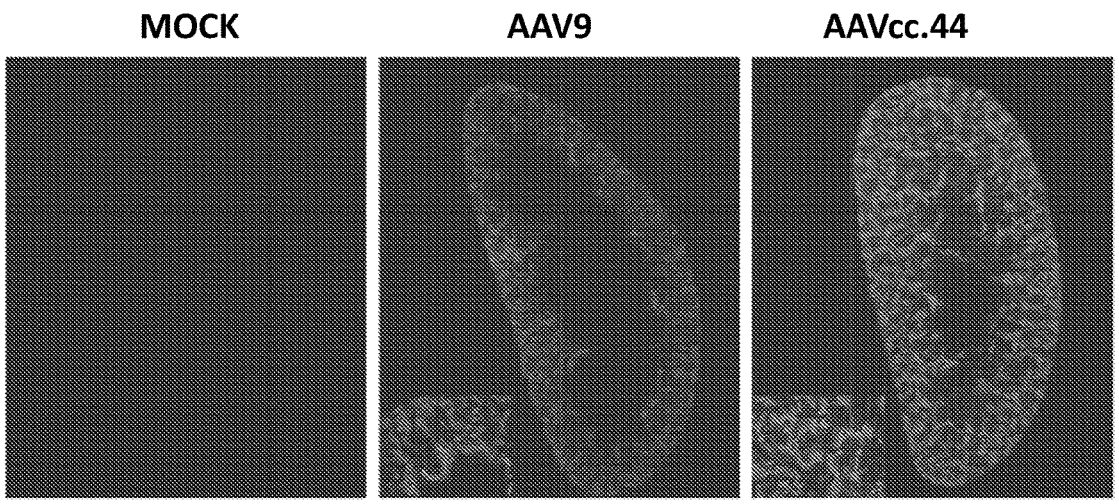

FIGS. 5A-5B provide representative images showing mCherry expression of AAV9 (FIG. 5A) and AAV.cc47 (FIG. 5B) in vibratome sections of kidney tissues after 24 hours post-fixation with 4% PFA. FIG. 5C provides quantitative analysis of the corrected total fluorescence wherein mice infected with the AAV.cc47 had a more robust expression of mCherry in kidney compared to mice infected with AVV9 vectors. FIGS. 9A-9B provide representative images showing GFP expression of AAV9 (FIG. 9A) and AAV.cc81 (FIG. 9B) in vibratome sections of skeletal muscle after 24 hours post-fixation with 4% PFA. FIG. 9C provides quantitative analysis of the corrected total fluorescence wherein mice infected with the AAV.cc81 had a more robust expression of GFP in skeletal muscle compared to mice infected with AVV9 vectors. FIG. 27C provides representative images showing mCherry expression of AAV9 and AAV.cc47 in vibratome sections of kidney tissues after 24 hours post-fixation with 4% PFA, and FIG. 27D provides quantitative analysis of the corrected total fluorescence.

Brain slices were harvested from the mice 4 weeks after injected intravenously at a dose of $5 \times 10^{13}$ vg/kg per mouse with either a self-complementary AAV9 or one of the ccAAV vectors and AAV vector expression was examined in specific sections of the brain using immunohistochemistry to detect either mCherry or GFP. As shown in FIGS. 10A-10E, and FIGS. 28A-28C all vectors showed localization in the brain tissue, however, the robustness of ccAAV vector expression varied by brain region depending on the variant type.

Collectedly, the data in this example herein showed that evolved capsid variant proteins enriched for CNS tissues had improved tropism toward the brain even after systemic injection into the mouse. Additionally, evolved ccAAV vectors showed strong expression in other, non-CNS tissues including heart, skeletal muscle, and to some extent, liver. A surprising discovery was that the evolved AVV.cc47 vector, which had amino acid substitutions at VR4 only, showed high levels of transducing expression of mCherry in the kidney. To date, there are no known AAV vectors capable of having high transduction efficiency in the kidney and, of the ccAAV vectors tested, only AAV.cc47 showed this phenotype (AAV.cc81 and AAVcc.84—both having amino acid substitutions within VR8—failed to transduce expression in the kidney).

Example 3. In Vivo Characterization of Recombinant AAVs in Pigs

The ccAAV vectors packaging a fluorescence reporter gene used in example 2 herein were also used in example 3. Herein, newly weaned piglets weighing approximately 7 kg were injected at 3 weeks of age by intrathecal infusion at a dose of $3 \times 10^{13}$ vg per pig of about 7 kg (in 2 ml) with a self-complementary AAV9 or ccAAV vectors. Piglets were sacrificed 4 weeks post injection and the brain, spinal cord, heart, and liver were harvested. Transduction was evaluated by native fluorescence or by IHC performed as described herein.

Figure 13A:
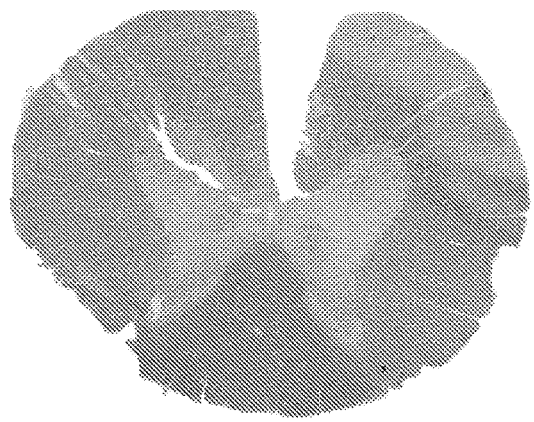
FIGS. 13A-13F illustrate AAV.cc47 and AVV.cc84 transduction in pig spinal cord in accordance with certain embodiments herein. A section of the pig spinal cord was subjected to IHC staining for AVV.cc47 (FIG. 13A) and AVV.cc84 (FIG. 13B) in the tissue. mCherry fluorescence was measured in white matter (FIG. 13C) and grey matter (FIG. 13E) to assess for AVV.cc47. GFP fluorescence was measured in white matter (FIG. 13D) and grey matter (FIG. 13FE) to assess for the presence of AVV.cc84.
Figure 13B:
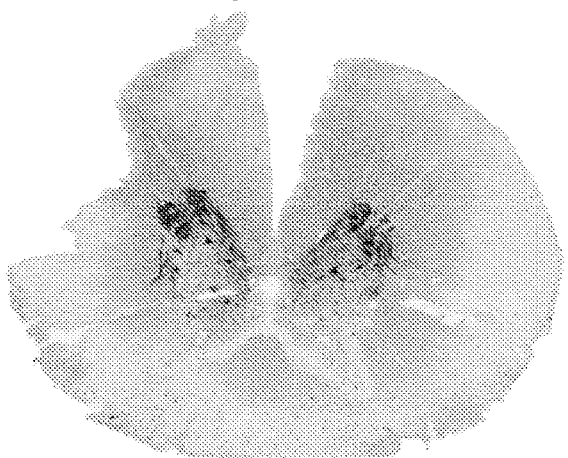
Figure 13C:
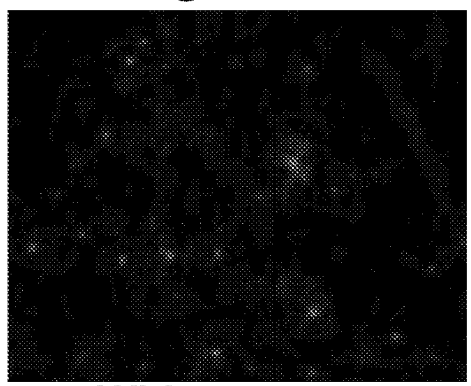
Figure 13D:
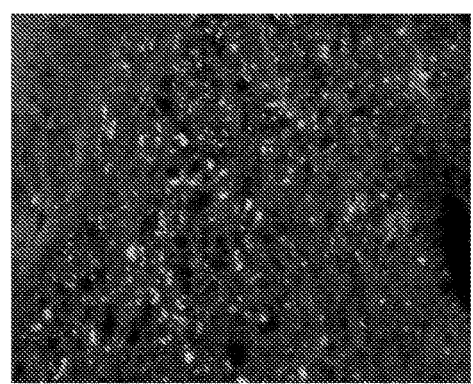
Figure 13E:
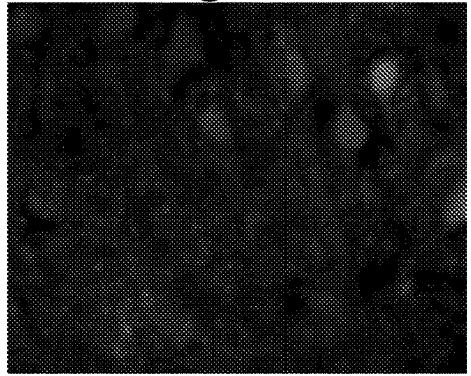
Figure 13F:
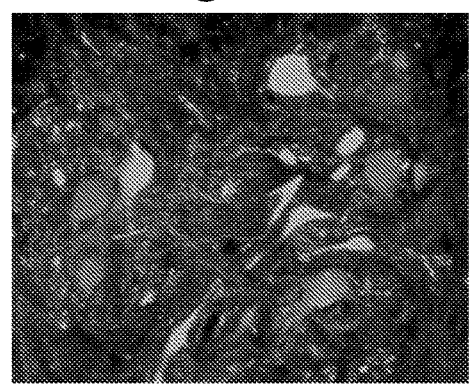

Pig brain sections were dissected and stored in 4% PFA before subjecting the tissues to IHC in order to assess transduction efficiency of AVV.cc47 (FIGS. 11A-11G) and AVV.cc84 (FIGS. 12A-12G) in the frontal cortex, parietal cortex, thalamus, occipital cortex, brainstem, cerebellum, and midbrain. A section of the pig spinal cord was also harvested and subjected to IHC to assess transduction efficiency of AVV.cc47 (FIG. 13A) and AVV.cc84 (FIG. 13B) in the tissue. For a closer inspection, white matter and grey matter of the pig spinal cord was also examined for AVV.cc47 (FIGS. 13C and 13E) and AVV.cc84 (FIGS. 13D and 13F) transduction efficiency, this time by observing either mCherry or GFP fluorescence under magnification, respectively.

Figure 14A:
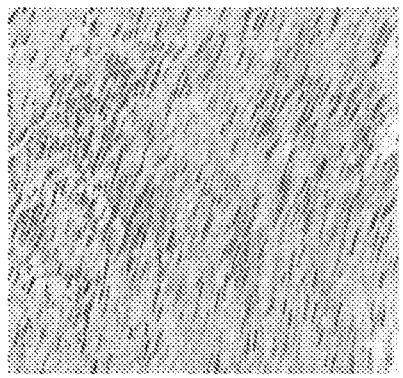
FIGS. 14A-14F illustrate AAV.cc47 and AVV.cc84 transduction in pig heart and liver in accordance with certain embodiments herein. AVV.cc47 transduction was assessed by IHC staining for mCherry in pig heart left ventricle (FIG. 14A), pig heart right ventricle (FIG. 14B), and liver (FIG. 14C). AVV.cc84 transduction was assessed by IHC staining for GFP in pig heart left ventricle (FIG. 14D), pig heart right ventricle (FIG. 14E), and liver (FIG. 14F).
Figure 14B:
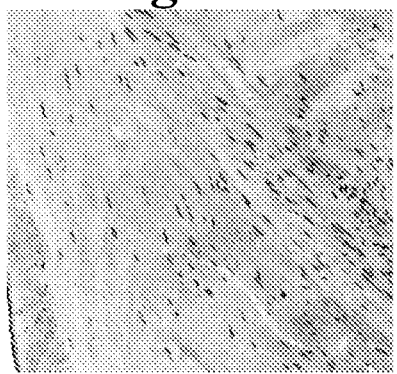
Figure 14C:
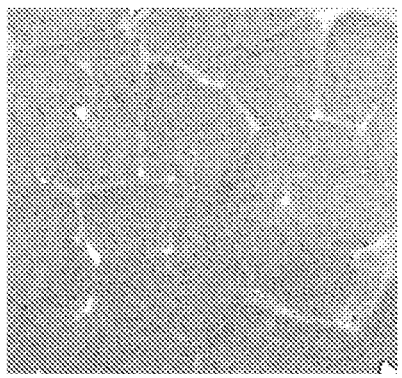
Figure 14D:
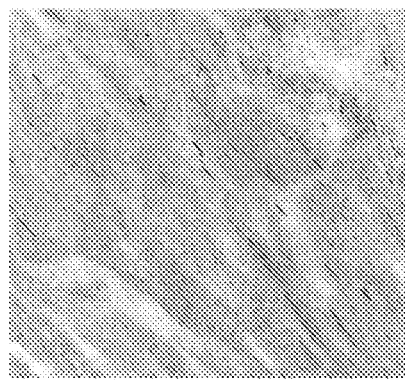
Figure 14E:
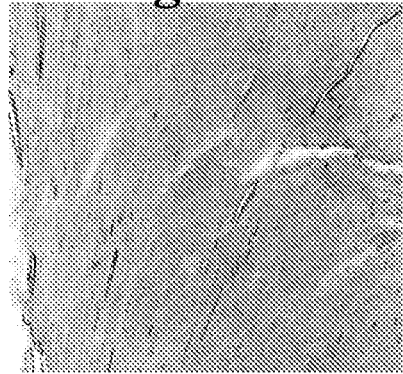
Figure 14F:
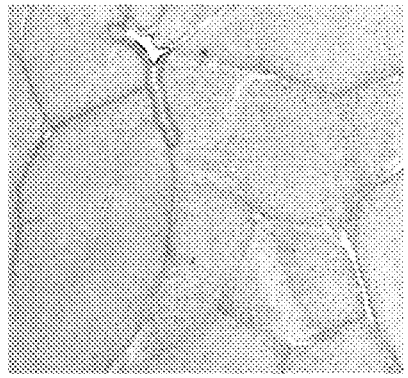

Pig heart and liver tissues were also harvested at the time of sacrifice and subjected to IHC to assess transduction efficiency of AVV.cc47 (FIGS. 14A-14C) and AVV.cc84 (FIGS. 14D-14F).

Example 4. In Vivo Characterization of Recombinant AAVs in Non-Human Primates (NHP)

Figure 15A:
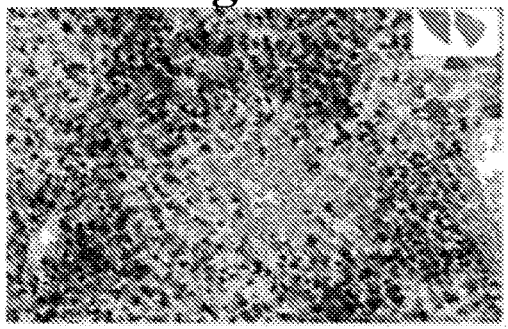
FIGS. 15A-15E illustrate AAV9 and AAV.cc47 transduction in non-human primate heart and liver in accordance with certain embodiments herein. AVV9 transduction was assessed by IHC staining for mCherry in non-human primate liver (FIG. 15A) and heart (FIG. 15C). AVV.cc47 transduction was assessed by IHC staining for mCherry in non-human primate liver (FIG. 15B) and heart (FIG. 15D).
Figure 15B:
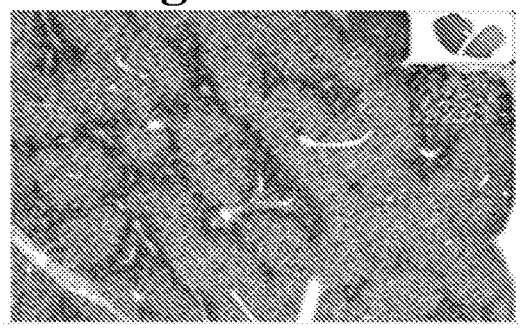
Figure 15C:
Figure 15D:
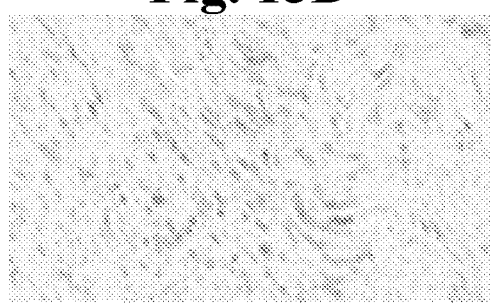
Figure 15E:
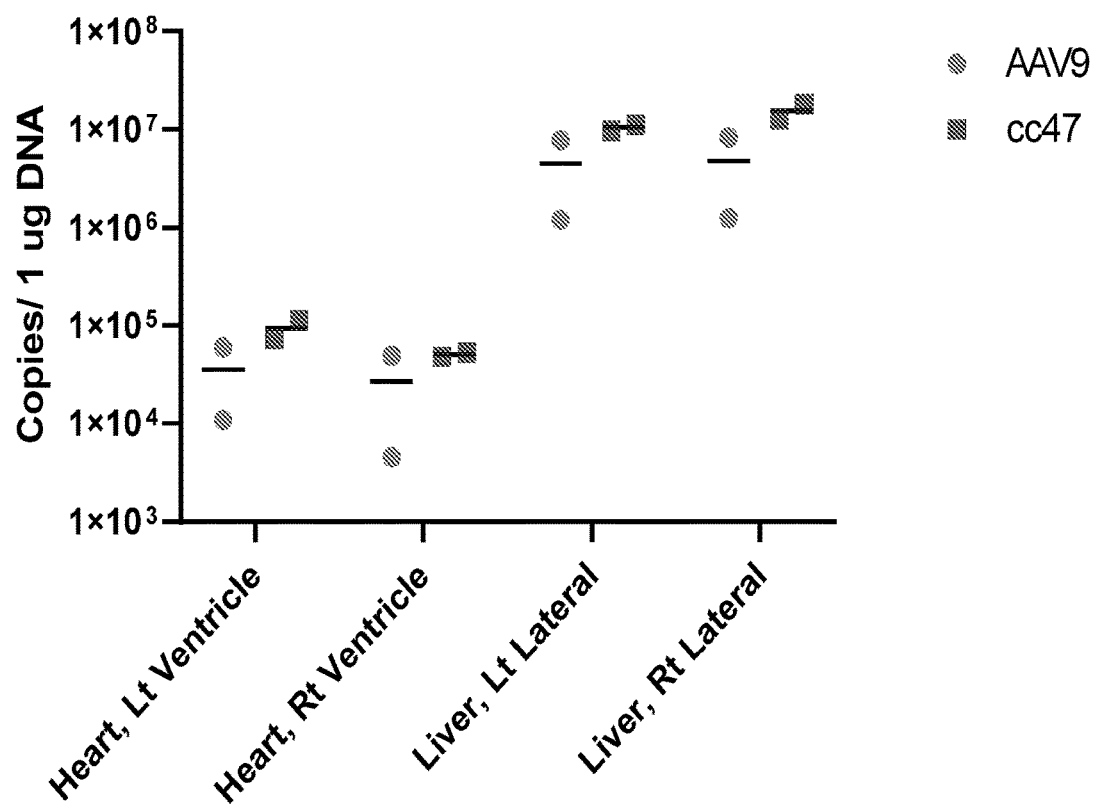

The ccAAV vectors packaging a fluorescence reporter gene used in examples 2 and 3 herein were also used in example 4. Herein, two-year-old Rhesus Macaques (NHPs) weighing approximately 3 kg were injected at the intracisternal magna at a dose of $3.5 \times 10^{12}$ vg/kg with a self-complementary AAV9, AAV.cc47, or AAV.cc84 vector. NHPs were sacked 2 weeks post injection and brain, liver, heart, and spinal cord were harvested. IHC analysis of mCherry for AAV9 in liver (FIG. 15A) and heart (FIG. 15C) and for AAV.cc47 in liver (FIG. 15B) and heart (FIG. 15D) was performed. FIG. 15E shows the vector biodistribution in liver and heart for the AAV9 and AAV.cc47 vectors.

Figure 16A:
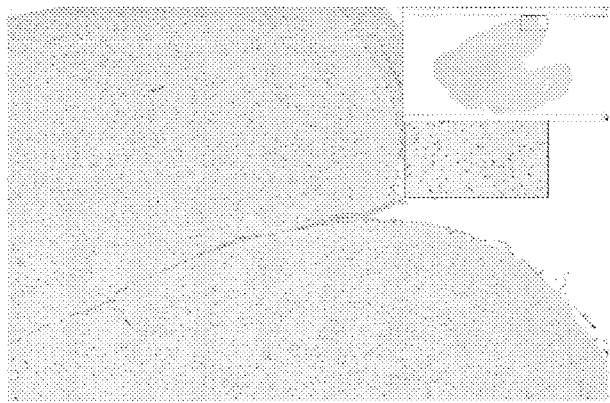
FIGS. 16A-16D illustrate AAV9, AAV.cc47, and AAV.cc84 transduction in non-human primate brain in accordance with certain embodiments herein. AVV9 transduction was assessed by IHC staining for mCherry (FIG. 16B), AAV.cc47 transduction was assessed by IHC staining for mCherry (FIG. 16C), and AAV.cc84 transduction was assessed by IHC staining for GFP (FIG. 16D) in non-human primate brain.
Figure 16B:
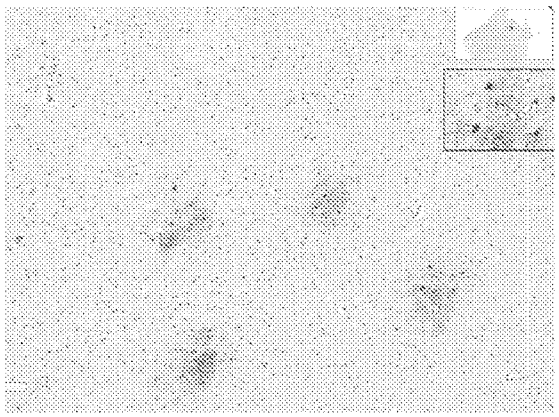
Figure 16C:
Figure 16D:
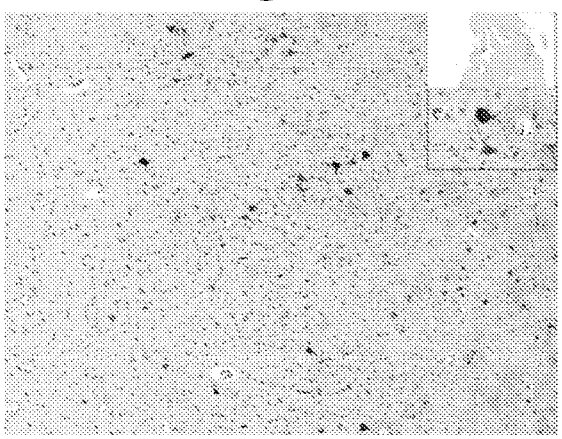

Next, IHC analysis of mCherry for AAV9 and AAV.cc47 and GFP for AAV.cc84 were assessed in the NHP brain. Compared to the sham-treated brain slice (FIG. 16A), AAV9, AAV.cc47, and AAV.cc84 all showed transduction to some extent in the brain tissue (FIGS. 16B-16D). The data suggested that: (1) the cross species capsids had unique biodistribution profiles and differed from AAV9; (2) AAV.cc47 appeared to spread deeper into brain tissue and transduce more cells; and (3) AAV.cc84 also spread well into the tissue but transduced fewer (more specific) cells.

Example 5. AAVcc47 Cardiac Transduction

Figure 17A:
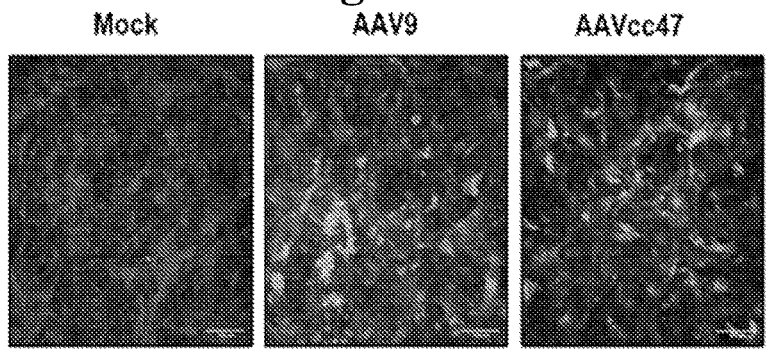
FIGS. 17A-17E illustrate validation of AAVcc47 cardiac transduction in accordance with certain embodiments herein.
Figure 17B:
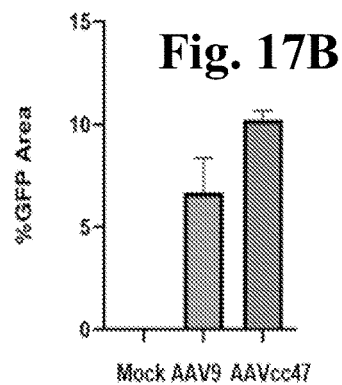
Figure 17C:
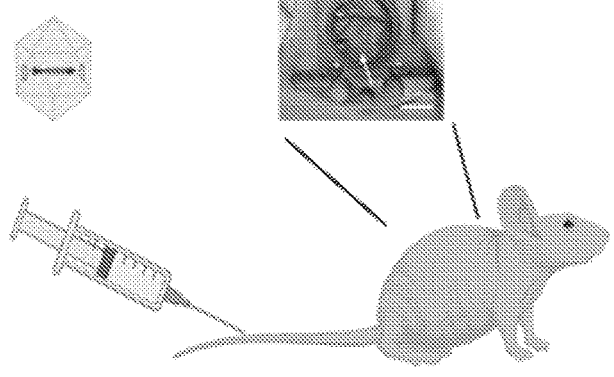
Figure 17D:
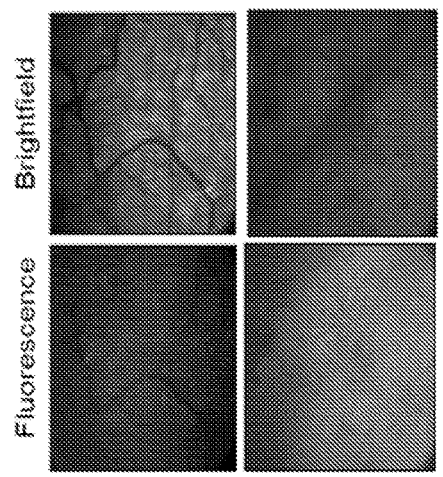
Figure 17E:
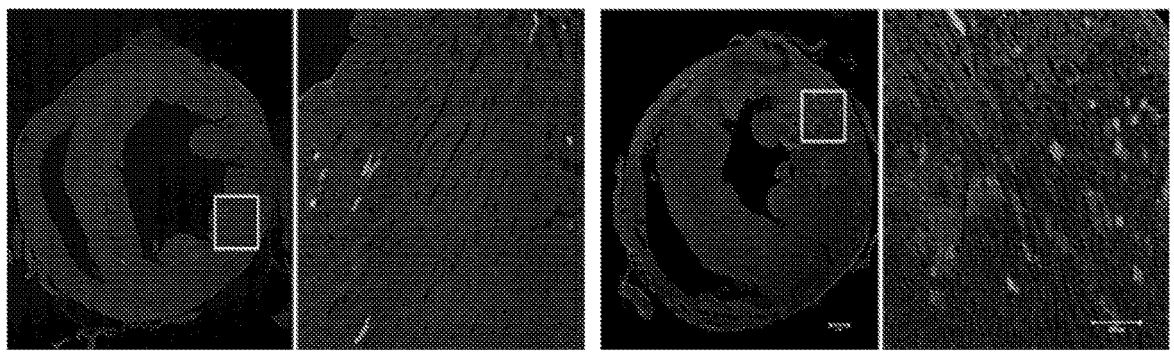

To validate AAVcc47 cardiac transduction, Human iPSC cardiomyocytes were transduced with AAV9 or AAV.cc47 packaging a GFP driven by the Cbh promoter (FIG. 17A). Next, the percent of GFP+ cells in area in multiple images was quantified (FIG. 17B). AAV9 or AAVcc47 packaging CBh:GFP was injected i.v. in a human cardiac patch mouse model (FIG. 17C) and fluorescent imaging of cardiac patch was performed (FIG. 17D). AAV9 and AAV.cc47 were administered again by i.v. to the human cardiac patch mouse model, this time delivering GFP under control of an injury-inducible promoter following myocardial infarction. Immunofluorescence for troponin T (red) and GFP (green) were performed in heart tissue harvested from the mice post injection (FIG. 17E).

Example 6. Cre Recombination with ccAAV Vectors

Figure 18A:
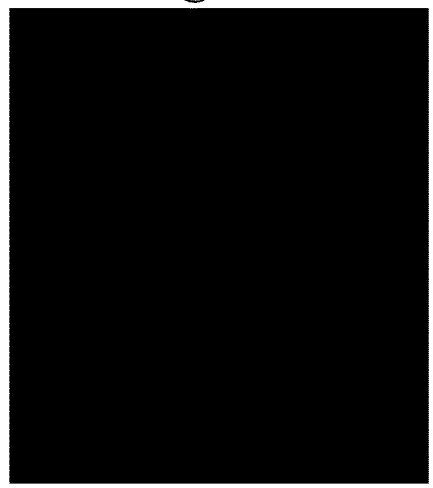
FIGS. 18A-18E illustrate representative images of Native tdTomato fluorescence in the mouse heart following i.v. administration of a mock treatment (FIG. 18A), AAV9 (FIG. 18B), AVV.cc47 (FIG. 18C), and AVV.cc84 (FIG. 18D) in accordance with certain embodiments herein.
Figure 18B:
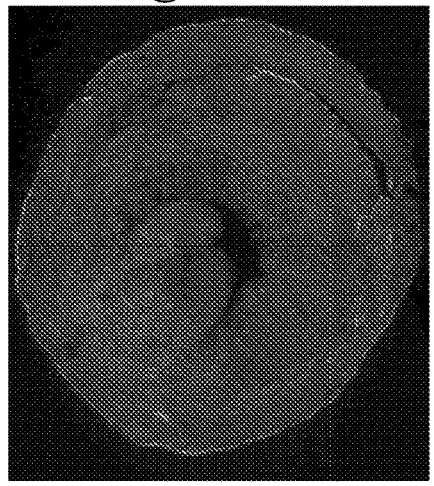
Figure 18C:
Figure 18D:
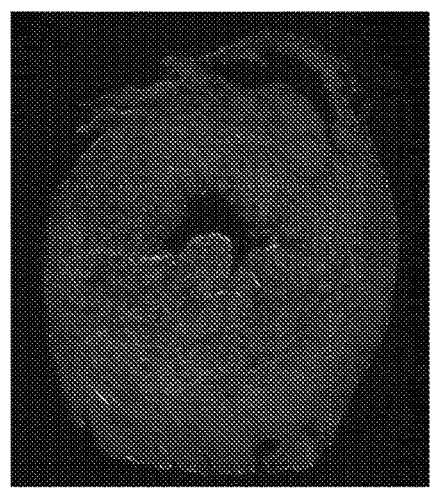
Figure 18E:
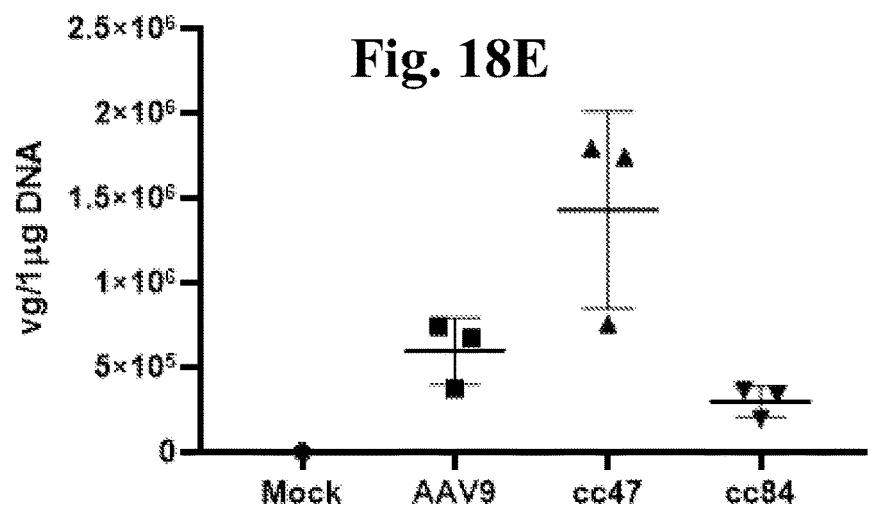
Figure 23A:
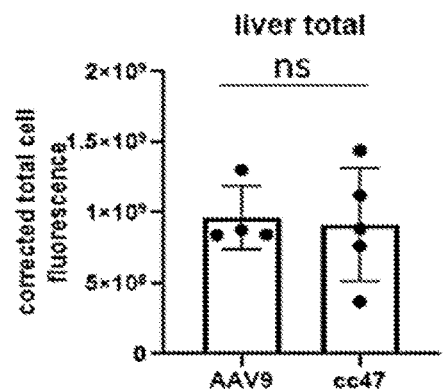
FIGS. 23A-23F illustrate quantification of CRISPR/Cas9 by measuring fluorescence intensity in accordance with certain embodiments herein. Fluorescence intensity was measured from multiple images to quantify native TdTomato expression in Ai9 mice injected with either an AAV9 vector or an AAV.cc47 vector.
Figure 23B:
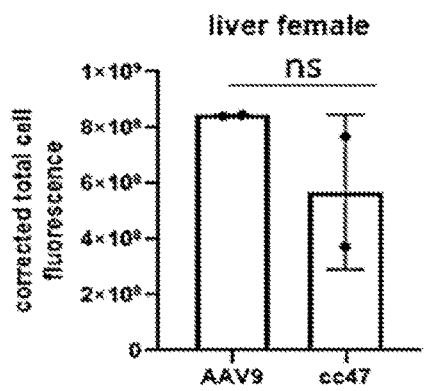
Figure 23C:
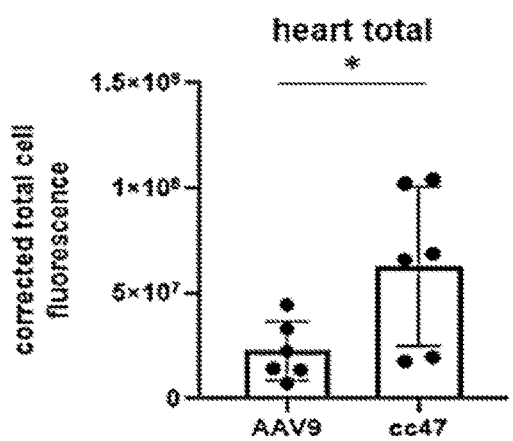
Figure 23D:
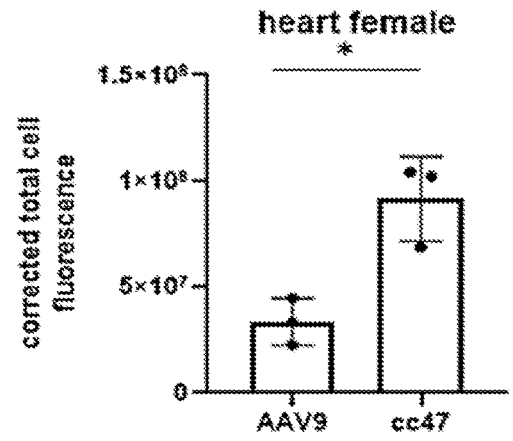
Figure 23E:
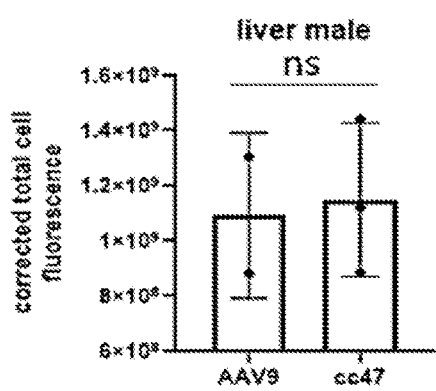
Figure 23F:
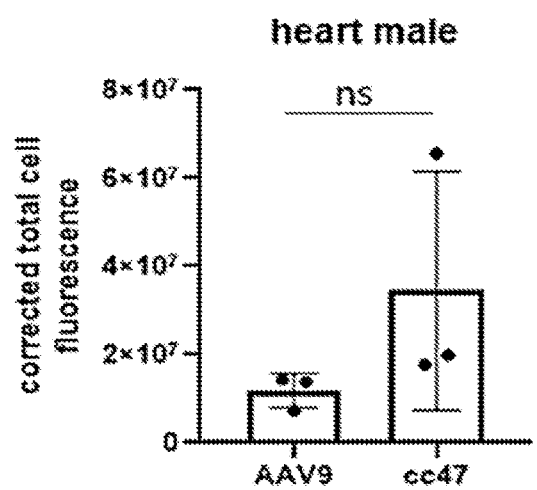

Ai9 male and female mice were injected intravenously at a dose of $1 \cdot 10^{12}$ vg/kg (N=3) with a single stranded AAV9 or ccAAV vector. Animals were sacrificed 4 weeks post injection and multiple organs were harvested and transduction was evaluated by native fluorescence or IF. FIGS. 18A-18D show representative images of Native tdTomato fluorescence following i.v. administration of AAV9 or a ccAAV vectors in the mouse heart and FIG. 18E shows the biodistribution of AAV9, AAV.cc47, and AAV.cc84 vectors in the heart tissue. FIGS. 19A-19D show representative images of Native tdTomato fluorescence following i.v. administration of AAV9 or a ccAAV vectors in the mouse liver and FIG. 19E shows the biodistribution of AAV9, AAV.cc47, and AAV.cc84 vectors in the liver tissue. FIGS. 20A-20D show representative images of Native tdTomato fluorescence co-stained with DAPI (a nuclear marker) and SPC following i.v. administration of AAV9 or a ccAAV vectors in the mouse lung and FIG. 20E shows the biodistribution of AAV9, AAV.cc47, and AAV.cc84 vectors in the lung tissue.

Example 7. CRISPR/Cas9 Gene Editing with a ccAAV Vector

A dual vector strategy was employed using one vector with a truncated CB promoter driving SaCas9 and U6 promoter driving one sgRNA and a second vector of the same design with the second sgRNA (FIG. 21A). Male and female Ai9 mice were injected intravenously at a dose of $2 \times 10^{12}$ vg (N=6) with dual single stranded vectors consisting of sgRNA1 and sgRNA2 mixed 50:50 with AAV9 or ccAAVs. Animals were sacrificed 4 weeks post injection and multiple organs harvested and transduction evaluated by native fluorescence or immunofluorescence (IF).

Native tdTomato fluorescence was assessed in Ai9 mouse liver and heart following administration of AAV9 or AAV.cc47 (FIG. 21B). Gene editing efficiency was determined by counting total number of tdTomato+ cells and dividing by total number of DAPI+ cells (FIG. 21C). A PCR editing assay was performed on liver and heart tissues (FIG. 21D).

The results in FIGS. 21A-21D were validated using the same dual vector strategy with the CB promoter driving SaCas9 expression and each vector have one guide targeted to the Rosa26 locus. These vectors were mixed in equal amounts and injected i.v. at a dose of $1 \times 10^{14}$ vg/kg into Ai9 mice. Ai9 livers were sectioned and imaged for native TdTomato expression (FIG. 22A). Quantification of gene editing efficiencies was performed by counting the total number of TdTomato+ cells and normalizing to the total number of Dapi+ cells (FIG. 22B). Ai9 hearts were sectioned and imaged for native TdTomato expression (FIG. 22C).

Figure 24A:
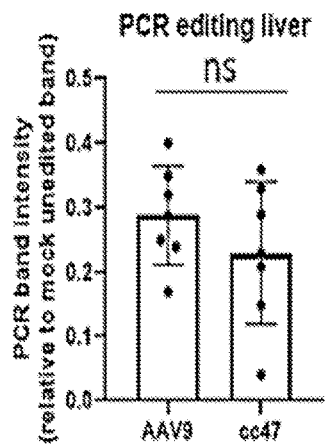
FIGS. 24A-24B illustrate quantification of CRISPR/Cas9 by measuring relative PCR band intensity in accordance with certain embodiments herein.
Figure 24B:
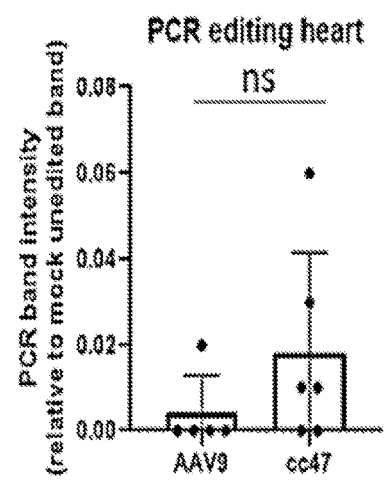
Figure 25A:
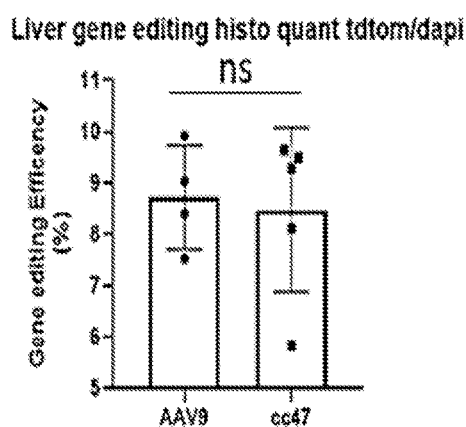
FIGS. 25A-25B illustrate quantification of CRISPR/Cas9 gene editing efficiency in liver and heart in accordance with certain embodiments herein.
Figure 25B:
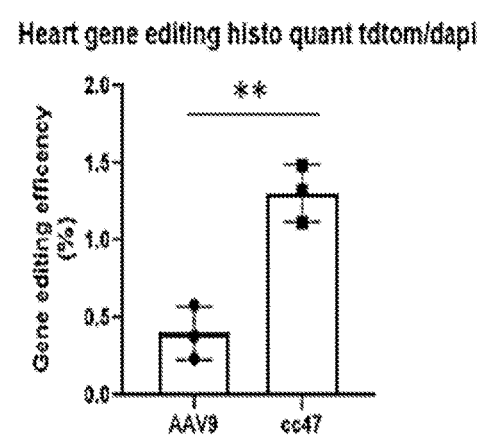

As a means to quantify CRISPR/Cas9 CB, fluorescence intensity was measured from multiple images to quantify native TdTomato expression in the heart and liver tissues of male and female Ai9 mice. (FIGS. 23A-23F). Further, the relative PCR band intensity (mock unedited to experimental sample edited) was measured in FIGS. 24A and 24B. And, in FIGS. 25A and 25B, editing efficiency was quantified using the following formula: Editing efficiency (%)=#of red cells (counted w/image j (liver) or by hand (heart))/#of DAPI stained nuclei.

Figure 29A:
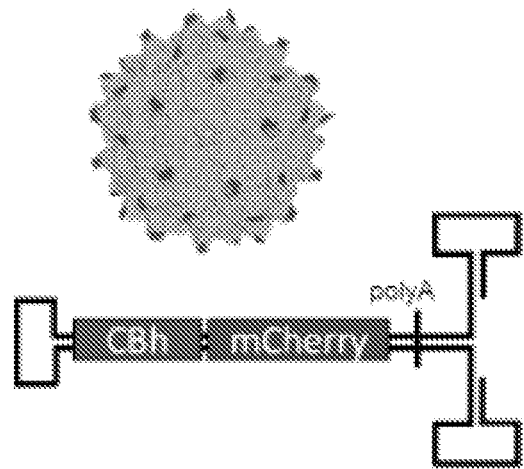
FIGS. 29A-29B illustrate schematic representations of the AAV vectors used for administration in accordance with certain embodiments herein.
Figure 29B:
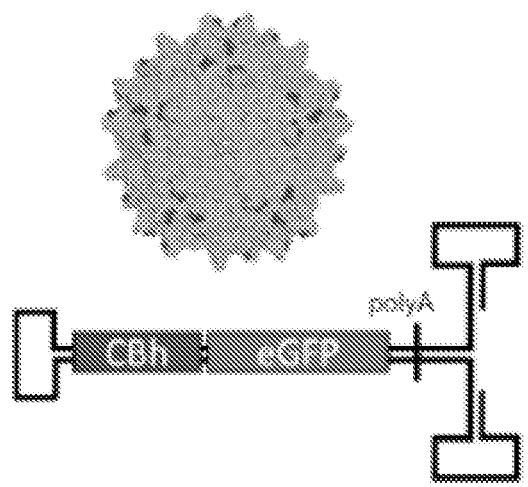

Example 8. Administration of ccAAVs by Intracerebroventricular (ICV) Injection p0 C57/BL6 mouse neonates were injected intracerebroventricular (ICV) at a dose of $1 \times 10^{10}$ vg (N=4) with a self-complementary AAV9 or ccAAV vectors, the constructs of which are depicted in FIGS. 29A and 29B. Animals were sacrificed 4 weeks post injection.

Reporter expression was detected by native fluorescence. FIGS. 30A-30F show representative images of mCherry or eGFP expressed in mouse brain after ICV injection of AAV9 mCherry (FIG. 30A), AAV.cc44 (FIG. 30B), AAV.cc47 (FIG. 30C), AAV9 eGFP (FIG. 30D), AAV.cc81 (FIG. 30E), or AAV.cc84 (FIG. 30F).

Figure 31A:
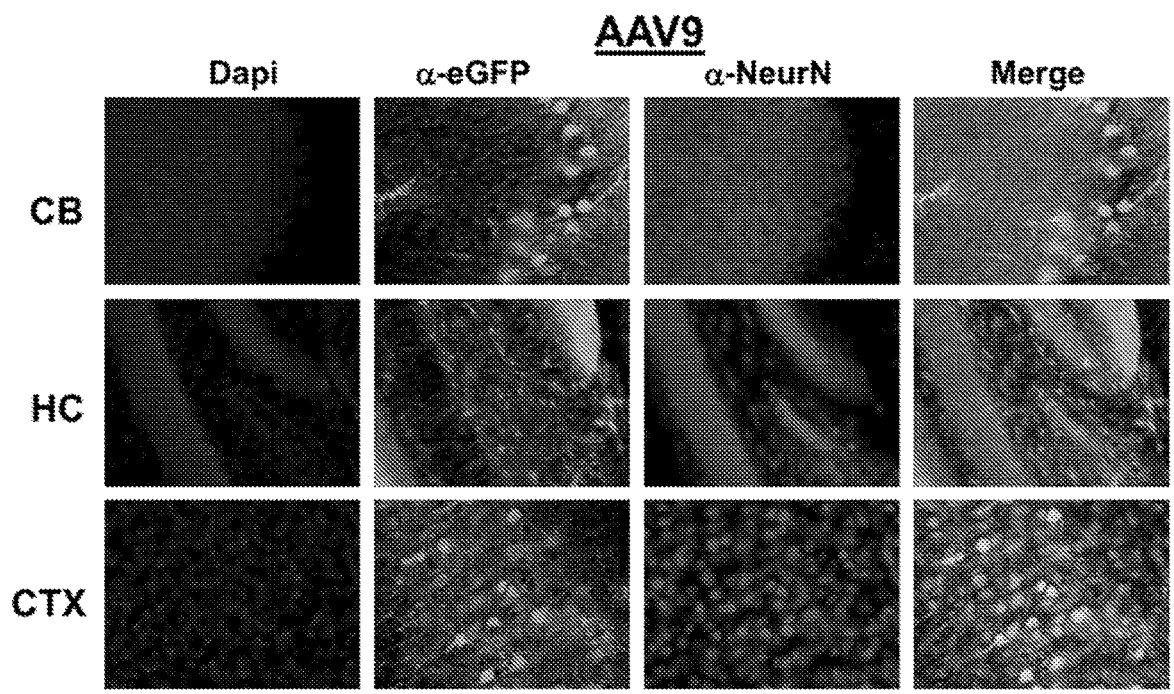
FIGS. 31A-31E illustrate representative images and graphs of eGFP expressed in mouse brain upon intracerebroventricular (ICV) injection of AAV vectors in accordance with certain embodiments herein.
Figure 31B:
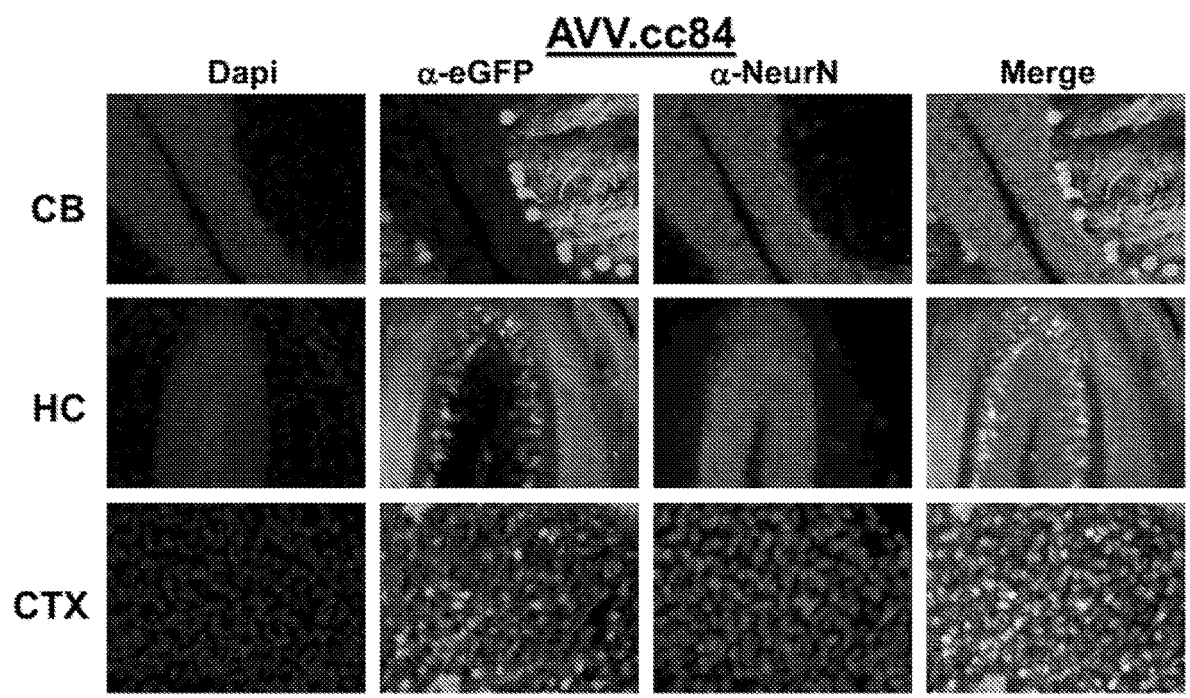
Figure 31C:
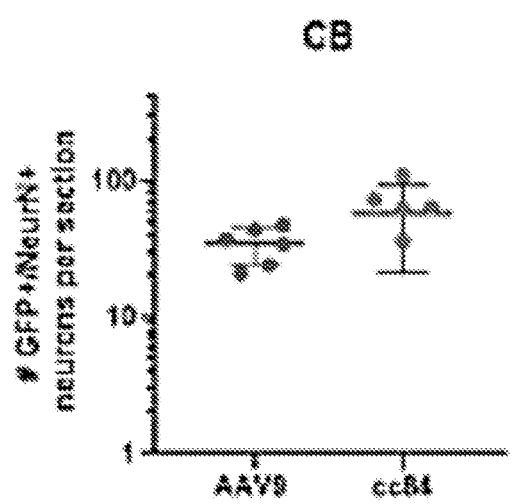
Figure 31D:
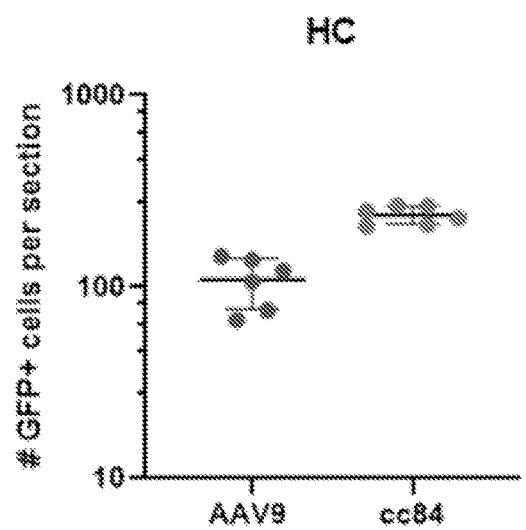
Figure 31E:
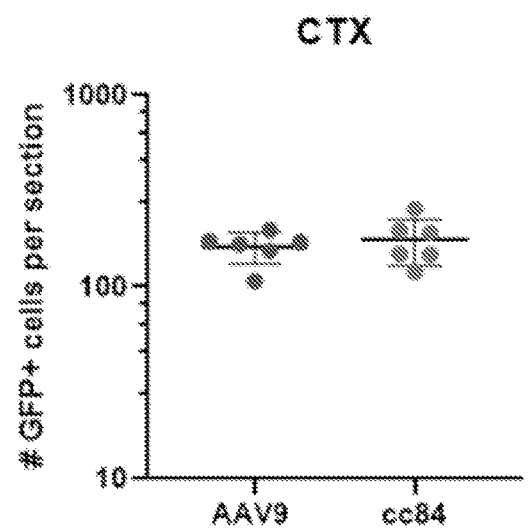
Figure 32A:
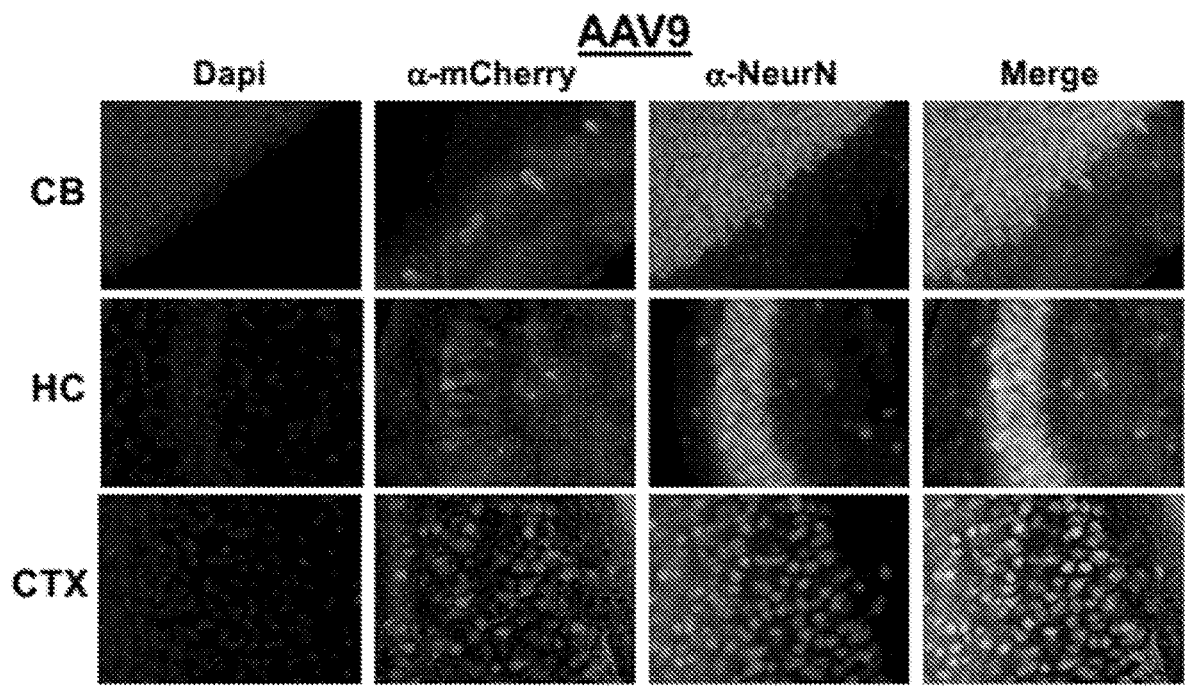
FIGS. 32A-32E illustrate representative images and graphs of mCherry expressed in mouse brain upon intracerebroventricular (ICV) injection of AAV vectors in accordance with certain embodiments herein.
Figure 32B:
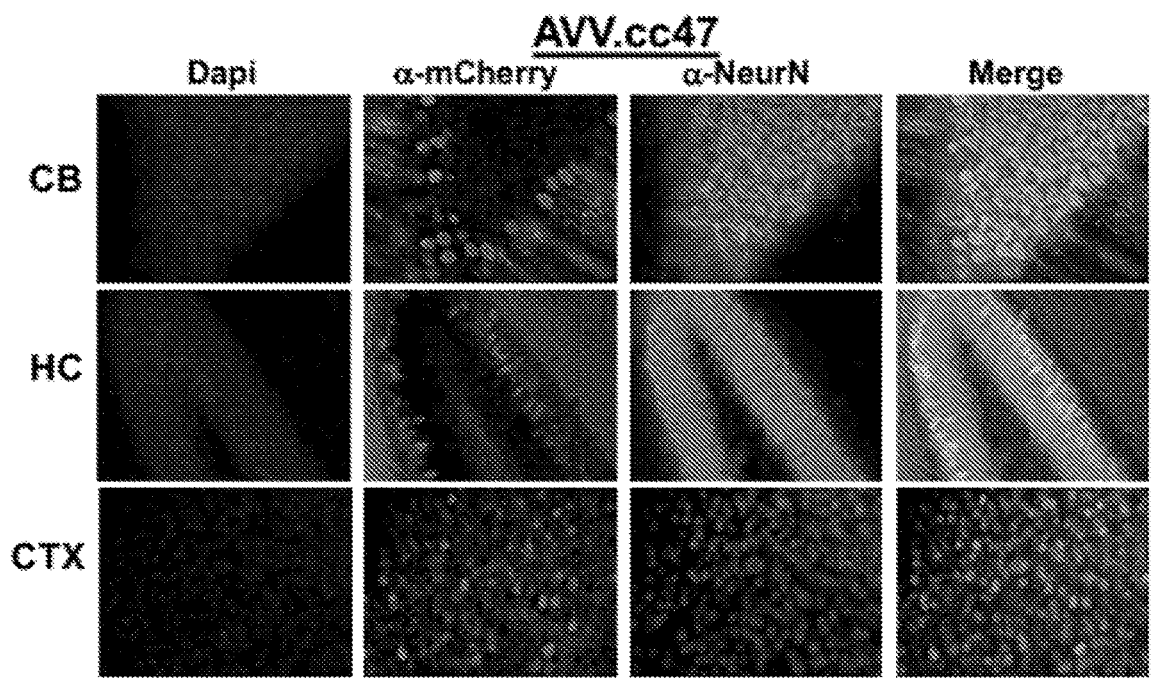
Figure 32C:
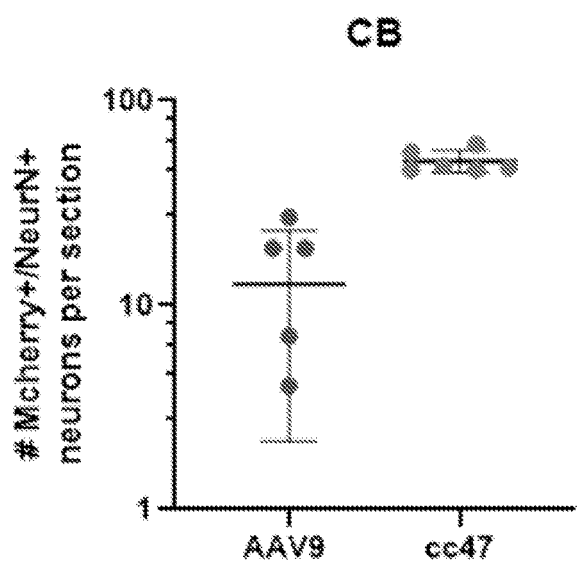
Figure 32D:
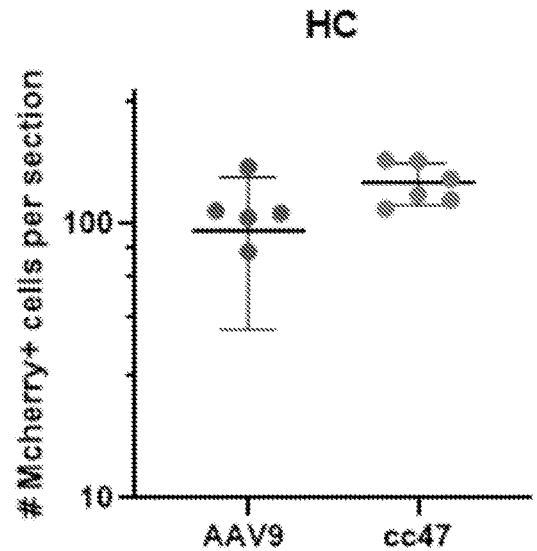
Figure 32E:
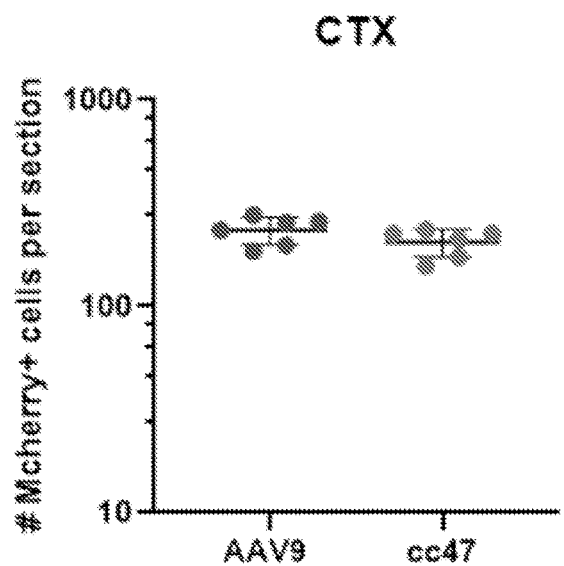

Immunofluorescence (IF) was also performed on the brain tissues harvested from the mice 4 weeks post infection. The tissues were stained with: DAPI (4',6-diamidino-2-phenylindole) which visualized nuclear DNA; an anti-NeurN antibody (α-NeurN), which specifically visualized neuronal nuclei; and either an anti-mCherry (α-mCherry), or anti-eGFP (α-GFP) antibody which visualized the reporter expression of the injected AAV vector. Images were collected for the resulting IF for each antibody and merged to detect colocalization. FIGS. 31A-31B and FIGS. 32A-32B show representative images of the cerebellum, hippocampus, and cerebral cortex region of the brain after IF was performed on the brain tissues of mice harvested 4 weeks post injection of either AAV9 eGFP (FIG. 31A) AAV.cc84 (FIG. 31B), AAV9 mCherry (FIG. 32A), or AAV.cc47 (FIG. 32B). The number of neurons with positive staining for eGFP and NeurN was quantified in cerebellum (FIG. 31C), hippocampus (FIG. 31D), and cerebral cortex (FIG. 31E), of mice injected with either AAV9 (eGFP) or AAV.cc84. The number of neurons with positive staining for mCherry and NeurN was quantified in cerebellum (FIG. 32C), hippocampus (FIG. 32D), and cerebral cortex (FIG. 32E), of mice injected with either AAV9 (mCherry) or AAV.cc47.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

The present disclosure shall control in the event there are any disparities between any definitions and/or description found in the cited references.

Numbered Embodiments

Notwithstanding the appended claims, the following numbered embodiments are also contemplated herein and form part of the instant disclosure:

1. A recombinant AAV vector comprising an AAV capsid protein variant, wherein the capsid protein variant comprises a peptide having the sequence of any one of SEQ ID NOs: 2-19.

2. A recombinant AAV vector comprising an AAV capsid protein variant, wherein the AAV capsid variant has at least 90% identity to the sequence of SEQ ID NO: 1, wherein the amino acids corresponding to amino acids 452-458 of SEQ ID NO: 1 are substituted with a peptide having a sequence of any one of SEQ ID NOs: 20-28.

3. A recombinant AAV vector comprising an AAV capsid protein variant, wherein the AAV capsid variant has at least 90% identity to the sequence of SEQ ID NO: 1, wherein the amino acids corresponding to amino acids 586-592 of SEQ ID NO: 1 are substituted with a peptide having a sequence of any one of SEQ ID NOs: 29-37.

4. A recombinant AAV vector comprising an AAV capsid protein variant, wherein the AAV capsid variant has at least 90% identity to the sequence of SEQ ID NO: 1, wherein the amino acids corresponding to amino acids 452-458 of SEQ ID NO: 1 are substituted with a peptide having a sequence of any one of SEQ ID NOs: 20-28; and wherein the amino acids corresponding to amino acids 586-592 of SEQ ID NO: 1 are substituted with a peptide having a sequence of any one of SEQ ID NOs: 29-37.

5. A recombinant AAV vector comprising an AAV capsid protein variant, wherein the AAV capsid variant has the sequence of any one of SEQ ID NO: 2-19, 46-123 or a sequence with at least 90% or at least 95% identity thereto.

6. A recombinant AAV vector comprising an AAV capsid protein variant, wherein the AAV capsid variant has the sequence of any one of SEQ ID NO: 2-19, 46-123 or a sequence with 1-10, 11-20, 20-30, or 30-50 amino acid substitutions relative thereto.

7. The recombinant AAV vector of any one of embodiments 1-6, wherein the AAV vector comprises a vector genome.

8. The recombinant AAV vector of embodiment 7, wherein the vector genome is encapsidated by an AAV capsid comprising the AAV capsid protein variant.

9. The recombinant AAV vector of embodiment 7 or 8, wherein the vector genome comprises a first inverted terminal repeat (ITR) and a second ITR.

10. The recombinant AAV vector of embodiment 9, wherein the vector genome comprises a transgene located between the first ITR and the second ITR.

11. The recombinant AAV vector of embodiment 10, wherein the transgene encodes a therapeutic RNA.

12. The recombinant AAV vector of embodiment 10, wherein the transgene encodes a therapeutic protein.

13. The recombinant AAV vector of embodiment 10, wherein the transgene encodes a gene-editing molecule.

14. The recombinant AAV vector of embodiment 13, wherein the gene-editing molecule is a nuclease.

15. The recombinant AAV vector of embodiment 14, wherein the nuclease is a Cas9 nuclease.

16. The recombinant AAV vector of embodiment 14, wherein the nuclease is a Cas12a nuclease.

17. The recombinant AAV vector of embodiment 13, wherein the gene-editing molecule is a single guide RNA (sgRNA).

18. An AAV capsid protein variant comprising a peptide having the sequence of any one of SEQ ID NOs: 2-19.

19. An AAV capsid protein variant having at least 90% identity to the sequence of SEQ ID NO: 1, wherein the amino acids corresponding to amino acids 452-458 of SEQ ID NO: 1 are substituted with a peptide having a sequence of any one of SEQ ID NOs: 20-28.

20. An AAV capsid protein variant having at least 90% identity to the sequence of SEQ ID NO: 1, wherein the amino acids corresponding to amino acids 586-592 of SEQ ID NO: 1 are substituted with a peptide having a sequence of any one of SEQ ID NOs: 29-37.

21. An AAV capsid protein variant having at least 90% identity to the sequence of SEQ ID NO: 1, wherein the amino acids corresponding to amino acids 452-458 of SEQ ID NO: 1 are substituted with a peptide having a sequence of any one of SEQ ID NOs: 20-28; and wherein the amino acids corresponding to amino acids 586-592 of SEQ ID NO: 1 are substituted with a peptide having a sequence of any one of SEQ ID NOs: 29-37.

22. An AAV capsid protein variant having the sequence of any one of SEQ ID NO: 2-19, 46-123 or a sequence with at least 90% or at least 95% identity thereto.

23. An AAV capsid protein variant having the sequence of any one of SEQ ID NO: 2-19, 46-123 or a sequence with 1-10, 11-20, 20-30, or 30-50 amino acid substitutions relative thereto.

24. An AAV capsid comprising the AAV capsid protein variant of any one of embodiments 18-23.

25. The AAV capsid of embodiment 24, wherein the AAV capsid comprises about 60 copies of the AAV capsid protein variant, or fragments thereof.

26. The AAV capsid of embodiment 25, wherein the AAV capsid protein variants are arranged with T=1 icosahedral symmetry.

27. A recombinant AAV vector comprising the AAV capsid variant of any one of embodiments 18-23, or the AAV capsid of any one of embodiments 24-26.

28. A pharmaceutical composition comprising the recombinant AAV vector of any one of embodiments 1-17, and 27, and at least one pharmaceutically acceptable carrier.

29. A method of introducing a recombinant AAV vector into a target cell, the method comprising contacting a target cell with a recombinant AAV vector of any one of embodiments 1-17, and 27, or the pharmaceutical composition of embodiment 28.

30. A method of delivering a transgene to a target cell in a subject, the method comprising administering to the subject a recombinant AAV vector of any one of embodiments 1-17, and 27, or the pharmaceutical composition of embodiment 28.

31. The method of any one of embodiments 29 and 30, wherein the target cell is a kidney cell.

32. A method of evolving novel strains of adeno-associated viruses comprising passaging AAV libraries across multiple mammalian species.

33. The method according to embodiment 32, wherein said AAV libraries comprise a plurality of recombinant AAV vectors, wherein each recombinant AAV vector comprises a capsid protein variant comprising one or more amino acid mutations relative to a wildtype AAV capsid protein.

34. The method according to embodiment 33, wherein each recombinant AAV vector in the AAV libraries comprises one or more amino acid mutations relative to a wildtype AAV9 capsid protein (SEQ ID NO: 1).

35. The method according to embodiment 34, wherein the one or more amino acid mutations are in the regions corresponding to amino acids 452-458 of SEQ ID NO: 1 or 586-592 of SEQ ID NO: 1, or the mutations are found in both regions corresponding to amino acids 452-458 and 586-592 of SEQ ID NO: 1.

36. The method according to any one of embodiments 31-35, wherein the method comprises administering a first AAV library to a first mammalian species.

37. The method according to embodiment 36, wherein AAVs from the first AAV library present in one or more target tissues of the first mammalian species are sequenced, and used to generate a second AAV library.

38. The method according to embodiment 37, wherein the second AAV library is administered to a second mammalian species, wherein the first mammalian species and the second mammalian species are different.

39. The method according to embodiment 38, wherein the AAVs from the second AAV library present in one or more target tissues of the second mammalian species and sequenced.

40. The method according to any one of embodiments 36-39, wherein the first mammalian species and the second mammalian species are each independently selected from the group consisting of: *Mus Musculus* (mouse), *Sus scrofa* (pig), *Canis Familiaris* (Dog), Non-human primates (*Macaca*, macaque), and *Homo sapiens* (human).

41. The method according to embodiment 40, wherein the one or more target tissues of the first mammalian species is selected from spinal cord, dorsal root ganglion, brain, heart, lung, kidney, skeletal muscle, spleen, pancreas, small intestine, large intestine, or liver tissue, and any combination thereof.

42. The method according to embodiment 40, wherein the one or more target tissues of the second mammalian species is selected from spinal cord, dorsal root ganglion, brain, heart, lung, kidney, skeletal muscle, spleen, pancreas, small intestine, large intestine, or liver tissue, and any combination thereof.

43. An recombinant adeno-associated virus (AAV) comprising a capsid protein variant evolved using the method of any one of embodiments 31-42.

44. The recombinant AAV according to embodiment 43, wherein the AAV has improved gene transfer efficiency in one or more mammalian species relative to a recombinant AAV that has a capsid protein that is otherwise identical, except it lacks the one or more amino acid substitutions.

45. The recombinant AAV of embodiment 44, wherein the improved gene transfer efficiency is occurs in one more of: *Mus Musculus* (mouse), *Sus scrofa* (pig), *Canis Familiaris* (Dog), Non-human primates (*Macaca*, macaque), or *Homo sapiens* (human).

46. The recombinant AAV of embodiments 43-45, wherein the improved gene transfer efficiency occurs in one or more of the following cell types or tissues: spinal cord, dorsal root ganglion, brain, heart, lung, kidney, skeletal muscle, spleen, pancreas, small intestine, large intestine, or liver.

47. The recombinant AAV of embodiment 46, wherein the improved gene transfer efficiency occurs in kidney cells or kidney tissue.

48. A method of treating a subject in need thereof, comprising: administering to the subject an effective amount of the recombinant AAV vector or any one of embodiments 1-17, 27, and 43-47 or the pharmaceutical composition of embodiment 28.

49. The method of embodiment 48, wherein the subject has a kidney disease or kidney disorder.

We claim:

1. An adeno-associated virus (AAV) vector comprising an AAV capsid protein, wherein the AAV capsid protein comprises the amino acid sequence of SEQ ID NO: 8.

2. The AAV vector of claim 1, wherein the AAV vector comprises a vector genome, wherein the vector genome is encapsidated by the AAV capsid protein.

3. The AAV vector of claim 2, wherein the vector genome comprises at least one terminal repeat sequence.

4. The AAV vector of claim 3, wherein the vector genome comprises a transgene-encoding sequence.

5. The AAV vector of claim 4, wherein the vector genome comprises inverted terminal repeat (ITR) sequences located 3' and 5' of the transgene-encoding sequence.

6. The AAV vector of claim 4, wherein the vector genome further comprises a promoter that controls expression of the transgene-encoding sequence.

7. The AAV vector of claim 4, wherein the transgene-encoding sequence encodes a therapeutic polypeptide.

8. The AAV vector of claim 4, wherein the transgene-encoding sequence encodes a nuclease.

9. The AAV vector of claim 8, wherein the nuclease is a Cas9 nuclease or a Cas12 (a) nuclease.

10. The AAV vector of claim 4, wherein the transgene-encoding sequence encodes a guide RNA.

11. The AAV vector of claim 4, wherein the transgene-encoding sequence encodes a therapeutic RNA.

12. The AAV vector of claim 11, wherein the therapeutic RNA is an antisense oligonucleotide, siRNA, shRNA, or mRNA.

13. A pharmaceutical composition comprising the AAV vector of claim 2 and a pharmaceutically acceptable carrier.

14. A method of introducing a cargo nucleic acid molecule into a cell, comprising contacting the cell with the AAV vector of claim 2.

15. An AAV capsid protein comprising the amino acid sequence of SEQ ID NO: 8.

16. An AAV capsid comprising the AAV capsid protein of claim 15.

17. A plasmid encoding the AAV capsid protein of claim 15.

18. A cell line that comprises the AAV capsid protein of claim 15.

19. The cell line of claim 18, wherein the cell line further comprises a vector genome and an AAV rep gene.

20. A method of making an AAV vector, the method comprising:
  a. culturing a cell line of claim 19 under conditions such that it produces the AAV vector; and
  b. harvesting the AAV vector from the cell.

* * * * *

UNITED STATES PATENT AND TRADEMARK OFFICE
CERTIFICATE OF CORRECTION

PATENT NO. : 12,146,151 B2
APPLICATION NO. : 18/474506
DATED : November 19, 2024
INVENTOR(S) : Aravind Asokan, Trevor Gonzalez and Lawrence Patrick Havlik It is certified that error appears in the above-identified patent and that said Letters Patent is hereby corrected as shown below:

In the Claims

In Claim 9, Column 149, Line 50, delete "Cas12 (a)" and insert -- Cas12a --.

In Claim 15, Column 150, Line 37, delete "AAV" and insert -- adeno-associated virus (AAV) --.

In Claim 16, Column 150, Line 38, delete "An AAV capsid" and insert -- An adeno-associated virus (AAV) capsid --.

In Claim 20, Column 150, Line 48, delete "a" and insert -- the --.

Signed and Sealed this
Thirtieth Day of September, 2025

John A. Squires
*Director of the United States Patent and Trademark Office*

SEQUENCE LISTING

```
Sequence total quantity: 125
SEQ ID NO: 1              moltype = AA   length = 736
FEATURE                   Location/Qualifiers
REGION                    1..736
                          note = AAV9 WT
source                    1..736
                          mol_type = protein
                          organism = synthetic construct
SEQUENCE: 1
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 2              moltype = AA   length = 736
FEATURE                   Location/Qualifiers
REGION                    1..736
                          note = AAV.cc41
source                    1..736
                          mol_type = protein
                          organism = synthetic construct
SEQUENCE: 2
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IEGGTVHAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 3              moltype = AA   length = 736
FEATURE                   Location/Qualifiers
REGION                    1..736
                          note = AAV.cc42
source                    1..736
                          mol_type = protein
                          organism = synthetic construct
SEQUENCE: 3
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IFYGTDSAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 4              moltype = AA   length = 736
FEATURE                   Location/Qualifiers
REGION                    1..736
                          note = AAV.cc43
source                    1..736
                          mol_type = protein
                          organism = synthetic construct
SEQUENCE: 4
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
```

```
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IHGQSASRQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 5           moltype = AA  length = 736
FEATURE                Location/Qualifiers
REGION                 1..736
                       note = AAV.cc44
source                 1..736
                       mol_type = protein
                       organism = synthetic construct
SEQUENCE: 5
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IDTPTNQAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 6           moltype = AA  length = 736
FEATURE                Location/Qualifiers
REGION                 1..736
                       note = AAV.cc45
source                 1..736
                       mol_type = protein
                       organism = synthetic construct
SEQUENCE: 6
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IITRQAYQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 7           moltype = AA  length = 736
FEATURE                Location/Qualifiers
REGION                 1..736
                       note = AAV.cc46
source                 1..736
                       mol_type = protein
                       organism = synthetic construct
SEQUENCE: 7
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IRMFKSNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 8           moltype = AA  length = 736
FEATURE                Location/Qualifiers
```

```
REGION                      1..736
                            note = AAV.cc47
source                      1..736
                            mol_type = protein
                            organism = synthetic construct
SEQUENCE: 8
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGVSLGGGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 9                moltype = AA  length = 736
FEATURE                     Location/Qualifiers
REGION                      1..736
                            note = AAV.cc48
source                      1..736
                            mol_type = protein
                            organism = synthetic construct
SEQUENCE: 9
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IKHFLQGEQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 10               moltype = AA  length = 736
FEATURE                     Location/Qualifiers
REGION                      1..736
                            note = AAV.cc49
source                      1..736
                            mol_type = protein
                            organism = synthetic construct
SEQUENCE: 10
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IMGRERAGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 11               moltype = AA  length = 736
FEATURE                     Location/Qualifiers
REGION                      1..736
                            note = AAV.cc81
source                      1..736
                            mol_type = protein
                            organism = synthetic construct
SEQUENCE: 11
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
```

```
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQLNSSV PSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 12           moltype = AA   length = 736
FEATURE                 Location/Qualifiers
REGION                  1..736
                        note = AAV.cc82
source                  1..736
                        mol_type = protein
                        organism = synthetic construct
SEQUENCE: 12
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPPPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQYMDHQ VSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 13           moltype = AA   length = 736
FEATURE                 Location/Qualifiers
REGION                  1..736
                        note = AAV.cc83
source                  1..736
                        mol_type = protein
                        organism = synthetic construct
SEQUENCE: 13
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPPPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQTSDSL VSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 14           moltype = AA   length = 736
FEATURE                 Location/Qualifiers
REGION                  1..736
                        note = AAV.cc84
source                  1..736
                        mol_type = protein
                        organism = synthetic construct
SEQUENCE: 14
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPPPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNAVGA LSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 15           moltype = AA   length = 736
FEATURE                 Location/Qualifiers
REGION                  1..736
                        note = AAV.cc85
source                  1..736
                        mol_type = protein
```

```
                        organism = synthetic construct
SEQUENCE: 15
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQMPISH HETGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 16           moltype = AA  length = 736
FEATURE                 Location/Qualifiers
REGION                  1..736
                        note = AAV.cc86
source                  1..736
                        mol_type = protein
                        organism = synthetic construct
SEQUENCE: 16
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQDSGAR GATGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 17           moltype = AA  length = 736
FEATURE                 Location/Qualifiers
REGION                  1..736
                        note = AAV.cc87
source                  1..736
                        mol_type = protein
                        organism = synthetic construct
SEQUENCE: 17
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNVALA LGTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 18           moltype = AA  length = 736
FEATURE                 Location/Qualifiers
REGION                  1..736
                        note = AAV.cc88
source                  1..736
                        mol_type = protein
                        organism = synthetic construct
SEQUENCE: 18
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQGALRM GMTGWVQNQG   600
ILPGMVWQDR DVYLQGPIWA KIPHTDGNFH PSPLMGGFGM KHPPPQILIK NTPVPADPPT   660
```

```
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 19            moltype = AA  length = 736
FEATURE                  Location/Qualifiers
REGION                   1..736
                         note = AAV.cc89
source                   1..736
                         mol_type = protein
                         organism = synthetic construct
SEQUENCE: 19
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQLSGEG AVTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 20            moltype = AA  length = 7
FEATURE                  Location/Qualifiers
REGION                   1..7
                         note = AAV.cc41 substitution
source                   1..7
                         mol_type = protein
                         organism = synthetic construct
SEQUENCE: 20
EGGTVHA                                                               7

SEQ ID NO: 21            moltype = AA  length = 7
FEATURE                  Location/Qualifiers
REGION                   1..7
                         note = AAV.cc42 substitution
source                   1..7
                         mol_type = protein
                         organism = synthetic construct
SEQUENCE: 21
FYGTDSA                                                               7

SEQ ID NO: 22            moltype = AA  length = 7
FEATURE                  Location/Qualifiers
REGION                   1..7
                         note = AAV.cc43 substitution
source                   1..7
                         mol_type = protein
                         organism = synthetic construct
SEQUENCE: 22
HGQSASR                                                               7

SEQ ID NO: 23            moltype = AA  length = 7
FEATURE                  Location/Qualifiers
REGION                   1..7
                         note = AAV.cc44 substitution
source                   1..7
                         mol_type = protein
                         organism = synthetic construct
SEQUENCE: 23
DTPTNQA                                                               7

SEQ ID NO: 24            moltype = AA  length = 7
FEATURE                  Location/Qualifiers
REGION                   1..7
                         note = AAV.cc45 substitution
source                   1..7
                         mol_type = protein
                         organism = synthetic construct
SEQUENCE: 24
ITRQAYQ                                                               7

SEQ ID NO: 25            moltype = AA  length = 7
FEATURE                  Location/Qualifiers
REGION                   1..7
                         note = AAV.cc46 substitution
```

```
source                    1..7
                          mol_type = protein
                          organism = synthetic construct
SEQUENCE: 25
RMFKSNQ                                                                    7

SEQ ID NO: 26             moltype = AA   length = 7
FEATURE                   Location/Qualifiers
REGION                    1..7
                          note = AAV.cc47 substitution
source                    1..7
                          mol_type = protein
                          organism = synthetic construct
SEQUENCE: 26
GVSLGGG                                                                    7

SEQ ID NO: 27             moltype = AA   length = 7
FEATURE                   Location/Qualifiers
REGION                    1..7
                          note = AAV.cc48 substitution
source                    1..7
                          mol_type = protein
                          organism = synthetic construct
SEQUENCE: 27
KHFLQGE                                                                    7

SEQ ID NO: 28             moltype = AA   length = 7
FEATURE                   Location/Qualifiers
REGION                    1..7
                          note = AAV.cc49 substitution
source                    1..7
                          mol_type = protein
                          organism = synthetic construct
SEQUENCE: 28
MGRERAG                                                                    7

SEQ ID NO: 29             moltype = AA   length = 7
FEATURE                   Location/Qualifiers
REGION                    1..7
                          note = AAV.cc81 substitution
source                    1..7
                          mol_type = protein
                          organism = synthetic construct
SEQUENCE: 29
LNSSVPS                                                                    7

SEQ ID NO: 30             moltype = AA   length = 7
FEATURE                   Location/Qualifiers
REGION                    1..7
                          note = AAV.cc82 substitution
source                    1..7
                          mol_type = protein
                          organism = synthetic construct
SEQUENCE: 30
YMDHQVS                                                                    7

SEQ ID NO: 31             moltype = AA   length = 7
FEATURE                   Location/Qualifiers
REGION                    1..7
                          note = AAV.cc83 substitution
source                    1..7
                          mol_type = protein
                          organism = synthetic construct
SEQUENCE: 31
TSDSLVS                                                                    7

SEQ ID NO: 32             moltype = AA   length = 7
FEATURE                   Location/Qualifiers
REGION                    1..7
                          note = AAV.cc84 substitution
source                    1..7
                          mol_type = protein
                          organism = synthetic construct
SEQUENCE: 32
NAVGALS                                                                    7

SEQ ID NO: 33             moltype = AA   length = 7
FEATURE                   Location/Qualifiers
REGION                    1..7
```

```
                        note = AAV.cc85 substitution
source                  1..7
                        mol_type = protein
                        organism = synthetic construct
SEQUENCE: 33
MPISHHE                                                                 7

SEQ ID NO: 34           moltype = AA  length = 7
FEATURE                 Location/Qualifiers
REGION                  1..7
                        note = AAV.cc86 substitution
source                  1..7
                        mol_type = protein
                        organism = synthetic construct
SEQUENCE: 34
DSGARGA                                                                 7

SEQ ID NO: 35           moltype = AA  length = 7
FEATURE                 Location/Qualifiers
REGION                  1..7
                        note = AAV.cc87 substitution
source                  1..7
                        mol_type = protein
                        organism = synthetic construct
SEQUENCE: 35
NVALALG                                                                 7

SEQ ID NO: 36           moltype = AA  length = 7
FEATURE                 Location/Qualifiers
REGION                  1..7
                        note = AAV.cc88 substitution
source                  1..7
                        mol_type = protein
                        organism = synthetic construct
SEQUENCE: 36
GALRMGM                                                                 7

SEQ ID NO: 37           moltype = AA  length = 7
FEATURE                 Location/Qualifiers
REGION                  1..7
                        note = AAV.cc89 substitution
source                  1..7
                        mol_type = protein
                        organism = synthetic construct
SEQUENCE: 37
LSGEGAV                                                                 7

SEQ ID NO: 38           moltype = AA  length = 7
FEATURE                 Location/Qualifiers
REGION                  1..7
                        note = VR4
source                  1..7
                        mol_type = protein
                        organism = synthetic construct
SEQUENCE: 38
NGSGQNQ                                                                 7

SEQ ID NO: 39           moltype = AA  length = 7
FEATURE                 Location/Qualifiers
REGION                  1..7
                        note = VR8
source                  1..7
                        mol_type = protein
                        organism = synthetic construct
SEQUENCE: 39
SAQAQAQ                                                                 7

SEQ ID NO: 40           moltype =     length =
SEQUENCE: 40
000

SEQ ID NO: 41           moltype = AA  length = 5
FEATURE                 Location/Qualifiers
REGION                  1..5
                        note = Liver peptide
source                  1..5
                        mol_type = protein
                        organism = synthetic construct
SEQUENCE: 41
```

```
FVFLP                                                                5

SEQ ID NO: 42           moltype = AA  length = 50
FEATURE                 Location/Qualifiers
REGION                  1..50
                        note = Primer, FWD
source                  1..50
                        mol_type = protein
                        organism = synthetic construct
SEQUENCE: 42
CCCTACACGA CGCTCTTCCG ATCTNNNNNG TACCTGTACT ACTTGTCTCG               50

SEQ ID NO: 43           moltype = AA  length = 54
FEATURE                 Location/Qualifiers
REGION                  1..54
                        note = Primer, BKD
source                  1..54
                        mol_type = protein
                        organism = synthetic construct
SEQUENCE: 43
GACTGGAGTT CAGACGTGTG CTCTTCCGAT CTNNNNNAGA CCATACCGGG TAAG          54

SEQ ID NO: 44           moltype = DNA  length = 25
FEATURE                 Location/Qualifiers
misc_feature            1..25
                        note = FWD Primer for AAV2 ITR
source                  1..25
                        mol_type = other DNA
                        organism = synthetic construct
SEQUENCE: 44
aacatgctac gcagagaggg agtgg                                          25

SEQ ID NO: 45           moltype = DNA  length = 29
FEATURE                 Location/Qualifiers
misc_feature            1..29
                        note = REV Primer for AAV2 ITR
source                  1..29
                        mol_type = other DNA
                        organism = synthetic construct
SEQUENCE: 45
catgagacaa ggaaccccta gtgatggag                                      29

SEQ ID NO: 46           moltype = AA  length = 736
FEATURE                 Location/Qualifiers
REGION                  1..736
                        note = AAV.cc41-81
source                  1..736
                        mol_type = protein
                        organism = synthetic construct
SEQUENCE: 46
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IEGGTVHAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQLNSSV PSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 47           moltype = AA  length = 736
FEATURE                 Location/Qualifiers
REGION                  1..736
                        note = AAV.cc41-82
source                  1..736
                        mol_type = protein
                        organism = synthetic construct
SEQUENCE: 47
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
```

```
PFHSSYAHSQ SLDRLMNPLI DQYLYYLSKT IEGGTVHAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQYMDHQ VSTGWVQNQG  600
ILPGMVWQDR DVYLQGPIWA KIPHTDGNFH PSPSLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 48           moltype = AA  length = 736
FEATURE                 Location/Qualifiers
REGION                  1..736
                        note = AAV.cc41-83
source                  1..736
                        mol_type = protein
                        organism = synthetic construct
SEQUENCE: 48
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IEGGTVHAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQTSDSL VSTGWVQNQG  600
ILPGMVWQDR DVYLQGPIWA KIPHTDGNFH PSPSLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 49           moltype = AA  length = 736
FEATURE                 Location/Qualifiers
REGION                  1..736
                        note = AAV.cc41-84
source                  1..736
                        mol_type = protein
                        organism = synthetic construct
SEQUENCE: 49
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IEGGTVHAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQNAVGA LSTGWVQNQG  600
ILPGMVWQDR DVYLQGPIWA KIPHTDGNFH PSPSLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 50           moltype = AA  length = 736
FEATURE                 Location/Qualifiers
REGION                  1..736
                        note = AAV.cc41-85
source                  1..736
                        mol_type = protein
                        organism = synthetic construct
SEQUENCE: 50
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IEGGTVHAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQMPISH HETGWVQNQG  600
ILPGMVWQDR DVYLQGPIWA KIPHTDGNFH PSPSLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 51           moltype = AA  length = 736
FEATURE                 Location/Qualifiers
REGION                  1..736
                        note = AAV.cc41-86
source                  1..736
                        mol_type = protein
```

```
                        organism = synthetic construct
SEQUENCE: 51
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSKSGA QPAKKRLNFG QTGDTE       180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IEGGTVHAQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQDSGAR GATGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 52           moltype = AA  length = 736
FEATURE                 Location/Qualifiers
REGION                  1..736
                        note = AAV.cc41-87
source                  1..736
                        mol_type = protein
                        organism = synthetic construct
SEQUENCE: 52
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IEGGTVHAQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNVALA LGTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 53           moltype = AA  length = 736
FEATURE                 Location/Qualifiers
REGION                  1..736
                        note = AAV.cc41-88
source                  1..736
                        mol_type = protein
                        organism = synthetic construct
SEQUENCE: 53
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IEGGTVHAQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQGALRM GMTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 54           moltype = AA  length = 736
FEATURE                 Location/Qualifiers
REGION                  1..736
                        note = AAV.cc41-89
source                  1..736
                        mol_type = protein
                        organism = synthetic construct
SEQUENCE: 54
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IEGGTVHAQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLSGEG AVTGWVQNQG   600
ILPGMVWQDR DVYLQGPIWA KIPHTDGNFH PSPLMGGFGM KHPPPQILIK NTPVPADPPT   660
```

```
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 55              moltype = AA  length = 736
FEATURE                    Location/Qualifiers
REGION                     1..736
                           note = AAV.cc42-81
source                     1..736
                           mol_type = protein
                           organism = synthetic construct
SEQUENCE: 55
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IFYGTDSAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQLNSSV PSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 56              moltype = AA  length = 736
FEATURE                    Location/Qualifiers
REGION                     1..736
                           note = AAV.cc42-83
source                     1..736
                           mol_type = protein
                           organism = synthetic construct
SEQUENCE: 56
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IFYGTDSAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQYMDHQ VSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 57              moltype = AA  length = 736
FEATURE                    Location/Qualifiers
REGION                     1..736
                           note = AAV.cc42-84
source                     1..736
                           mol_type = protein
                           organism = synthetic construct
SEQUENCE: 57
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IFYGTDSAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNAVGA LSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 58              moltype = AA  length = 736
FEATURE                    Location/Qualifiers
REGION                     1..736
                           note = AAV.cc42-85
source                     1..736
                           mol_type = protein
                           organism = synthetic construct
SEQUENCE: 58
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
```

```
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IFYGTDSAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQMPISH HETGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 59           moltype = AA  length = 736
FEATURE                 Location/Qualifiers
REGION                  1..736
                        note = AAV.cc42-86
source                  1..736
                        mol_type = protein
                        organism = synthetic construct
SEQUENCE: 59
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IFYGTDSAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQDSGAR GATGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 60           moltype = AA  length = 736
FEATURE                 Location/Qualifiers
REGION                  1..736
                        note = AAV.cc42-87
source                  1..736
                        mol_type = protein
                        organism = synthetic construct
SEQUENCE: 60
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IFYGTDSAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNVALA LGTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 61           moltype = AA  length = 736
FEATURE                 Location/Qualifiers
REGION                  1..736
                        note = AAV.cc42-88
source                  1..736
                        mol_type = protein
                        organism = synthetic construct
SEQUENCE: 61
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IFYGTDSAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQGALRM GMTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 62           moltype = AA  length = 736
```

| FEATURE | Location/Qualifiers |
|---|---|
| REGION | 1..736 |
| | note = AAV.cc42-89 |
| source | 1..736 |
| | mol_type = protein |
| | organism = synthetic construct |

SEQUENCE: 62
```
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IFYGTDSAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQLSEG AVTGWVQNQG  600
ILPGMVWQDR DVYLQGPIWA KIPHTDGNFH PSPLMGGFGM KHPPPQILIK NTPVADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736
```

| SEQ ID NO: 63 | moltype = AA  length = 736 |
|---|---|
| FEATURE | Location/Qualifiers |
| REGION | 1..736 |
| | note = AAV.cc43-81 |
| source | 1..736 |
| | mol_type = protein |
| | organism = synthetic construct |

SEQUENCE: 63
```
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IHGQSASRQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQLNSSV PSTGWVQNQG  600
ILPGMVWQDR DVYLQGPIWA KIPHTDGNFH PSPLMGGFGM KHPPPQILIK NTPVADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736
```

| SEQ ID NO: 64 | moltype = AA  length = 736 |
|---|---|
| FEATURE | Location/Qualifiers |
| REGION | 1..736 |
| | note = AAV.cc43-82 |
| source | 1..736 |
| | mol_type = protein |
| | organism = synthetic construct |

SEQUENCE: 64
```
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IHGQSASRQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQYMDHQ VSTGWVQNQG  600
ILPGMVWQDR DVYLQGPIWA KIPHTDGNFH PSPLMGGFGM KHPPPQILIK NTPVADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736
```

| SEQ ID NO: 65 | moltype = AA  length = 736 |
|---|---|
| FEATURE | Location/Qualifiers |
| REGION | 1..736 |
| | note = AAV.cc43-83 |
| source | 1..736 |
| | mol_type = protein |
| | organism = synthetic construct |

SEQUENCE: 65
```
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
```

```
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IHGQSASRQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQTSDSL VSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 66             moltype = AA   length = 736
FEATURE                   Location/Qualifiers
REGION                    1..736
                          note = AAV.cc43-84
source                    1..736
                          mol_type = protein
                          organism = synthetic construct
SEQUENCE: 66
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IHGQSASRQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNAVGA LSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 67             moltype = AA   length = 736
FEATURE                   Location/Qualifiers
REGION                    1..736
                          note = AAV.cc43-85
source                    1..736
                          mol_type = protein
                          organism = synthetic construct
SEQUENCE: 67
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IHGQSASRQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQMPISH HETGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 68             moltype = AA   length = 736
FEATURE                   Location/Qualifiers
REGION                    1..736
                          note = AAV.cc43-86
source                    1..736
                          mol_type = protein
                          organism = synthetic construct
SEQUENCE: 68
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IHGQSASRQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQDSGAR GATGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 69             moltype = AA   length = 736
FEATURE                   Location/Qualifiers
REGION                    1..736
                          note = AAV.cc43-87
source                    1..736
```

```
                        mol_type = protein
                        organism = synthetic construct
SEQUENCE: 69
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IHGQSASRQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNVALA LGTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 70           moltype = AA   length = 736
FEATURE                 Location/Qualifiers
REGION                  1..736
                        note = AAV.cc43-88
source                  1..736
                        mol_type = protein
                        organism = synthetic construct
SEQUENCE: 70
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IHGQSASRQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQGALRM GMTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 71           moltype = AA   length = 736
FEATURE                 Location/Qualifiers
REGION                  1..736
                        note = AAV.cc44-81
source                  1..736
                        mol_type = protein
                        organism = synthetic construct
SEQUENCE: 71
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IHGQSASRQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLSGEG AVTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 72           moltype = AA   length = 736
FEATURE                 Location/Qualifiers
REGION                  1..736
                        note = AAV.cc44-82
source                  1..736
                        mol_type = protein
                        organism = synthetic construct
SEQUENCE: 72
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IDTPTNQAQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQYMDHQ VSTGWVQNQG   600
```

```
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 73               moltype = AA   length = 736
FEATURE                     Location/Qualifiers
REGION                      1..736
                            note = AAV.cc44-83
source                      1..736
                            mol_type = protein
                            organism = synthetic construct
SEQUENCE: 73
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IDTPTNQAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQTSDSL VSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 74               moltype = AA   length = 736
FEATURE                     Location/Qualifiers
REGION                      1..736
                            note = AAV.cc44-84
source                      1..736
                            mol_type = protein
                            organism = synthetic construct
SEQUENCE: 74
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IDTPTNQAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNAVGA LSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 75               moltype = AA   length = 736
FEATURE                     Location/Qualifiers
REGION                      1..736
                            note = AAV.cc44-85
source                      1..736
                            mol_type = protein
                            organism = synthetic construct
SEQUENCE: 75
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IDTPTNQAQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQMPISH HETGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 76               moltype = AA   length = 736
FEATURE                     Location/Qualifiers
REGION                      1..736
                            note = AAV.cc44-86
source                      1..736
                            mol_type = protein
                            organism = synthetic construct
SEQUENCE: 76
MAADGYLPDW LEDNLSEGIR EWWALKPGAP QPKANQQHQD NARGLVLPGY KYLGPGNGLD     60
```

```
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IDTPTNQAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQDSGAR GATGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 77           moltype = AA   length = 736
FEATURE                 Location/Qualifiers
REGION                  1..736
                        note = AAV.cc44-87
source                  1..736
                        mol_type = protein
                        organism = synthetic construct
SEQUENCE: 77
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IDTPTNQAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQNVALA LGTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 78           moltype = AA   length = 736
FEATURE                 Location/Qualifiers
REGION                  1..736
                        note = AAV.cc44-88
source                  1..736
                        mol_type = protein
                        organism = synthetic construct
SEQUENCE: 78
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IDTPTNQAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQGALRM GMTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 79           moltype = AA   length = 736
FEATURE                 Location/Qualifiers
REGION                  1..736
                        note = AAV.cc44-89
source                  1..736
                        mol_type = protein
                        organism = synthetic construct
SEQUENCE: 79
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IDTPTNQAQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQLSGEG AVTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736
```

```
SEQ ID NO: 80              moltype = AA  length = 736
FEATURE                    Location/Qualifiers
REGION                     1..736
                           note = AAV.cc45-81
source                     1..736
                           mol_type = protein
                           organism = synthetic construct
SEQUENCE: 80
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLNSSV PSTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 81              moltype = AA  length = 736
FEATURE                    Location/Qualifiers
REGION                     1..736
                           note = AAV.cc45-82
source                     1..736
                           mol_type = protein
                           organism = synthetic construct
SEQUENCE: 81
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQYMDHQ VSTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 82              moltype = AA  length = 736
FEATURE                    Location/Qualifiers
REGION                     1..736
                           note = AAV.cc45-83
source                     1..736
                           mol_type = protein
                           organism = synthetic construct
SEQUENCE: 82
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQTSDSL VSTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 83              moltype = AA  length = 736
FEATURE                    Location/Qualifiers
REGION                     1..736
                           note = AAV.cc45-84
source                     1..736
                           mol_type = protein
                           organism = synthetic construct
SEQUENCE: 83
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
```

```
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNAVGA LSTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 84          moltype = AA   length = 736
FEATURE                Location/Qualifiers
REGION                 1..736
                       note = AAV.cc45-85
source                 1..736
                       mol_type = protein
                       organism = synthetic construct
SEQUENCE: 84
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQMPISH HETGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 85          moltype = AA   length = 736
FEATURE                Location/Qualifiers
REGION                 1..736
                       note = AAV.cc45-86
source                 1..736
                       mol_type = protein
                       organism = synthetic construct
SEQUENCE: 85
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQDSGAR GATGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 86          moltype = AA   length = 736
FEATURE                Location/Qualifiers
REGION                 1..736
                       note = AAV.cc45-87
source                 1..736
                       mol_type = protein
                       organism = synthetic construct
SEQUENCE: 86
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNVALA LGTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 87          moltype = AA   length = 736
FEATURE                Location/Qualifiers
REGION                 1..736
                       note = AAV.cc45-88
```

```
source                  1..736
                        mol_type = protein
                        organism = synthetic construct
SEQUENCE: 87
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQGALRM GMTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 88           moltype = AA   length = 736
FEATURE                 Location/Qualifiers
REGION                  1..736
                        note = AAV.cc45-89
source                  1..736
                        mol_type = protein
                        organism = synthetic construct
SEQUENCE: 88
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IITRQAYQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLSGEG AVTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 89           moltype = AA   length = 736
FEATURE                 Location/Qualifiers
REGION                  1..736
                        note = AAV.cc46-81
source                  1..736
                        mol_type = protein
                        organism = synthetic construct
SEQUENCE: 89
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IRMFKSNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLNSSV PSTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 90           moltype = AA   length = 736
FEATURE                 Location/Qualifiers
REGION                  1..736
                        note = AAV.cc46-82
source                  1..736
                        mol_type = protein
                        organism = synthetic construct
SEQUENCE: 90
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IRMFKSNQQT LKFSVAGPSN MAVQGRNYIP   480
GPSYRQQRVS TTVTQNNNSE FAWPGASSWA LNGRNSLMNP GPAMASHKEG EDRFFPLSGS   540
```

```
LIFGKQGTGR DNVDADKVMI TNEEEIKTTN PVATESYGQV ATNHQYMDHQ VSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 91           moltype = AA   length = 736
FEATURE                 Location/Qualifiers
REGION                  1..736
                        note = AAV.cc46-83
source                  1..736
                        mol_type = protein
                        organism = synthetic construct
SEQUENCE: 91
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IRMFKSNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQTSDSL VSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 92           moltype = AA   length = 736
FEATURE                 Location/Qualifiers
REGION                  1..736
                        note = AAV.cc46-85
source                  1..736
                        mol_type = protein
                        organism = synthetic construct
SEQUENCE: 92
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IRMFKSNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQMPISH HETGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 93           moltype = AA   length = 736
FEATURE                 Location/Qualifiers
REGION                  1..736
                        note = AAV.cc46-86
source                  1..736
                        mol_type = protein
                        organism = synthetic construct
SEQUENCE: 93
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IRMFKSNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQDSGAR GATGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 94           moltype = AA   length = 736
FEATURE                 Location/Qualifiers
REGION                  1..736
                        note = AAV.cc46-87
source                  1..736
                        mol_type = protein
                        organism = synthetic construct
SEQUENCE: 94
```

```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IRMFKSNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNVALA LGTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 95           moltype = AA  length = 736
FEATURE                 Location/Qualifiers
REGION                  1..736
                        note = AAV.cc46-88
source                  1..736
                        mol_type = protein
                        organism = synthetic construct
SEQUENCE: 95
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IRMFKSNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQGALRM GMTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 96           moltype = AA  length = 736
FEATURE                 Location/Qualifiers
REGION                  1..736
                        note = AAV.cc46-89
source                  1..736
                        mol_type = protein
                        organism = synthetic construct
SEQUENCE: 96
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IRMFKSNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLSGEG AVTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 97           moltype = AA  length = 736
FEATURE                 Location/Qualifiers
REGION                  1..736
                        note = AAV.cc47-81
source                  1..736
                        mol_type = protein
                        organism = synthetic construct
SEQUENCE: 97
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGVSLGGGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLNSSV PSTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736
```

```
SEQ ID NO: 98              moltype = AA   length = 736
FEATURE                    Location/Qualifiers
REGION                     1..736
                           note = AAV.cc47-82
source                     1..736
                           mol_type = protein
                           organism = synthetic construct
SEQUENCE: 98
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGVSLGGGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQYMDHQ VSTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 99              moltype = AA   length = 736
FEATURE                    Location/Qualifiers
REGION                     1..736
                           note = AAV.cc47-83
source                     1..736
                           mol_type = protein
                           organism = synthetic construct
SEQUENCE: 99
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGVSLGGGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQTSDSL VSTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 100             moltype = AA   length = 736
FEATURE                    Location/Qualifiers
REGION                     1..736
                           note = AAV.cc47-84
source                     1..736
                           mol_type = protein
                           organism = synthetic construct
SEQUENCE: 100
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGVSLGGGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNAVGA LSTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 101             moltype = AA   length = 736
FEATURE                    Location/Qualifiers
REGION                     1..736
                           note = AAV.cc47-85
source                     1..736
                           mol_type = protein
                           organism = synthetic construct
SEQUENCE: 101
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
```

```
TTSTRTWALP TYNNHLYKQI SNSTGGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IGVSLGGGQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQMPISH HETGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 102          moltype = AA  length = 736
FEATURE                 Location/Qualifiers
REGION                  1..736
                        note = AAV.cc47-86
source                  1..736
                        mol_type = protein
                        organism = synthetic construct
SEQUENCE: 102
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IGVSLGGGQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQDSGAR GATGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 103          moltype = AA  length = 736
FEATURE                 Location/Qualifiers
REGION                  1..736
                        note = AV.cc47-87
source                  1..736
                        mol_type = protein
                        organism = synthetic construct
SEQUENCE: 103
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IGVSLGGGQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNVALA LGTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 104          moltype = AA  length = 736
FEATURE                 Location/Qualifiers
REGION                  1..736
                        note = AAV.cc47-88
source                  1..736
                        mol_type = protein
                        organism = synthetic construct
SEQUENCE: 104
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTGGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IGVSLGGGQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQGALRM GMTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 105          moltype = AA  length = 736
FEATURE                 Location/Qualifiers
REGION                  1..736
```

```
                         note = AAV.cc47-89
source                   1..736
                         mol_type = protein
                         organism = synthetic construct
SEQUENCE: 105
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGVSLGGGQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQLSGEG AVTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 106           moltype = AA  length = 736
FEATURE                  Location/Qualifiers
REGION                   1..736
                         note = AAV.cc48-81
source                   1..736
                         mol_type = protein
                         organism = synthetic construct
SEQUENCE: 106
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IKHFLQGEQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQLNSSV PSTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 107           moltype = AA  length = 736
FEATURE                  Location/Qualifiers
REGION                   1..736
                         note = AAV.cc48-82
source                   1..736
                         mol_type = protein
                         organism = synthetic construct
SEQUENCE: 107
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IKHFLQGEQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQYMDHQ VSTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 108           moltype = AA  length = 736
FEATURE                  Location/Qualifiers
REGION                   1..736
                         note = AAV.cc48-83
source                   1..736
                         mol_type = protein
                         organism = synthetic construct
SEQUENCE: 108
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IKHFLQGEQT LKFSVAGPSN MAVQGRNYIP  480
```

```
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQTSDSL VSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 109           moltype = AA  length = 736
FEATURE                  Location/Qualifiers
REGION                   1..736
                         note = AAV.cc48-84
source                   1..736
                         mol_type = protein
                         organism = synthetic construct
SEQUENCE: 109
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IKHFLQGEQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNAVGA LSTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 110           moltype = AA  length = 736
FEATURE                  Location/Qualifiers
REGION                   1..736
                         note = AAV.cc48-85
source                   1..736
                         mol_type = protein
                         organism = synthetic construct
SEQUENCE: 110
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IKHFLQGEQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQMPISH HETGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 111           moltype = AA  length = 736
FEATURE                  Location/Qualifiers
REGION                   1..736
                         note = AAV.cc48-86
source                   1..736
                         mol_type = protein
                         organism = synthetic construct
SEQUENCE: 111
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IKHFLQGEQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQDSGAR GATGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 112           moltype = AA  length = 736
FEATURE                  Location/Qualifiers
REGION                   1..736
                         note = AAV.cc48-87
source                   1..736
                         mol_type = protein
                         organism = synthetic construct
```

```
SEQUENCE: 112
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IKHFLQGEQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNVALA LGTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 113        moltype = AA  length = 736
FEATURE               Location/Qualifiers
REGION                1..736
                      note = AAV.cc48-88
source                1..736
                      mol_type = protein
                      organism = synthetic construct
SEQUENCE: 113
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IKHFLQGEQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQGALRM GMTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 114        moltype = AA  length = 736
FEATURE               Location/Qualifiers
REGION                1..736
                      note = AAV.cc48-89
source                1..736
                      mol_type = protein
                      organism = synthetic construct
SEQUENCE: 114
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IKHFLQGEQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLSGEG AVTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 115        moltype = AA  length = 736
FEATURE               Location/Qualifiers
REGION                1..736
                      note = AAV.cc49-81
source                1..736
                      mol_type = protein
                      organism = synthetic construct
SEQUENCE: 115
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IMGRERAGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLNSSV PSTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
```

```
YSEPRPIGTR YLTRNL                                                          736

SEQ ID NO: 116           moltype = AA  length = 736
FEATURE                  Location/Qualifiers
REGION                   1..736
                         note = AAV.cc49-82
source                   1..736
                         mol_type = protein
                         organism = synthetic construct
SEQUENCE: 116
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IMGRERAGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQYMDHQ VSTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                    736

SEQ ID NO: 117           moltype = AA  length = 736
FEATURE                  Location/Qualifiers
REGION                   1..736
                         note = AAV.cc49-83
source                   1..736
                         mol_type = protein
                         organism = synthetic construct
SEQUENCE: 117
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IMGRERAGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQTSDSL VSTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                    736

SEQ ID NO: 118           moltype = AA  length = 736
FEATURE                  Location/Qualifiers
REGION                   1..736
                         note = AAV.cc49-84
source                   1..736
                         mol_type = protein
                         organism = synthetic construct
SEQUENCE: 118
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IMGRERAGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNAVGA LSTGWVQNQG   600
ILPGMVWQDR DVYLQGPIWA KIPHTDGNFH PSPLMGGFGM KHPPPQILIK NTPVADPPT    660
AFNKDKLNSF ITQYSTGQVS VEIEWELQKE NSKRWNPEIQ YTSNYYKSNN VEFAVNTEGV   720
YSEPRPIGTR YLTRNL                                                    736

SEQ ID NO: 119           moltype = AA  length = 736
FEATURE                  Location/Qualifiers
REGION                   1..736
                         note = AAV.cc49-85
source                   1..736
                         mol_type = protein
                         organism = synthetic construct
SEQUENCE: 119
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
```

```
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IMGRERAGQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQMPISH HETGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 120          moltype = AA  length = 736
FEATURE                 Location/Qualifiers
REGION                  1..736
                        note = AAV.cc49-86
source                  1..736
                        mol_type = protein
                        organism = synthetic construct
SEQUENCE: 120
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IMGRERAGQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQDSGAR GATGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 121          moltype = AA  length = 736
FEATURE                 Location/Qualifiers
REGION                  1..736
                        note = AAV.cc49-87
source                  1..736
                        mol_type = protein
                        organism = synthetic construct
SEQUENCE: 121
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IMGRERAGQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNVALA LGTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 122          moltype = AA  length = 736
FEATURE                 Location/Qualifiers
REGION                  1..736
                        note = AAV.cc49-88
source                  1..736
                        mol_type = protein
                        organism = synthetic construct
SEQUENCE: 122
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IMGRERAGQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQGALRM GMTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 123          moltype = AA  length = 736
FEATURE                 Location/Qualifiers
```

```
REGION                  1..736
                        note = AAV.cc49-89
source                  1..736
                        mol_type = protein
                        organism = synthetic construct
SEQUENCE: 123
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT IMGRERAGQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQLSGEG AVTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 124          moltype =   length =
SEQUENCE: 124
000

SEQ ID NO: 125          moltype =   length =
SEQUENCE: 125
000
```